(12) United States Patent
Henkin

(10) Patent No.: US 8,663,938 B2
(45) Date of Patent: Mar. 4, 2014

(54) METHODS FOR DETECTION OF BIOLOGICAL SUBSTANCES

(76) Inventor: Robert I. Henkin, Bethesda, MD (US)

( * ) Notice: Subject to any disclaimer, the term of this patent is extended or adjusted under 35 U.S.C. 154(b) by 0 days.

(21) Appl. No.: 13/618,882

(22) Filed: Sep. 14, 2012

(65) Prior Publication Data

US 2013/0011849 A1    Jan. 10, 2013

Related U.S. Application Data

(63) Continuation of application No. 12/523,040, filed as application No. PCT/US2008/052712 on Jan. 31, 2008, now Pat. No. 8,293,489.

(60) Provisional application No. 60/915,008, filed on Apr. 30, 2007, provisional application No. 60/887,587, filed on Jan. 31, 2007.

(51) Int. Cl.
*G01N 31/00*    (2006.01)
*G01N 33/53*    (2006.01)

(52) U.S. Cl.
USPC ........... 435/7.21; 435/7.1; 436/501; 436/506; 436/518; 530/300; 530/350; 424/9.1; 422/430

(58) Field of Classification Search
None
See application file for complete search history.

(56) References Cited

U.S. PATENT DOCUMENTS

| | | | |
|---|---|---|---|
| 174,915 | A | 3/1876 | Lorenz |
| 4,066,405 | A | 1/1978 | Henkin |
| 4,146,501 | A | 3/1979 | Henkin |
| 4,652,521 | A | 3/1987 | Confer et al. |
| 4,683,195 | A | 7/1987 | Mullis et al. |
| 4,683,202 | A | 7/1987 | Mullis et al. |
| 4,800,159 | A | 1/1989 | Mullis et al. |
| 4,992,445 | A | 2/1991 | Lawter et al. |
| 5,001,139 | A | 3/1991 | Lawter et al. |
| 5,023,252 | A | 6/1991 | Hseih |
| 5,079,142 | A | 1/1992 | Coleman et al. |
| 5,384,308 | A | 1/1995 | Henkin |
| 5,591,645 | A | 1/1997 | Rosenstein |
| 5,601,986 | A | 2/1997 | Takacs |
| 5,622,871 | A | 4/1997 | May et al. |
| 5,707,802 | A | 1/1998 | Sandhu et al. |
| 5,788,967 | A | 8/1998 | Henkin |
| 6,207,703 | B1 | 3/2001 | Ponikau |
| 6,228,660 | B1 | 5/2001 | May et al. |
| 6,387,639 | B1 | 5/2002 | Posner et al. |
| 7,109,042 | B2 | 9/2006 | May et al. |
| 8,293,489 | B2 | 10/2012 | Henkin |

FOREIGN PATENT DOCUMENTS

| | | |
|---|---|---|
| WO | WO 96/41194 A1 | 12/1996 |
| WO | WO 01/48477 A1 | 7/2001 |
| WO | WO 03/025224 A2 | 3/2003 |
| WO | WO 03/025224 A3 | 11/2003 |

OTHER PUBLICATIONS

Agarwal, et al. A simple method for simultaneous estimation of zinc and copper in erythrocytes. Bio. Tr. Elem. Res. 1985;7: 199-208.
Cicinelli, et al. Post-stroke reorganization of brain motor output to the hand: a 2-4 month follow-up with focal magnetic transcranial stimulation. Electroencephalogr Clin Neurophysiol. Dec. 1997;105(6):438-50.
Henkin, et al. A double blind study of the effects of zinc sulfate on taste and smell dysfunction. Amer. J. Med. Sci. 1976;272: 285-299.
Henkin, et al. A zinc protein isolated from human parotid saliva. Proc. Nat. Acad. Sci. USA 1975;72:488-492.
Henkin, et al. Decreased parotid saliva gustin/carbonic anhydrase VI secretion: an enzyme disorder manifested by gustatory and olfactory dysfunction. Amer. J. Med. Sci. 1999;318:380-391.
Henkin, et al. Insulin receptors as well as insulin are present in saliva and nasal mucus. Journal of Investingative Medicine. 2006; 54(Suppl. 2);S378.
Henkin, et al. Nasal seroproteins: a new frontier in the exploration of physiology and pathology of nasal and sinus disease. New Frontiers in Immunobiology. 2000; pp. 127-152.
Henkin, et al. Rapid changes in taste and smell function following transcranial magnetic stimulation (TCMS) in humans: relationship to CAN plasticity. FASEB J. 2002; 16:A878.
Henkin. Concepts of therapy in taste and smell dysfunction: repair of sensory receptor function as primary treatment. Olfaction and Taste XI, (Kurihara, K., Suzuki, N., Ogawa, H., Eds.), Springer Verlag, 1994, pp. 568-573.
Henkin. Drug-induced taste and smell diorders. Incidence, mechanisms and management related primarily to treatment of sensory receptor dysfunction. Drug safety. 1994; 11(5):318-377.
Henkin. Evaluation and treatment of human olfactory dysfunction, in Otolaryngology.(English, G.M. Ed.), Lippincott, Philadelphia, 1993, vol. 2, pp. 1-86.
Henkin. Taste and smell disorders, human. Encyclopedia of Neuroscience, 3rd Ed., (Adelman, G., Smith, B.H., Eds.), Birkhauser, Boston, 2004.
Meret, et al. Simultaneous direct estimation by atomic absorption spectrophotometry of copper and zinc in serum, urine, and cerebrospinal fluid. Clin Chem. May 1971;17(5):369-73.
Moharram, et al. Growth factor regulation in human olfactory system function: the role of transcranial magnetic stimulation (TCMS). FASEB J. 2004; 18(4):A201.
Rickli, et al. Carbonic anhydrases from human erythrocytes. Preparation and properties of two enzymes. J Biol Chem. Apr. 1964;239:1065-78.
Velicu, et al. Insulin is present in human saliva and nasal mucus. Journal of Investingative Medicine. 2006; 54:S385.

*Primary Examiner* — Lisa Cook

(74) *Attorney, Agent, or Firm* — Wilson, Sonsini, Goodrich & Rosati, P.C.

(57) ABSTRACT

Methods and compositions are provided for detection of biological substances in nasal specimen.

18 Claims, 12 Drawing Sheets

Lanes 1-7 HLA   M Mol. wt. markers
   8-14 β-globin

SELDI-TOF MS ANALYSIS of Parotid Saliva before and after rTCMS

METHODS FOR DETECTION OF BIOLOGICAL SUBSTANCES

CROSS-REFERENCE

This application is a continuation application of U.S. application Ser. No. 12/523,040, now U.S. Pat. No. 8,293,489, which was the National Stage of international Application No. PCT/US08/52712, filed Jan. 31, 2008, which in turn claims benefit under 35 U.S.C. §119(e) of U.S. Provisional Application No. 60/915,008, filed Apr. 30, 2007 and U.S. Provisional Application No. 60/887,587 filed Jan. 31, 2007, each of which is incorporated by reference herein for all purposes.

BACKGROUND OF THE INVENTION

Detection and identification of biological substances in tissue samples is used for the diagnosis, prognosis, and monitoring of diseases. Efficient identification of biological substances aids in devising effective treatment strategies.

Most of the current diagnostic techniques involve invasive procedures for the removal of tissue samples or blood. Hence, there is need for the development of minimally invasive procedures for biological sample retrieval.

The present invention provides methods and compositions for detection of biological substances, diagnosis of diseases based on this detection and methods for treatment of the diseases after the diagnosis.

SUMMARY OF THE INVENTION

In one embodiment, a method is provided for detecting a biological substance or element from a nasal specimen of a patient to detect a biological substance or element that is associated with a disease or condition, and where the disease is not a respiratory disease.

In one aspect, the detected biological substance is agouti related protein, alpha fetoprotein (AFP), brain derived neurotrophic factor (BDNF), bone morphogenetic protein-2 (BMP-2), ciliary neurotrophic factor (CNTF), thymus and activation-regulated chemokines (CCL17/TARC) CC chemokines, cystatin, D-dimer, E selectin, endoglin, epidermal growth factor, (EGF), endothelial nitric oxide synthase, (eNOS), FAS ligand, fibroblastic growth factor basic (FGF basis), granulocyte macrophage colony stimulating factor (GM-CSF), hepatocyte growth factor (HGF), inducible nitric oxide synthase (iNOS), insulin-like growth factor 1 (IGF-1), interferon alpha (INF-α), interferon beta (INF-β), interferon gamma (INF-γ), interferon omega (INF-ω), intracellular adhesion molecule 1 (ICAM-1), interleukin-1 (IL-1), interleukin-1 receptor (IL-1 receptor), interleukin-2 (IL-2), interleukin-2 receptor (IL-2 receptor), interleukin-3 (IL-3), interleukin-6 (IL-6), interleukin-15 (IL-15), interleukin-17 (IL-17), interleukin-18 (IL-18), keratinocyte growth factor (KGF), L-selectin, leptin, leukemia inhibitor factor (LIF), matrix metalloproteinase 1 (MMP-1), migrating inhibitory factor (MIF), nerve growth factor (NGF), P selectin, placental growth factor (PlGF), platelet derived growth factor-AA (PDGF-AA), platelet derived growth factor-BB (PDGF-BB), pro-B type natiuretic peptide, receptor for abdominal glycation end product (RAGE), stem cell factor (SCF), substance P, triggering receptor expressed on myeloid cells (TREM-1), transforming growth factor alpha (TGF-alpha), transforming growth factor beta (TGF-beta), tumor necrosis factor (TNF), tumor necrosis factor receptor 1 (TNF-R1), tumor necrosis factor receptor 2 (TNF-R2), TNF-related apoptosis-inducing ligand (TRAIL), vascular cell adhesion molecule 1 (VCAM1), vascular endothelial growth factor C (VEGF-C), vascular growth factor D (VEGF-D), vascular endothelia growth factor receptor 1 (VEGFR1), or vascular endothelia growth factor receptor 2 (VEGFR2).

In another aspect, the detected biological substance is a nucleic acid, a protein, a carbohydrate, a lipid, a metabolite, a hormone, or a combination of these. In a further aspect, the biological substance is a protein. In another aspect, the protein is detected by immunoassay, mass spectrometry, liquid chromatography, electrophoresis, arrays, or biologic sensors. In one aspect detection of a biological substance or element is performed on a point of care device.

In one aspect, the detected element is a metal. In another element the metal is copper or zinc.

In one aspect, the disease or condition associated with a detected biological substance or element is preeclampsia, a bacterial infection, a viral infection, a parasitic infection, a metabolic disease, a gastrointestinal disease, a cardiovascular disease, a neurologic disease, a hematologic disease, an endocrine disease, a malignant disease, an autoimmune disease, or an inflammatory disease.

In another aspect, the method also includes diagnosing a disease or condition. In a still further aspect, the method includes administering a therapeutically effective amount of a drug or active agent to treat the diagnosed disease or condition. In another aspect, the administration route is oral administration, transmucosal administration, buccal administration, nasal administration, parental administration, intravenous administration, subcutaneous administration, intramuscular administration, transdermal administration, or rectal administration. In one aspect, the administration route is by nasal administration.

In one embodiment, a method is provided to detect a biological substance or element in nasal mucus that is associated with the likelihood of occurrence of a disease or condition, and where the disease is not a respiratory disease.

In one aspect, the biological substance associated with the likelihood of occurrence of a disease is agouti related protein, alpha fetoprotein (AFP), brain derived neurotrophic factor (BDNF), bone morphogenetic protein-2 (BMP-2), ciliary neurotrophic factor (CNTF), thymus and activation-regulated chemokines (CCL17/TARC) CC chemokines, cystatin, d-dimer, E selectin, endoglin, epidermal growth factor, (EGF), endothelial nitric oxide synthase, (eNOS), FAS ligand, fibroblastic growth factor basic (FGF basis), granulocyte macrophage colony stimulating factor (GM-CSF), hepatocyte growth factor (HGF), inducible nitric oxide synthase (iNOS), insulin-like growth factor 1 (IGF-1), interferon alpha (INF-α), interferon beta (INF-β), interferon gamma (INF-γ), interferon omega (INF-ω), intracellular adhesion molecule 1 (ICAM-1), interleukin-1 (IL-1), interleukin-1 receptor (IL-1 receptor), interleukin-2 (IL-2), interleukin-2 receptor (IL-2 receptor), interleukin-3 (IL-3), interleukin-6 (IL-6), interleukin-15 (IL-15), interleukin-17 (IL-17), interleukin-18 (IL-18), keratinocyte growth factor (KGF), L-selectin, leptin, leukemia inhibitor factor (LIF), matrix metalloproteinase 1 (MMP-1), migrating inhibitory factor (MIF), nerve growth factor (NGF), P selectin, placental growth factor (PlGF), platelet derived growth factor-AA (PDGF-AA), platelet derived growth factor-BB (PDGF-BB), pro-B type natiuretic peptide, receptor for abdominal glycation end product (RAGE), stem cell factor (SCF), substance P, triggering receptor expressed on myeloid cells (TREM-1), transforming growth factor alpha (TGF-alpha), transforming growth factor beta (TGF-beta), tumor necrosis factor (TNF), tumor necrosis factor receptor 1 (TNF-R1), tumor necrosis factor receptor 2

(TNF-R2), TNF-related apoptosis-inducing ligand (TRAIL), vascular cell adhesion molecule 1 (VCAM1), vascular endothelial growth factor C (VEGF-C), vascular growth factor D (VEGF-D), vascular endothelia growth factor receptor 1 (VEGFR1), or vascular endothelia growth factor receptor 2 (VEGFR2).

In another aspect, the biological substance associated with the likelihood of occurrence of a disease is a nucleic acid, a protein, a carbohydrate, a lipid, a metabolite, a hormone, or combination of the above. In another aspect, the biological substance is a protein. In a further aspect, the protein is detected by immunoassay, mass spectrometry, liquid chromatography, electrophoresis, arrays, or biologic sensors. In one aspect, the biological substance or element is detected using a point of care device. In a further aspect, the point of care diagnostic device is a lateral-flow immunoassay.

In one aspect, the element associated with the likelihood of occurrence of a disease is a metal. In a further aspect, the metal is copper or zinc.

In one aspect, the disease or condition associated with the detected biological substance or element is preeclampsia, a bacterial infection, a viral infection, a parasitic infection, a metabolic disease, a gastrointestinal disease, a cardiovascular disease, a neurologic disease, a hematologic disease, an endocrine disease, a malignant disease, an autoimmune disease, or an inflammatory disease. In another aspect, a prediction is made of the likelihood that the disease or condition will occur.

In one aspect, the method also includes administering a therpeutically effective amount of a drug or active agent to treat a predicted disease or condition. In another aspect, the drug or active agent is administered by way of oral administration, transmucosal administration, buccal administration, nasal administration, parental administration, intravenous administration, subcutaneous administration, intramuscular administration, transdermal administration, or rectal administration. In another aspect, the administration route is nasal administration.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Definitions

Figure 1:
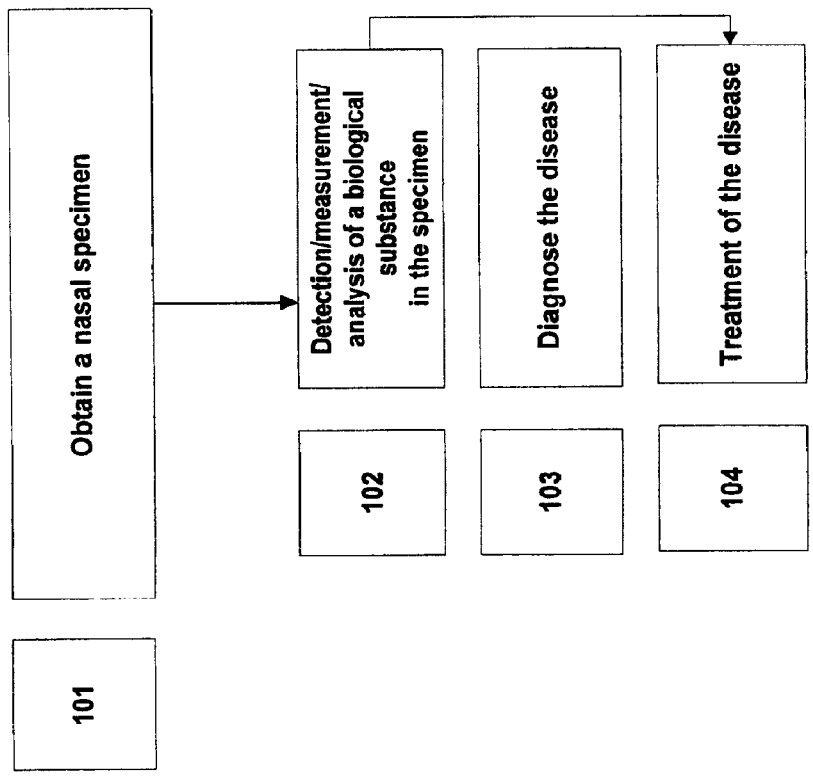
FIG. 1 is a flow chart showing the steps of the methods of the present invention.

The term "diagnosis" as used herein and its grammatical equivalents, means the testing of subjects to determine if they have a particular trait for use in a clinical decision. Diagnosis includes testing of subjects at risk of developing a particular disease resulting from infection by an infectious organism or a non infectious disease, such as cancer or a metabolic disease. Diagnosis also includes testing of subjects who have developed particular symptoms to determine the cause of the symptoms. Diagnosis also includes prognosis, monitoring progress of a disease, and monitoring the efficacy of therapeutic regimens. The result of a diagnosis can be used to classify patients into groups for performance of clinical trials for administration of certain therapies.

The term "drug" as used herein, means any compounds of any degree of complexity that perturbs a biological state, whether by known or unknown mechanisms and whether or not they are used therapeutically. Drugs thus include: typical small molecules of research or therapeutic interest; naturally-occurring factors, such as endocrine, paracrine, or autocrine factors or factors interacting with cell receptors of all types; intracellular factors, such as elements of intracellular signaling pathways; factors isolated from other natural sources; pesticides; herbicides; and insecticides.

The term "nucleic acid" refers to deoxyribonucleotides, deoxyribonucleosides, ribonucleosides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. The term also refers to synthetically generated nucleic acid.

The term "pathogen" as used herein includes, viral, bacterial, fungal, prion, microbial, or other material that can be detected using the teachings of the present invention. The term "pathogen" as used herein can be natural or synthetically generated.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers. As used herein, the terms encompass amino acid chains of any length, including full length proteins (i.e., antigens), wherein the amino acid residues are linked by covalent peptide bonds. The term also refers to synthetically generated polypeptide, peptide or protein.

The term "treating" and its grammatical equivalents as used herein include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

METHODS OF THE INVENTION

The present invention includes methods of analyzing samples from the nose for the detection of biological substances or elements. In some embodiments, nasal secretion or nasal mucus is collected and analyzed for biological substances or elements. In various embodiments, the results of this analysis can confirm the presence (qualitatively or quantitatively) of one or more biological substances or elements. In some embodiments, confirmation of the presence of one or more biological substances or elements allows for the diagnosis or prognosis of a disease or condition and may include the determination of suitability of therapeutic interventions. The techniques of the present invention allow for detection of biological substances that are typically not considered to be present in the nasal area, but are known to be present in other biological fluids such as blood, serum, plasma, etc. Use of nasal specimens provides a minimally invasive manner of obtaining biological samples for analysis. In some embodiments, the methods of the invention are used to detect substances that are not present in other biological fluids such as blood, serum, plasma, etc., but have been now detected in the nasal area.

The term "biological substance" as used herein, and its grammatical equivalents, includes cells and their extra-cellular and intra-cellular constituents. For example, biological substances include pathogens, metabolites, DNA, RNA, lipids, proteins, carbohydrates, receptors, enzymes, hormones, growth factors, growth inhibitory factors, cells, organs, tissues, portions of cells, tissues, or organs, subcellular organelles, chemically reactive molecules like $H^+$, superoxides, ATP, citric acid, protein albumin, as well as combinations or aggregate representations of these types of biological variables. In addition, biological substances can include therapeutic agents such as methotrexate, steroids, non-steroidal anti-inflammatory drugs, soluble TNF-alpha receptor, TNF-alpha antibody, and interleukin-1 receptor antagonists.

A first aspect of the present invention is a method of detecting a biological substance in a nasal specimen, wherein the biological substance is not related to a respiratory disease (e.g., caused by a pathogen). Respiratory diseases caused by pathogens include upper respiratory tract viral infection, upper respiratory tract bacterial infection, bacterial sinusitis, and whooping cough. However, in some embodiments, the methods of the present invention are suitable for detection of substances related to respiratory diseases that are not caused by pathogens, such as allergic rhinitis, asthma, and chronic obstructive pulmonary disease. Furthermore, it should be understood that although some of these diseases are not caused by pathogens, they can be triggered or worsened by pathogens.

A second aspect of the invention is a method of diagnosing a disease by analyzing a nasal specimen for a biological substance that is not related to a respiratory disease. In various embodiments, the results of this analysis can confirm presence (qualitatively or quantitatively) of one or more biological substances. In some embodiments are then suitable for use in diagnosis, prognosis, and determination of suitability of therapeutic interventions.

The biological substances that can be detected by the methods of the present invention include, but are not limited to, insulin, insulin receptors, ghrelin, glucose, caspases, adenylyl cyclases, carbonic anhydrases, endostatin, erythropoetin, carbonic anhydrase VI, cAMP, cGMP, nitric oxide, agouti related protein, alpha fetoprotein (AFP), brain derived neurotrophic factor (BDNF), bone morphogenetic protein-2 (BMP-2), ciliary neurotrophic factor (CNTF), thymus and activation-regulated chemokines (CCL17/TARC) CC chemokines, cystatin, d-dimer, E selectin, endoglin, epidermal growth factor, (EGF), endothelial nitric oxide synthase, (eNOS), FAS ligand, fibroblastic growth factor basic (FGF basis), granulocyte macrophage colony stimulating factor (GM-CSF), hepatocyte growth factor (HGF), inducible nitric oxide synthase (iNOS), insulin-like growth factor 1 (IGF-1), interferon alpha (INF-α), interferon beta (INF-β), interferon gamma (INF-γ), interferon omega (INF-ω), intracellular adhesion molecule 1 (ICAM-1), interleukin-1 (IL-1), interleukin-1 receptor (IL-1 receptor), interleukin-2 (IL-2), interleukin-2 receptor (IL-2 receptor), interleukin-3 (IL-3), interleukin-6 (IL-6), interleukin-15 (IL-15), interleukin-17 (IL-17), interleukin-18 (IL-18), keratinocyte growth factor (KGF), L-selectin, leptin, leukemia inhibitor factor (LIF), matrix metalloproteinase 1 (MMP-1), migrating inhibitory factor (MIF), nerve growth factor (NGF), P selectin, placental growth factor (PlGF), platelet derived growth factor-AA (PDGF-AA), platelet derived growth factor-BB (PDGF-BB), pro-B type natiuretic peptide, receptor for abdominal glycation end product (RAGE), stem cell factor (SCF), substance P, triggering receptor expressed on myeloid cells (TREM-1), transforming growth factor alpha (TGF-alpha), transforming growth factor beta (TGF-beta), tumor necrosis factor (TNF), tumor necrosis factor receptor 1 (TNF-R1), tumor necrosis factor receptor 2 (TNF-R2), TNF-related apoptosis-inducing ligand (TRAIL), vascular cell adhesion molecule 1 (VCAM1), vascular endothelial growth factor C (VEGF-C), vascular growth factor D (VEGF-D), vascular endothelia growth factor receptor 1 (VEGFR1), or vascular endothelia growth factor receptor 2 (VEGFR2).

In various embodiments of the invention a method is provided for the detection of substances related to glucose metabolism such as insulin and insulin receptors. The detection of insulin, insulin receptors, and glucose is used in the diagnosis insulin resistance related conditions, such as diabetes. Use of nasal specimens for the detection of glucose and insulin provides a minimally invasive technique for diagnosis of diabetes and managing diabetes care.

Another embodiment of the invention is the detection of TNFα in nasal specimens. TNFα in nasal mucus was found to be about 30 times higher than in saliva. The concentration of TNFα in nasal specimens, thus, can be reflective of underlying disease processes. This detection is used in the diagnosis of various cancers and inflammatory diseases including but not limited to squamous cell cancer of the head and neck, breast cancer, esophageal cancer, colon cancer and liver cancer. Also, TNFα level monitoring in nasal specimens can be used to monitor the efficacy of cancer and inflammatory disease therapeutics. Further, nasal administration of anti-TNFα drugs provides a means for treatment of diseases in which TNFα plays a role. Also, levels of TNFα in nasal specimens can be used to study apoptosis.

Yet another embodiment of the invention is the detection of leptin, ghrelin and agouti-related protein in nasal specimens. Also, the methods include the administration of substances that modulate leptin, ghrelin and agouti-related protein for the control of appetite and treatment of obesity and anorexia. Nasal administration of leptin can inhibit appetite and nasal administration of agouti-related protein can stimulate appetite. Antibodies to leptin, ghrelin and agouti-related protein can be administered intranasally to modulate appetite. This modulation includes control and/or stimulation.

In some embodiments, the methods of the present invention include detecting cAMP and cGMP in nasal specimens. Comparison of the measurement of cAMP and cGMP in normal subjects with patients with taste and smell loss indicated that patients with taste and smell loss had decreased levels of cAMP in their nasal mucus. Hence, cAMP in nasal mucus can be an index of smell loss. The detection of cAMP and cGMP in the nasal mucus provides a non-invasive method for the detection of taste and smell loss in a subject.

A third aspect of the invention is a method of treating a disease or condition wherein the treatment is based on the diagnosis of the disease by analyzing a nasal specimen for a biological substance. In one embodiment, the disease or condition is not related to a respiratory disease. Preferably, following the diagnosis, a therapeutic is administered which modulates the biological specimen. In some embodiments, the treatment includes nasal administration of biological substances, such as, by way of example only, leptin, ghrelin, agouti-related protein, TNFα, insulin, or homones. In some embodiments, the treatment includes nasal administration of therapeutic that modulates the identified biological substances.

In one embodiment a method is provided for treating diabetes and/or insulin resistance, following detection of insulin, insulin receptor and/or glucose, by administering to a subject in a therapeutically effective amount a drug or agent that modulates the insulin, insulin receptor and/or glucose is administered. In one embodiment, this administration is via nose.

In various embodiments, a drug or agent can include antidiabetic drugs, including insulin.

In another aspect of the invention, a method is provided for treating cancer comprising detecting one or more biological substances in a nasal specimen, where the biological substance(s) are associated with a cancer. In one embodiment for treating cancer, following detection of TNFα, p53 or mutated p53, a drug that modulates the TNFα, p53 or mutated p53 is administered. In one embodiment, a drug or active (e.g., anticancer drug or agent) this administration is via nose.

In another aspect of the invention, a method is provided for treating a bacterial pathogen comprising detecting one or more biological substances in a nasal specimen, where the biological substance(s) are associated with a bacterial pathogen. In one embodiment for treating leprosy, following detection of antibodies against *mycobacterium leprae*, an antibiotic drug is administered. In one embodiment, this administration is via nose.

In another aspect of the invention, a method is provided for treating a virus or viral infection comprising detecting one or more biological substances in a nasal specimen, where the biological substance(s) are associated with a virus or viral infection. In one embodiment for treating hepatitis, including hepatitis A, B, C, D, E and G, following detection of antibodies against hepatitis causing virus, a drug, such as, by way of example only, interferon is administered. In one embodiment, this administration is via nose. In one embodiment for treating flu, following detection of flu causing pathogen or antibodies against flu causing pathogen, a drug that modulates the infection is administered. Preferably, this administration is via nose. The drug can include antibiotics or other drugs known in the art.

In another aspect of the invention, a method is provided for treating a weight condition or disorder comprising detecting one or more biological substances in a nasal specimen, where the biological substance(s) are associated with a weight condition or disorder. In one embodiment a method is provided for treating obesity, following detection of leptin or agouti-related protein, a drug that modulates the leptin or agouti-related protein is administered. The drug or agent can include anti-agouti-related protein or leptin. In one embodiment for treating anorexia, following detection of leptin or agouti-related protein, a drug that modulates the leptin or agouti-related protein is administered. The drug can include anti-leptin or agouti-related protein.

In another aspect of the invention, a method is provided for treating a smell loss or tase loss condition or disorder comprising detecting one or more biological substances in a nasal specimen, where the biological substance(s) are associated with a weight condition or disorder. In one embodiment for treating smell loss or taste loss, following detection of TNFα, CA VI, or TRAIL, a drug that modulates the TNFα, CA VI or TRAIL is administered. The drug or active agent can include theophylline or other drugs known in the art. In any of the methods of disclosed herein a drug or active agent can be administered through the nose.

The biological substances in the body interact with the brain via a feedback mechanism. The biological substances present in the nose are secreted by glands that are controlled by a brain function and via the feedback mechanism, these biological substances after secretion, in turn affect the brain function. The nasal administration of the biological substance after diagnosing the disease by detecting the biological substance in the nasal secretion may be reflective of this feedback mechanism.

In some embodiments, the treatment includes transcranial magnetic stimulation (TCMS). TCMS or rTCMS (repetitive TCMS) can induce secretion of biological substances in the body, thereby inducing clinical changes. The patients suffering from loss of taste and/or smell (hypogeusia and/or hyposmia, respectively) when treated with rTCMS, showed improvement in their sensory acuity and decrease in their sensory distortions. Some biological substances in these patients, such as, CA I, II and VI, zinc, and copper were found to be significantly higher in blood plasma, erythrocytes and saliva after treatment with TCMS. The increase of the biological substances in the body after TCMS indicates that TCMS induces biochemical changes in the body and can be used to treat various diseases including clinical abnormalities of sensory function and neurological disorders.

The methods of the present invention disclosed herein include methods for detecting, diagnosing, and treating a disease in a subject (or a combination thereof), by analyzing one or more biological substances in nasal tissue or secretion. The steps of the methods of the present invention are depicted in FIG. 1. Without limiting the scope of the present invention, the steps can be performed independent of each other or one after the other. One or more steps may be skipped in the methods of the present invention. A sample of nasal secretion is collected from a subject at step 101. One or more biological substances in the specimen is detected, measured and/or analyzed at step 102 by detection techniques known in the art, such as, PCR, mass spectrometry, protein assays etc. By way of example only some of the detection techniques are disclosed herein. A disease is diagnosed at step 103 based on the detection, measurement and/or analysis of the biological substance. A decision regarding treatment of the disease is made at step 104, the treatment decision being made based on the diagnosis.

The identification of the biological substances may involve one or more comparisons with reference specimens. The reference specimen may be obtained from the same subject or from a different subject who is either not affected with the disease or is a patient. The reference specimen could be obtained from one subject, multiple subjects or be synthetically generated. The identification may also involve the comparison of the identification data with the databases to identify the biological substance.

The steps of the methods of the present invention are provided herein. Without limiting the scope of the present invention, other techniques for collection of sample, detection of the biological substances and diagnosis of the disease are known in the art and are within the scope of the present invention.

Sample Collection

In the sample collection step, specimens from the nasal area are collected for analysis. In some embodiments of the invention, a sample of nasal secretions is collected directly from the nose into a collection tube or device. In other embodiments of the invention, a sample of nasal secretion is collected on a sample collection device by passing it into the nostril of a patient. The device may be inserted sequentially into each nostril of the patient and advanced parallel to the hard palate with slow rotation. The device is then typically transferred to a transport tube, such as a glass or plastic test tube. The transport tube may include a suitable volume of a sterile medium such as ethanol or the like.

Suitable sample collection devices are well known to those skilled in the art. In one embodiment, a sample collection device can be a swab, a wooden spatula, bibulous materials such as a cotton ball, filter, or gauze pad, an absorbent-tipped applicator, capillary tube, and a pipette. Preferably, a swab can be used as a sample collection device, and the sample processing element comprises a swab holder or a swab processing insert. The swab holder or swab processing insert can be tapered or angled to allow a single sample processing element to accommodate all types of swabs by allowing swabs with different amounts of fiber, or that are wound to different levels of tightness, to be held securely within the holder or insert. Most preferably, the swab holder or swab processing insert securely holds the swab to provide stability. In one embodiment, the sample collection device is dry and sterile. In another embodiment, a dry, sterile sample collection device is moistened before use with a sterile liquid. The moistening solution can be a carrier solution to assist in the collection of material. Alternately, the moistening solution can be a transport solution for the sampling of microbes and viruses. A suitable viral transport medium is 5% tryptose phosphate broth, 0.5% bovine serum albumin, and antibiotics in phosphate-buffered saline.

The sample collection step can also be incorporated into a diagnostic device. In one embodiment, the sample is collected by a point of care diagnostic device. In a preferred embodiment, the point of care diagnostic device is a lateral flow immunoassay. Patents concerning the use of such devices include U.S. Pat. Nos. 5,079,142; 5,591,645; 5,601,986; 5,622,871; 6,228,660; and 7,109,042. Foreign applications include PCT GB 88-00322. All patents and applications are incorporated by reference in their entirety.

In some instances, samples may be collected from individuals repeatedly over a longitudinal period of time (e.g., once a day, once a week, once a month, biannually or annually). Obtaining numerous samples from an individual over a period of time can be used to verify results from earlier detections and/or to identify an alteration as a result of, for example, drug treatment. Samples can be obtained from humans or non-humans. Preferably, samples are obtained from humans.

Analysis

In the present invention, a specimen of nasal mucus, secretion, or tissue is collected and analyzed using one or more analytical techniques including enzymatic technique, ELISA, fluorometric technique, mass spectrography, HPLC, GLC, PCR, and other similar techniques. The present invention also includes methods of diagnosing a disease by analyzing nucleic acids in a nasal specimen by nucleic acid detection methods such as, but are not limited to polymerase chain reaction (PCR), ligase chain reaction (LCR), strand displacement amplification (SDA), self-sustained sequence replication (3SR), array based tests, and TAQMAN. A number of template dependent processes are available to amplify the target sequences of interest present in a sample. One of the best known amplification methods is the polymerase chain reaction (PCR) which is described in detail in U.S. Pat. Nos. 4,683,195, 4,683,202 and 4,800,159.

Polymerase Chain Reaction (PCR)

The polymerase chain reaction (PCR) is a process for amplifying one or more desired specific nucleic acid sequences found in a nucleic acid. Because large amounts of a specific sequence may be produced by this process, it is used for improving the efficiency of cloning DNA or messenger RNA and for amplifying a target sequence to facilitate detection thereof.

PCR involves a chain reaction for producing, in exponential quantities relative to the number of reaction steps involved, at least one specific nucleic acid sequence given (a) that the ends of the required sequence are known in sufficient detail that oligonucleotides can be synthesized which will hybridize to them, and (b) that a small amount of the sequence is available to initiate the chain reaction. The product of the chain reaction would be a discrete nucleic acid duplex with termini corresponding to the ends of the specific primers employed.

Any source of nucleic acid, in purified or non purified form, can be utilized as the starting nucleic acid or acids, provided it contains or is suspected of containing the specific nucleic acid sequence desired. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acid produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as a portion of the β-globin gene contained in whole human DNA or a portion of nucleic acid sequence due to a particular microorganism which organism might constitute only a very minor fraction of a particular biological sample. The starting nucleic acid may contain more than one desired specific nucleic acid sequence which may be the same or different. Therefore, it is useful not only for producing large amounts of one specific nucleic acid sequence, but also for amplifying simultaneously more than one different specific nucleic acid sequence located on the same or different nucleic acid molecules.

The nucleic acid or acids may be obtained from any source, for example, from plasmids such as pBR322, from cloned DNA or RNA, or from natural DNA or RNA from any source, including bacteria, yeast, viruses, and higher organisms such as plants or animals. DNA or RNA may be extracted from blood, tissue material such as chorionic villi or amniotic cells.

It will be understood that the word primer as used hereinafter may refer to more than one primer, particularly in the case where there is some ambiguity in the information regarding the terminal sequence(s) of the fragment to be amplified. For instance, in the case where a nucleic acid sequence is inferred from protein sequence information a collection of primers containing sequences representing all possible codon variations based on degeneracy of the genetic code will be used for each strand. One primer from this collection will be 100% homologous with the end of the desired sequence to be amplified.

An appropriate agent may be added for inducing or catalyzing the primer extension reaction and the reaction is allowed to occur under conditions known in the art. The inducing agent may be any compound or system which will function to accomplish the synthesis of primer extension products, including enzymes. Suitable enzymes for this purpose may include, for example, E. coli DNA polymerase I, Klenow fragment of E. coli DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis can be initiated at the 3' end of each primer and proceed in the 5' direction along the template strand, until synthesis terminates, producing molecules of different lengths. There may be inducing agents, however, which initiate synthesis at the 5' end and proceed in the other direction, using the same process as described above.

The newly synthesized strand and its complementary nucleic acid strand form a double-stranded molecule which can be used in the succeeding steps of the process. In the next step, the strands of the double-stranded molecule may be separated to provide single-stranded molecules. New nucleic acid may be synthesized on the single-stranded molecules. Additional inducing agent, nucleotides and primers may be added if necessary for the reaction to proceed under the conditions prescribed above. Again, the synthesis would be initiated at one end of the oligonucleotide primers and would proceed along the single strands of the template to produce additional nucleic acid. After this step, half of the extension product would consist of the specific nucleic acid sequence bounded by the two primers. The steps of strand separation and extension product synthesis can be repeated as often as needed to produce the desired quantity of the specific nucleic acid sequence. The amount of the specific nucleic acid sequence produced would accumulate in an exponential fashion. After the appropriate length of time has passed to produce the desired amount of the specific nucleic acid sequence, the reaction may be halted by inactivating the enzymes in any known manner or separating the components of the reaction.

Amplification is useful when the amount of nucleic acid available for analysis is very small, as, for example, in the prenatal diagnosis of sickle cell anemia using DNA obtained from fetal cells. Amplification is particularly useful if such an analysis is to be done on a small sample using non-radioactive detection techniques which may be inherently insensitive, or where radioactive techniques are being employed but where rapid detection is desirable.

Any known techniques for nucleic acid (e.g., DNA and RNA) amplification can be used with the assays described herein. Preferred amplification techniques are the polymerase chain reaction (PCR) methodologies which comprise solution PCR and in situ PCR.

The invention is not limited to the use of straightforward PCR. A system of nested primers may be used for example. Other suitable amplification methods known in the field can also be applied such as, but not limited to, ligase chain reaction (LCR), strand displacement amplification (SDA), self-sustained sequence replication (3SR), array based test, and TAQMAN.

As used herein "amplification" may refer to any in vitro method for increasing the number of copies of a nucleic acid sequence with the use of a DNA polymerase. Nucleic acid amplification results in the incorporation of nucleotides into a DNA molecule or primer thereby forming a new DNA molecule complementary to a DNA template. The newly formed DNA molecule and its template can be used as templates to synthesize additional DNA molecules. As used herein, one amplification reaction may consist of many rounds of DNA replication. DNA amplification reactions include, for example, polymerase chain reactions (PCR). One PCR reaction may consist of 5-100 "cycles" of denaturation, annealing, and synthesis of a DNA molecule.

Fluorescence Microscopy

Some embodiments of the invention include fluorescence microscopy for a detection of a biological substance in a nasal specimen. Fluorescence microscopy enables the molecular composition of the structures being observed to be identified through the use of fluorescently-labeled probes of high chemical specificity such as antibodies. It can be done by directly conjugating a fluorophore to a protein and introducing this back into a cell. Fluorescent analogue may behave like the native protein and can therefore serve to reveal the distribution and behavior of this protein in the cell. Along with NMR, infrared spectroscopy, circular dichroism and other techniques, protein intrinsic fluorescence decay and its associated observation of fluorescence anisotropy, collisional quenching and resonance energy transfer are techniques for protein detection.

The naturally fluorescent proteins can be used as fluorescent probes. The jellyfish aequorea victoria produces a naturally fluorescent protein known as green fluorescent protein (GFP). The fusion of these fluorescent probes to a target protein enables visualization by fluorescence microscopy and quantification by flow cytometry. Without limiting the scope of the present invention, some of the probes are as following:

Labels: Sensitivity and safety (compared to radioactive methods) of fluorescence has led to an increasing use for specific labeling of nucleic acids, proteins and other biomolecules. Besides fluorescein, other fluorescent labels cover the whole range from 400 to 820 nm. By way of example only, some of the labels are, fluorescein and its derivatives, carboxyfluoresceins, rhodamines and their derivatives, atto labels, fluorescent red and fluorescent orange: Cy3/Cy5 alternatives, lanthanide complexes with long lifetimes, long wavelength labels—up to 800 nm, DY cyanine labels, and phycobili proteins.

Conjugates: Antibody conjugates can be generated with specificity for virtually any epitope and are therefore, applicable to imaging a wide range of biomolecules. By way of example only, some of the conjugates are, isothiocyanate conjugates, streptavidin conjugates, and biotin conjugates.

Enzyme Substrates: By way of example only, some of the enzyme substrates are fluorogenic and chromogenic substrates.

Micro- and Nanoparticles: By way of example only, some of the fluorochromes are: FITC (green fluorescence, excitation/emission=506/529 nm), rhodamine B (orange fluorescence, excitation/emission=560/584 nm), and nile blue A (red fluorescence, excitation/emission=636/686 nm). Fluorescent nanoparticles can be used for various types of immunoassays. Fluorescent nanoparticles are based on different materials, such as, polyacrylonitrile, and polystyrene etc.

Molecular Rotors: Fluorescent molecular rotors are sensors of microenvironmental restriction that become fluorescent when their rotation is constrained. Few examples of molecular constraint include increased dye (aggregation), binding to antibodies, or being trapped in the polymerization of actin.

IEF-Markers: IEF (isoelectric focusing) is an analytical tool for the separation of ampholytes, mainly proteins. An advantage for IEF-Gel electrophoresis with fluorescent IEF-marker is the possibility to directly observe the formation of gradient. Fluorescent IEF-marker can also be detected by UV-absorption at 280 nm (20° C.).

Any or all of these fluorescent probes can be used for the detection of biological substances in the nasal mucus. A peptide library can be synthesized on solid supports and, by using coloring receptors, subsequent dyed solid supports can be selected one by one. If receptors cannot indicate any color, their binding antibodies can be dyed. The method can not only be used on protein receptors, but also on screening binding ligands of synthesized artificial receptors and screening new metal binding ligands as well. Automated methods for HTS and FACS (fluorescence activated cell sorter) can also be used. A FACS machine originally runs cells through a capillary tube and separate cells by detecting their fluorescent intensities.

Immunoassays

Some embodiments of the invention include immunoassay for a detection of a biological substance in a nasal specimen. In immunoblotting like the western blot of electrophoretically separated proteins a single protein can be identified by its antibody. Immunoassay can be competitive binding immunoassay where analyte competes with a labeled antigen for a limited pool of antibody molecules (e.g. radioimmunoassay, EMIT) Immunoassay can be non-competitive where antibody is present in excess and is labeled. As analyte antigen complex is increased, the amount of labeled antibody-antigen complex may also increase (e.g. ELISA). Antibodies can be polyclonal if produced by antigen injection into an experimental animal, or monoclonal if produced by cell fusion and cell culture techniques. In immunoassay, the antibody may serve as a specific reagent for the analyte antigen.

Without limiting the scope and content of the present invention, some of the types of immunoassays are, by way of example only, RIAs (radioimmunoassay), enzyme immunoassays like ELISA (enzyme-linked immunosorbent assay), EMIT (enzyme multiplied immunoassay technique), microparticle enzyme immunoassay (MEIA), LIA (luminescent immunoassay), and FIA (fluorescent immunoassay). These techniques can be used to detect biological substances in the nasal specimen. The antibodies—either used as primary or secondary ones—can be labeled with radioisotopes (e.g. 125I), fluorescent dyes (e.g. FITC) or enzymes (e.g. HRP or AP) which may catalyse fluorogenic or luminogenic reactions.

EMIT (Enzyme Multiplied Immunoassay Technique): EMIT is a competitive binding immunoassay that avoids the usual separation step. A type of immunoassay in which the protein is labeled with an enzyme, and the enzyme-protein-antibody complex is enzymatically inactive, allowing quantitation of unlabelled protein.

ELISA (Enzyme Linked Immunosorbent Assay): Some embodiments of the invention include ELISA to detect biological substances in the nasal specimen. ELISA is based on selective antibodies attached to solid supports combined with enzyme reactions to produce systems capable of detecting low levels of proteins. It is also known as enzyme immunoassay or EIA. The protein is detected by antibodies that have been made against it, that is, for which it is the antigen. Monoclonal antibodies are often used.

The test may require the antibodies to be fixed to a solid surface, such as the inner surface of a test tube, and a preparation of the same antibodies coupled to an enzyme. The enzyme may be one (e.g., β-galactosidase) that produces a colored product from a colorless substrate. The test, for example, may be performed by filling the tube with the antigen solution (e.g., protein) to be assayed. Any antigen molecules present may bind to the immobilized antibody molecules. The antibody-enzyme conjugate may be added to the reaction mixture. The antibody part of the conjugate binds to any antigen molecules that were bound previously, creating an antibody-antigen-antibody "sandwich". After washing away any unbound conjugate, the substrate solution may be added. After a set interval, the reaction is stopped (e.g., by adding 1 N NaOH) and the concentration of colored product formed is measured in a spectrophotometer. The intensity of color is proportional to the concentration of bound antigen.

ELISA can also be adapted to measure the concentration of antibodies, in which case, the wells are coated with the appropriate antigen. The solution (e.g., serum) containing antibody may be added. After it has had time to bind to the immobilized antigen, an enzyme-conjugated anti-immunoglobulin may be added, consisting of an antibody against the antibodies being tested for. After washing away unreacted reagent, the substrate may be added. The intensity of the color produced is proportional to the amount of enzyme-labeled antibodies bound (and thus to the concentration of the antibodies being assayed).

Radioimmunoassay: Some embodiments of the invention include radioimmunoassays to detect biological substances in the nasal specimen. Radioactive isotopes can be used to study in vivo metabolism, distribution, and binding of small amount of compounds. Radioactive isotopes of $^{1}H$, $^{12}C$, $^{31}P$, $^{32}S$ and $^{127}I$ in body are used such as $^{3}H$, $^{14}C$, $^{32}P$, $^{35}S$, and $^{125}I$.

In receptor fixation method in 96 well plates, receptors may be fixed in each well by using antibody or chemical methods and radioactive labeled ligands may be added to each well to induce binding. Unbound ligands may be washed out and then the standard can be determined by quantitative analysis of radioactivity of bound ligands or that of washed-out ligands. Then, addition of screening target compounds may induce competitive binding reaction with receptors. If the compounds show higher affinity to receptors than standard radioactive ligands, most of radioactive ligands would not bind to receptors and may be left in solution. Therefore, by analyzing quantity of bound radioactive ligands (or washed-out ligands), testing compounds' affinity to receptors can be indicated.

The filter membrane method may be needed when receptors cannot be fixed to 96 well plates or when ligand binding needs to be done in solution phase. In other words, after ligand-receptor binding reaction in solution, if the reaction solution is filtered through nitrocellulose filter paper, small molecules including ligands may go through it and only protein receptors may be left on the paper. Only ligands that strongly bound to receptors may stay on the filter paper and the relative affinity of added compounds can be identified by quantitative analysis of the standard radioactive ligands.

Fluorescence Immunoassays: Some embodiments of the invention include fluorescence immunoassays for a detection of a biological substance in a nasal specimen. Fluorescence based immunological methods are based upon the competitive binding of labeled ligands versus unlabeled ones on highly specific receptor sites.

The fluorescence technique can be used for immunoassays based on changes in fluorescence lifetime with changing analyte concentration. This technique may work with short lifetime dyes like fluorescein isothiocyanate (FITC) (the donor) whose fluorescence may be quenched by energy transfer to eosin (the acceptor). A number of photoluminescent compounds may be used, such as cyanines, oxazines, thiazines, porphyrins, phthalocyanines, fluorescent infrared-emitting polynuclear aromatic hydrocarbons, phycobiliproteins, squaraines and organo-metallic complexes, hydrocarbons and azo dyes.

Fluorescence based immunological methods can be, for example, heterogenous or homogenous. Heterogenous immunoassays comprise physical separation of bound from free labeled analyte. The analyte or antibody may be attached to a solid surface. The technique can be competitive (for a higher selectivity) or noncompetitive (for a higher sensitivity). Detection can be direct (only one type of antibody used) or indirect (a second type of antibody is used). Homogenous immunoassays comprise no physical separation. Double-antibody fluorophore-labeled antigen participates in an equilibrium reaction with antibodies directed against both the antigen and the fluorophore. Labeled and unlabeled antigen may compete for a limited number of anti-antigen antibodies.

Some of the fluorescence immunoassay methods include simple fluorescence labeling method, fluorescence resonance energy transfer (FRET), time resolved fluorescence (TRF), and scanning probe microscopy (SPM). The simple fluorescence labeling method can be used for receptor-ligand binding, enzymatic activity by using pertinent fluorescence, and as a fluorescent indicator of various in vivo physiological changes such as pH, ion concentration, and electric pressure. TRF is a method that selectively measures fluorescence of the lanthanide series after the emission of other fluorescent molecules is finished. TRF can be used with FRET and the lanthanide series can become donors or acceptors. In scanning probe microscopy, in the capture phase, for example, at least one monoclonal antibody is adhered to a solid phase and a scanning probe microscope is utilized to detect antigen/antibody complexes which may be present on the surface of the solid phase. The use of scanning tunneling microscopy eliminates the need for labels which normally is utilized in many immunoassay systems to detect antigen/antibody complexes.

Nuclear Magnetic Resonanace (NMR)

Some embodiments of the invention include NMR for detection of a biological substance in a nasal specimen. NMR spectroscopy is capable of determining the structures of biological macromolecules like proteins and nucleic acids at atomic resolution. In addition, it is possible to study time dependent phenomena with NMR, such as intramolecular dynamics in macromolecules, reaction kinetics, molecular recognition or protein folding. Heteronuclei like $^{15}N$, $^{13}C$ and $^{2}H$, can be incorporated in proteins by uniform or selective isotopic labeling. Additionally, some new information about structure and dynamics of macromolecules can be determined with these methods.

X-Ray Crystallography

Some embodiments of the invention include X-ray crystallography for detection of a biological substance in a nasal specimen. X-ray crystallography is a technique in which the pattern produced by the diffraction of X-rays through the closely spaced lattice of atoms in a crystal is recorded and then analyzed to reveal the nature of that lattice. This generally leads to an understanding of the material and molecular structure of a substance. The spacings in the crystal lattice can be determined using Bragg's law. X-ray diffraction is commonly carried out using single crystals of a material, but if these are not available, microcrystalline powdered samples may also be used which may require different equipment.

Fluorescence Spectroscopy

Some embodiments of the invention include fluorescence spectroscopy for detection of a biological substance in a nasal specimen. By way of example only, conventional fluorometry is measurement of emission light intensities at defined wavelengths for a certain emission maxima of a fluorophore. Total fluorometry is a collection of data for a continuum of absorption as well as emission wavelengths. Fluorescence polarization is when polarized light is used for excitation and binding of fluorochrome-labeled antigens to specific antibodies. Line narrowing spectroscopy is low-temperature solid-state spectroscopy that derives its selectivity from the narrow-line emission spectra.

Time-dependent fluorescence spectroscopy comprises time-resolved measurements containing more information than steady-state measurements, since the steady-state values represent the time average of time-resolved determinations. It is a single photon timing technique where the time between an excitation light pulse and the first photon emitted by the sample is measured.

Matrix Assisted Laser Desorption Ionization Time-of-Flight Mass Spectrometry (MALDI TOF-MS)

Some embodiments of the invention include MALDI TOF-MS for detection of a biological substance in a nasal specimen. MALDI TOF-MS provides accurate mass determinations and primary sequence information. Improved mass resolution in MALDI TOF-MS can be obtained by the utilization of a single-stage or a dual-stage reflectron (RETOF-MS). In the reflectron mass spectrum, the isotopic multiplet is well resolved producing a full width half maximum (FWHM) mass resolution of about 3400. Mass resolutions up to 6000 (FWHM) can be obtained for peptides up to about 3000 Da with RETOF-MS Enhancing the mass resolution can also increase the mass accuracy when determining the ion's mass.

Both linear and reflectron MALDI-TOF-MS can be utilized for molecular weight determinations of molecular ions and enzymatic digests leading to structural information of proteins. These digests are typically mass analyzed with or without purification prior to molecular weight determinations. Varieties of methodologies have been developed to obtain primary sequence information for proteins and peptides utilizing MALDI TOF-MS. Two different approaches can be taken. The first method is known as protein ladder sequencing and can be employed to produce structurally informative fragments of the analyte prior to insertion into the TOF mass spectrometer and subsequent analysis. The second approach utilizes the phenomenon of metastable ion decay that occurs inside the TOF mass spectrometer to produce sequence information.

The ladder sequencing with TOF-MS consists of either a time-dependent or concentration-dependent chemical degradation from either the N- or C-terminus of the protein/peptide into fragments, each of which differs by one amino acid residue. The mixture is mass analyzed in a single MALDI-TOF-MS experiment with mass differences between adjacent mass spectral peaks corresponding to a specific amino acid residue. The order of occurrence in the mass spectrum defines the sequence of amino acids in the original protein/peptide.

Post-source decay with RETOF-MS MALDI is an ionization technique that produces intact protonated pseudomolecular ion species. A significant degree of metastable ion decay occurs after ion acceleration and prior to detection. The ion fragments produced from the metastable ion decay of peptides and proteins typically include both neutral molecule losses (such as water, ammonia and portions of the amino acid side chains) and random cleavage at peptide bonds. In-source decay with linear TOF-MS is an alternative approach to RETOF-MS for studying metastable ion decay of MALDI generated ions. Primary structural information for peptides and proteins can be obtained by this method. Coherent mass spectral peaks can be produced from these metastable decayed ions giving rise to significant structural information for peptides and proteins.

Surface-Enhanced Laser Desorption Ionization-Time of Flight (SELDI-TOF)

Some embodiments of the invention include SELDI TOF-MS for detection of a biological substance in a nasal specimen. This technique utilizes stainless steel or aluminum-based supports, or chips, engineered with chemical (hydrophilic, hydrophobic, pre-activated, normal-phase, immobilized metal affinity, and cationic or anionic) or biological (antibody, antigen binding fragments (e.g. scFv), DNA, enzyme, or receptor) bait surfaces of 1-2 mm in diameter. These varied chemical and biochemical surfaces allow differential capture of proteins based on the intrinsic properties of the proteins themselves. Solubilized tissue or body fluids in volumes as small as 0.1 µl can be directly applied to these surfaces, where proteins with affinities to the bait surface may bind. Following a series of washes to remove nonspecifically or weakly bound proteins, the bound proteins are laser desorbed and ionized for MS analysis. Masses of proteins ranging from small peptides of less than 1000 Da up to proteins of greater than 300 kDa can be calculated based on time-of-flight. As mixtures of proteins may be analyzed within different samples, a unique sample fingerprint or signature may result for each sample tested. Consequently, patterns of masses rather than actual protein identifications can be produced by SELDI analysis. These mass spectral patterns can be used to differentiate patient samples from one another, such as diseased from normal.

UV-Vis

Some embodiments of the invention include optical absorption spectroscopy (UV/VIS) for detection of a biological substance in a nasal specimen. UV/VIS provides light absorption data which helps in the determination of concentration of macromolecules such as, proteins, DNA, nucleotides etc. Organic dyes can be used to enhance the absorption and to shift the absorption into the visible range (e.g. coomassie blue reagents). Resonance raman spectroscopy (RRS) can be used to study molecular structure and dynamics. RRS helps in investigating specific parts of macromolecules by using different excitation wavelengths.

Liquid Chromatography (LC)

Some embodiments of the invention include LC for a detection of biological substance in a nasal specimen. Examples of LC are but not limited to, affinity chromatography, gel filtration chromatography, anion exchange chromatography, cation exchange chromatography, diode array-LC and high performance liquid chromatography (HPLC).

Gel filtration chromatography separates proteins, peptides, and oligonucleotides on the basis of size. Molecules may move through a bed of porous beads, diffusing into the beads to greater or lesser degrees. Smaller molecules may diffuse further into the pores of the beads and therefore move through the bed more slowly, while larger molecules may enter less or not at all and thus move through the bed more quickly. Both molecular weight and three dimensional shapes contribute to the degree of retention. Gel filtration chromatography may be used for analysis of molecular size, for separations of components in a mixture, or for salt removal or buffer exchange from a preparation of macromolecules.

Affinity chromatography is the process of bioselective adsorption and subsequent recovery of a compound from an immobilized ligand. This process allows for the specific and efficient purification of many diverse proteins and other compounds. Ion exchange chromatography separates molecules based on differences between the overall charges of the proteins. It can be used for the purification of protein, oligonucleotides, peptides, or other charged molecules.

HPLC can be used in the separation, purification and detection of biological substances in the nasal mucus. Crude tissue extracts may be loaded directly onto the HPLC system and mobilized by gradient elution. Rechromatography under the identical conditions is an option if further purification is warranted or necessary. Reversed phase chromatography (RPC) can be utilized in the process of protein structure determination. HPLC may be coupled with MS. The HPLC method described in Henkin et al., New Frontiers in Immunobiology, 2000, pp. 127-152, is incorporated herein in its entirety.

Size-exclusion chromatography (SEC) and ion-exchange chromatography (IEC) can be used for separation and purification of biologically active proteins, such as enzymes, hormones, and antibodies. In liquid affinity chromatography (LAC), interaction may be based on binding of the protein due to mimicry of substrate, receptor, etc. The protein may be eluted by introducing a competitive binding agent or altering the protein configuration which may facilitate dissociation. A procedure that can be used in the separation of membrane proteins is the use of nonionic detergents, such as Triton X-100, or protein solubilization by organic solvents with IEC.

Diode array detector-liquid chromatography (DAD-LC) provides complete, multiple spectra for each HPLC peak, which, by comparison, can provide indication of peak purity. These data can also assign presence of tyr, trp, phe, and possibly others (his, met, cys) and can quantitate these amino acids by 2nd derivative or multi-component analysis. By a post-column derivatization, DAD-LC can also identify and quantitate cys, his and arg in individual peptides. Thus, it is possible to analyze for 6 of the 20 amino acids of each separated peptide in a single LC run, and information can be obtained about presence or absence of these amino acids in a given peptide in a single step. This is assisted by knowing the number of residues in each peptide.

Electrophoresis

Some embodiments of the invention include electrophoresis for detection of a biological substance in a nasal specimen. Electrophoresis can be gel electrophoresis or capillary electrophoresis.

Gel Electrophoresis: Gel electrophoresis is a technique that can be used for the separation of proteins. During electrophoresis, macromolecules are forced to move through pores when an electrical current is applied. Their rate of migration through the electric field depends on strength of the field, size and shape of the molecules, relative hydrophobicity of the samples, and on an ionic strength and temperature of a buffer in which the molecules are moving. After staining, the separated macromolecules in each lane can be seen in a series of bands spread from one end of the gel to the other. Using this technology it is possible to separate and identify protein molecules that differ by as little as a single amino acid. Also, gel electrophoresis allows determination of crucial properties of a protein such as its isoelectric point and approximate molecular weight. Electrofocusing or isoelectric focusing is a technique for separating different molecules by their electric charge differences (if they have any charge). It is a type of zone electrophoresis that takes advantage of the fact that a molecule's charge changes as the pH of its surroundings changes.

Capillary Electrophoresis: Capillary electrophoresis is a collection of a range of separation techniques which may involve the application of high voltages across buffer filled capillaries to achieve separations. The variations include separation based on size and charge differences between analytes (termed capillary zone electrophoresis (CZE) or free solution CE (FSCE)), separation of neutral compounds using surfactant micelles (micellar electrokinetic capillary chromatography (MECC) or sometimes referred to as MEKC) sieving of solutes through a gel network (capillary gel electrophoresis, GCE), separation of cations (or anions) based on electrophoretic mobility (capillary isotachophoresis, CITP), and separation of zwitterionic solutes within a pH gradient (capillary isoelectric focusing, CIEF). Capillary electrochromatography (CEC) can be an associated electrokinetic separation technique which involves applying voltages across capillaries filled with silica gel stationary phases. Separation selectivity in CEC can be a combination of both electrophoretic and chromatographic processes. Many of the CE separation techniques rely on the presence of an electrically induced flow of solution (electroosmotic flow, EOF) within the capillary to pump solutes towards the detector.

Arrays

Some embodiments of the invention include arrays for detection of a biological substance in a nasal specimen. Arrays involve performing parallel analysis of multiple samples against known protein targets. The development of various microarray platforms can enable and accelerate the determination of protein abundance, localization, and interactions in a cell or tissue. Microarrays provide a platform that allows identification of protein interaction or function against a characterized set of proteins, antibodies, or peptides. Protein-based chips array proteins on a small surface and can directly measure the levels of proteins in tissues using fluorescence-based imaging. Proteins can be arrayed on either flat solid phases or in capillary systems (microfluidic arrays), and several different proteins can be applied to these arrays. In addition to the use of antibodies as array probes, single-stranded oligonucleotides, whose specificity is optimized by in vitro elution (aptamers), offer a viable alternative. Nonspecific protein stains can be then used to detect bound proteins.

Arrays include, but are not limited to, bead arrays, bead based arrays, bioarrays, bioelectronic arrays, cDNA arrays, cell arrays, DNA arrays, gene arrays, gene expression arrays, frozen cell arrays, genome arrays, high density oligonucleotide arrays, hybridization arrays, microcantilever arrays, microelectronic arrays, multiplex DNA hybridization arrays, nanoarrays, oligonucleotide arrays, oligosaccharide arrays, planar arrays, protein arrays, solution arrays, spotted arrays, tissue arrays, exon arrays, filter arrays, microarrays, small molecule microarrays, suspension arrays, theme arrays, tiling arrays, and transcript arrays.

Sensors

Some embodiments of the invention include sensors for detection of a biological substance in a nasal specimen. Sensors can be used for both in vivo and in vitro detection. Sensors can be chemical sensors, optical sensors, and biosensors. Chemical sensors are miniaturized analytical devices which may deliver real-time and online information on the presence of specific compounds or ions in complex samples. Optical sensors are based on measurement of either intrinsic optical properties of analytes, or of optical properties of indicator dyes or labeled biomolecules attached to solid supports. Biosensors can be affinity biosensor based on capabilities of enzymes to convert substrates into products or catalytic biosensors. Biosensors detect antibody and analyte complexes using a variety of physical methods. Some biosensors measure the change in surface charge that occurs when analyte is bound to antibodies or other binding agents, which in turn are bound to a surface. Other biosensors use binding agents attached to a surface and measure a change in a physical property of the support, other than surface charge, upon binding of analyte. Some biosensor techniques use a specific property of a labeled binding agent or antigen to produce a measurable change.

Methods for Identifying Proteins from a Library Screen

Protein identification methods by way of example only include low-throughput sequencing through Edman degradation, mass spectrometry techniques, peptide mass fingerprinting, de novo sequencing, and antibody-based assays. The protein quantification assays include fluorescent dye gel staining, tagging or chemical modification methods (i.e. isotope-coded affinity tags (ICATS), combined fractional diagonal chromatography (COFRADIC)). The purified protein may also be used for determination of three-dimensional crystal structure, which can be used for modeling intermolecular interactions. Common methods for determining three-dimensional crystal structure include x-ray crystallography and NMR spectroscopy. Detailed below are a few of the methods for identifying proteins in the present invention.

Protein sequencing: N-terminal sequencing aids in the identification of unknown proteins, confirms recombinant protein identity and fidelity (reading frame, translation start point, etc.), aids the interpretation of NMR and crystallographic data, demonstrates degrees of identity between proteins, or provide data for the design of synthetic peptides for antibody generation, etc. N-terminal sequencing utilises the Edman degradative chemistry, sequentially removing amino acid residues from the N-terminus of the protein and identifying them by reverse-phase HPLC. Sensitivity can be at the level of 100s femtomoles and long sequence reads (20-40 residues) can often be obtained from a few 10s picomoles of starting material. Pure proteins (>90%) can generate easily interpreted data, but insufficiently purified protein mixtures may also provide useful data, subject to rigorous data interpretation. N-terminally modified (especially acetylated) proteins cannot be sequenced directly, as the absence of a free primary amino-group prevents the Edman chemistry. However, limited proteolysis of the blocked protein (e.g. using cyanogen bromide) may allow a mixture of amino acids to be generated in each cycle of the instrument, which can be subjected to database analysis in order to interpret meaningful sequence information. C-terminal sequencing is a post-translational modification, affecting the structure and activity of a protein. Various disease situations can be associated with impaired protein processing and C-terminal sequencing provides an additional tool for the investigation of protein structure and processing mechanisms.

Proteome analyses: Proteomics can be identified primarily by computer search algorithms that assign sequences to a set of empirically acquired mass/intensity data which are generated from conducting electrospray ionization (ESI), matrix-assisted laser desorption/ionization (MALDI-TOF), or three-dimensional quadrupole ion traps on the protein of interest.

Diagnosis

The identification and analysis of biological substances as disclosed herein has numerous therapeutic and diagnostic applications. Clinical applications include, for example, detection of disease, distinguishing disease states to inform prognosis, selection of therapy, and/or prediction of therapeutic response, disease staging, identification of disease processes, prediction of efficacy of therapy, monitoring of patients trajectories (e.g., prior to onset of disease), prediction of adverse response, monitoring of therapy associated with efficacy and toxicity, and detection of recurrence.

Measuring a concentration of the biological substance can aid in the diagnosis of a course of a disease. For example, the diabetic state of a patient who was previously diagnosed with diabetes can be determined by monitoring the nasal secretions of the patient for insulin. A biological substance, for example, growth factor may be one that is specific for the patient's specific disease. Alternatively, a panel of two or more specific or non-specific growth factors may be monitored. The concentrations of either an individual factor or several factors, in the biological sample of the patient may be affected by the disease.

The presence or increase or decrease of biological substances' concentration allows the physician or veterinarian to predict the course of the disease or the efficacy of treatment regimes. If, for example, a patient who had a certain type of disease, which was treated, subsequently exhibits an increase in the concentration of biological substances that is associated with that disease, the physician or veterinarian can predict that the patient may have progression of the disease in the future or predict a higher risk of fatality in the patient. In addition, the amount of biological substances may be predictive of the outcome of the patient, e.g., how well certain chemotherapeutic agents may act.

One aspect of the present invention is a method of diagnosing a disease by obtaining a specimen of nasal secretion, detecting a biological substance in the specimen, and diagnosing the disease wherein the diagnosis is based on the detection of the biological substance, and wherein the biological substance is not related to a respiratory disease. In one embodiment leprosy is diagnosed by detection of antibodies against leprosy causing pathogen for example, *mycobacterium leprae*. In one embodiment hepatitis, such as hepatitis A, B, C, D, E, and G, is diagnosed by detection of antibodies against hepatitis causing virus. In some embodiments, the biological substances include insulin or insulin receptors for a diagnosis of diabetes. In some embodiments, the biological substance is p53 for a diagnosis of cancer.

Some embodiments of the invention include diagnosing diabetes by detecting insulin or insulin receptor in the nasal specimen. Table 6 depicts detection and measurement of human insulin concentration in nasal mucus as compared to insulin concentration in blood plasma and saliva. Table 7 depicts the detection and measurement of human insulin receptor concentration in nasal mucus as compared to the insulin receptor concentration in plasma and saliva. The appearance of insulin or insulin receptors in nasal mucus refects either their synthesis in nasal serous glands or response to a physiological and/or pathological phenomena. The presence of insulin or insulin receptors in nasal mucus offers a non-invasive method for the diagnosis of diabetes and other disorders of carbohydrate metabolism.

Some embodiments of the invention include diagnosing cancer by detecting caspase in the nasal specimen. Cysteine-dependent aspartate-specific proteases (caspases) are a family of proteases that cleave their substrates at aspartic acid (D)-X bonds. 14 mammalian caspases have been identified. Caspase-2, -3, -6, -7, -8, -9 and -10 are major players in the execution phase of apoptosis, whereas caspase-1, -4, -5, and -11 are involved in cytokine processing associated with inflammation. Caspase 3, also known as CPP32, cleaves and activates a variety of proteins such as sterol regulatory element binding proteins (SREBPs). Caspase-3 also cleaves poly (ADP-ribose) polymerase (PARP) at the onset of apoptosis and amyloid β precursory protein (APP) which is associated with neuronal death in Alzheimer's disease. Caspase 3 is activated by graszyne β, ADAF-1, caspase 9 and caspases 6, 8 and 10. This substance is one of the apoptotic substances found during the apoptotic process. Table 10 illustrates a comparison between the detection of caspase 3 in nasal mucus as well as saliva. The presence of caspase in nasal mucus is about 13% of that in saliva and reflects the magnitude of the apoptotic process. The presence of caspase in nasal mucus indicates the activity of cellular death in nasal mucus and shows that cancer can be diagnosed by detecting caspase in the nasal specimen.

Some embodiments of the invention include diagnosing cancer, taste loss or smell loss by detecting tumor necrosis factor α (TNFα) in the nasal specimen. TNFα is a 17 KD cleavage product mediated by TNFα converting enzyme which interacts with two distinct TNFα receptors (I, II) on the cell surface. TNFα is upregulated in many pathological processes involving inflammation and oncological processes such as rheumatoid arthritis, refractory bronchial asthma, liver disease, cancer and in patients with taste and smell loss. It is also called cachectin and is produced by many normal and tumor cells in response to a wide variety of stimuli including viruses, bacteria, parasites, cytokines and mitogens. Both the transmembrane and the soluble secreted forms of TNFα are biologically active. TNFα is an extremely pleotropic cytokine due to the ubiquity of its receptors, its ability to activate multiple signal transduction pathways and its ability to induce or suppress the expression a large number of genes.

Detecting the levels of TNFα in nasal mucus as disclosed herein makes the diagnosis of a disease possible on a clinical basis since obtaining cellular diagnosis through tissue biopsy can not only be invasive but also can be difficult and at times dangerous. Table 11 illustrates detection and measurement of TNFα in nasal mucus and saliva in 75 subjects. Results indicate that TNFα in nasal mucus is about 30 times higher than in saliva. These data suggest that various cancers can be diagnosed by measurements of TNFα in nasal mucus and their treatment can be monitored by following its concentration in nasal mucus. Since levels of TNFα may also reflect the inflammatory aspects of disease processes inducing it, use of anti TNFα drugs through nasal administration reflect a method of treating these various disease processes. Concentrations of TNFα in nasal mucus in patients with smell loss can be greater than for example, 5000 times that found in normal subjects thereby reflecting its function as a "death protein" indicator of excessive apoptosis as in its role in cancer.

Monitoring the levels of TNFα in nasal mucus may help in diagnosis of arterial venous malfunction (AVM). AVM is normally diagnosed by MRI but detection and measurement of TNFα in nasal mucus provides a non-invasive method of diagnosing AVM. Monitoring the level of TNFα can help in diagnosing the progression or stage of AVM or the susceptibility of the subject towards AVM.

Some embodiments of the invention include diagnosing cancer, taste loss or smell loss by detecting tumor necrosis factor receptor I (TNFR I) in the nasal specimen. TNF receptor I (TNFRI) is one of the two cellular receptors upon which TNFα operates. It is one of the prototypic members of the TNF receptor super family members designated TNFRSF I α. In disease processes associated with increased TNFα activity TNFR I may be upregulated. Its presence in nasal mucus can reflect the activity of many inflammatory, oncological and other pathological processes, including taste and smell dysfunction. Table 12 illustrates detection and measurement of TNFR I in 47 subjects. Results indicate that TNFR I in nasal mucus is about 16 times its concentration in saliva and its concentration is significantly increased over that found in plasma, red blood cells, or urine. Thus the detection of TNFR I in the nasal specimen can be used to establish clinical diagnoses of excessive apoptosis and can be used as a treatment modality in inhibiting pathological apoptosis.

TNFR II is the other of the two cellular receptors upon which TNFα operates. TNFR II is one of the high-affinity receptors for TNFα and is one of the prototypic members of the TNF super family members designated TNFSF I β. TNFR II may be upregulated in many inflammatory and oncological disease processes. It may also be solubilized and have properties similar to TNFR I. Table 13 illustrates detection and measurement of TNFR II in 47 subjects. Results indicate that TNFR II in nasal mucus is about 24 times its concentration in saliva and its concentration in nasal mucus is significantly higher than found in plasma, rbcs, or urine. The results reflect that detection of TNFR II in nasal specimen can provide a non invasive method of diagnosing various pathological processes related to TNFR II.

TNF related apoptosis-inducing ligand (TRAIL) is also known as apo-2 ligand and TNFSF-10. It is a Type II transmembrane protein with a carboxy terminal extracellular domain that exhibits homology to other TNF super family members. Among TNF super family members TRAIL is the most homologous Fas ligand, sharing 28% amino acid sequence identity in their extracellular domain. Human TRAIL shares 65% amino acid sequence identity with mouse TRAIL. TRAIL reflects the terminal protein in the apoptotic sequence. Table 14 in the examples illustrates detection and measurement of TRAIL in saliva and nasal mucus in normal subjects and in patients with smell loss. Results indicate that TRAIL in nasal mucus is about 5 times higher than in saliva and both are significantly higher than in blood, rbcs or urine. The results reflect that detection of TRAIL in nasal mucus can provide a non invasive method of diagnosing various diseases related to TRAIL. The methods of the present invention include treatment of diseases by modulating these elevated concentrations by use of anti-TRAIL drugs or agents. In some embodiments, the treatment is preferably by nasal administration.

Some embodiments of the invention include diagnosing disease by detecting interleukin in the nasal specimen. Interleukin 2 (IL2) is a T-cell growth factor that is produced by T-cells following activation by mitogins or antigens and it stimulate growth and differentiation of β cells, natural killer (NK) cells, lymphocyte killer (LAK) cells, monocytes/macrophages and oligodendrocytes. At the amino acid sequence level there can be about 50-90% homology between species. Interleukin 3 (IL 3), also known as mast cell growth factor, is a pleitropic factor produced primarily by activated T cells. It can stimulate proliferation and differentiation of pluripotent hematopoetic stem cells as well as various lineage committed progenitors. Mature human and mouse IL 3 share about 29% amino acid sequence homology. Table 18 in the examples illustrates detection and measurement of IL 3 in both human saliva and nasal mucus. Levels of IL 3 in nasal mucus were found to be about ½ A the concentration in saliva but both levels were higher than that found in plasma, rbcs or urine. IL 3 present in nasal mucus provides a non invasive method of diagnosing various diseases related to IL3. The methods of the present invention include treatment of diseases by modulating the concentration of IL3 with drugs. In some embodiments, the treatment is by nasal administration.

Some embodiments of the invention include diagnosing disease by detecting endostatin in the nasal specimen. Endostatin is a 20 KD G terminal fragment of collagen XVII. Its function is as an antiangiogenic substance or angiogenic antagonist. It is a naturally occurring protein which has been used as an anti-cancer agent to inhibit blood vessel growth and spread of any form of cancer. Table 19 in the examples illustrates detection and measurement of endostatin in plasma, urine, saliva and nasal mucus in 15 subjects. Endostatin levels in nasal mucus were 5 times higher than in saliva but 7% that found in plasma. On the basis of endostatin/protein, levels of nasal mucus are about 14% that found in plasma. Presence of endostatin in nasal mucus indicates a non-invasive method of detection of endostatin in nasal mucus and its use in diagnosing various diseases. The methods of the present invention include treatment of diseases by modulating the concentration of endostatin with drugs. In some embodiments, the treatment is by nasal administration.

Some embodiments of the invention include diagnosing disease by detecting erythropoietin in the nasal specimen. Erythropoietin (EPO) is a 30 KD glycosylated protein produced primarily by the kidney. It is the principal factor that regulates erythropoesis. Production of EPO by the kidney cell is increased in response to hyposmia or anemia. The cDNA for EPO has been cloned from many species. Mature proteins from various species are highly conserved exhibiting greater than 80% amino acid sequence homology. Table 20 in the examples illustrates detection and measurement of EPO in plasma, urine, saliva and nasal mucus. EPO was not found in urine or saliva. The level of EPO in nasal mucus was found to be between 1.1 and 4.5 times higher than in plasma. Presence of EPO in nasal mucus illustrates a non-invasive method of detection of EPO in nasal mucus and its use in diagnosing various diseases. The diagnosis can further lead to treatment of disease by modulating the concentration of EPO with drugs. In some embodiments, the treatment is by nasal administration.

Some embodiments of the invention include diagnosing disease by detecting bone morphogenic protein in the nasal specimen. Bone morphogenic protein BMP I, also known as procollagen C-proteinase (PCP) is a zinc protease of the astacin family. BMP I/PCP plays a key role in formation of extracellular matrix (KCM) by connecting precursor proteins into their mature and functional form. Precursor proteins identified as substrates for BMP I/PCP include collagens, biglycan, laminin S, dentin matrix protein I and lysyl oxidase. Table 21 in the examples illustrates detection and measurement of BMP I in plasma, urine, saliva and nasal mucus in 20 subjects. BMP I was found in plasma but not in urine, saliva or nasal mucus.

Some embodiments of the invention include diagnosing disease by detecting brain-derived neurotrophic factor in the nasal specimen. Brain-derived neurotrophic factor (BDNF) is a member of the NGF family of neurotrophic factors, BDNF, NGF, NT-3 and NT 4/5. BDNF is required for differentiation and survival of specific subpopulations in both central and peripheral nervous systems. High levels of BDNF expression have been found in hippocampus, cerebellum, fetal eye and placenta. Table 22 in the examples illustrates detection and measurement of BDNF in plasma, urine, saliva and nasal mucus in 20 subjects. BDNF was found in plasma and nasal mucus but not in urine or saliva. Levels of BDNF in plasma were higher than in nasal mucus. The results indicate that nasal mucus is a repository of the family of nerve growth factors and the concentration of BDNF as shown in Table 22, may help understand both physiology and pathology of neurotrophic factors related to growth and homeostasis of cells in the nasal cavity as well as reporting on the presence of these factors in the systemic circulation. Presence of BDNF in nasal mucus illustrates a non-invasive method of detection of BDNF in nasal mucus and its use in diagnosing various diseases. The diagnosis can further lead to treatment of diseases by modulating the concentration of BDNF with drugs. In some embodiments, the treatment is by nasal administration.

Some embodiments of the invention include diagnosing disease by detecting ciliary neurotrophic factor in the nasal specimen. Ciliary neurotrophic factor (CNTF) is structurally related to IL-6, IL-11, L1F, CLC and OSM. CNTF is a trophic factor for embryonic chick ciliary parasympathetic neurons in culture. CNTF is also a survival factor for additional numerous cell types including dorsal root ganglion sensory neurons, sympathetic ganglion neurons, embryonic motor neurons, major pelvic ganglion neurons and hippocampal neurons. Table 23 in the examples illustrates detection and measurement of CNTF in plasma, urine, saliva and nasal mucus in 19 subjects. Levels of CNTF in plasma and nasal mucus were found to be similar but lower in saliva. Presence of CNTF in nasal mucus illustrates a non-invasive method of detection of CNTF in nasal mucus and its use in diagnosing various diseases. The diagnosis can further lead to treatment of diseases by modulating the concentration of CTNF with drugs. In some embodiments, the treatment is by nasal administration.

Some embodiments of the invention include diagnosing disease by detecting granulocyte macrophage growth factor in the nasal specimen. Granulocyte macrophage growth factor (GM-CSF) is a 22 KD mononeric hematopoetic cytokine that is characterized as a growth factor that supports the in vitro colony formation of granulocyte macrophage progenitors. It is produced by a number of different cell types including activated T cells, B cells, macrophages, mast cells, endothelial cells and fibroblasts, in response to cytokines or immune and inflammatory stimuli. GM-CSF is species specific. Table 24 in the examples illustrates detection and measurement of GM-CSF in plasma, urine, saliva and nasal mucus in 16 subjects. The results provide a non-invasive method for the detection of GM-CSF in nasal mucus. Levels in nasal mucus were found to be over 6 times that found in plasma. The detection of GM-CSF in nasal mucus provides a non invasive method of diagnosing various diseases related to GM-CTF. The methods of the present invention include treatment of diseases by modulating the concentrations of GM-CSF by use of drugs. In some embodiments, the treatment is by nasal administration.

Some embodiments of the invention include diagnosing disease by detecting hepatocyte growth factor in the nasal specimen. Hepatocyte growth factor (HGF), also known as hepatopoeitin A, is a mitogenic protein for a variety of cell types including endothelial and epithelial cells, melanocytes and keratinocytes. It is identical to scatter factor, a fibroblast-derived soluble factor that promotes the dissociation of epithelial and vascular endothelial cell colonies in monolayes cultures by stimulating cell migration. Table 25 in the examples illustrates detection and measurement of HGF in plasma, urine, saliva and nasal mucus in 17 subjects. Concentrations of HGF in nasal mucus were found to be higher than that found in either plasma or urine. These results suggest that HGF may be synthesized in the serous glands of the nose for a specific mechanism involved with nasal homeostasis as well as a mechanism involved with systemic cell migration. The results provide a non-invasive method for the detection of HGF in nasal mucus. The detection of HGF in nasal mucus provides a non invasive method of diagnosing various diseases related to human physiology and pathology. The diagnosis further leads to a treatment of diseases by modulating the concentrations of HGF by use of drugs.

Some embodiments of the invention include diagnosing disease by detecting platelet derived growth factor in the nasal specimen. Platelet derived growth factor (PDGF) family is a group of disulfide-linked dimeric proteins which act mainly on connective tissue. This family may consist of four homodimeric proteins, PDGF-AA, PDGF-BB, PDGF-CC and PDGF-DD and one heterodimeric protein, PDGF-AB. The technique of ELISA measurement used is associated with the ability of PDGF to stimulate incorporation of 3H-thymidine in quiescent NRGR-3 T 3 fibroblastis. Table 26 in the examples illustrates detection and measurement of PDGF in human plasma, urine, saliva and nasal mucus in 18 subjects. Concentrations of PDGF expressed per mg protein were found to be higher in saliva and nasal mucus than in plasma. These results suggest that PDGF may be synthesized in the serous glands of the nose for a specific mechanism involved with nasal homeostasis. The results provide a non-invasive method for the detection of PDGF in nasal mucus. The detection of PDGF in nasal mucus provides a non invasive method of diagnosing various diseases related to human physiology and pathology. The diagnosis can provide treatment of diseases by modulating the concentrations of PDGF by use of drugs.

Some embodiments of the invention include diagnosing taste loss or smell loss by detecting carbonic anhydrase in the nasal specimen. Carbonic anhydrase is a zinc-containing enzyme and at least twenty carbonic anhydrase variants, called "isozymes" have been identified. Carbonic Anhydrase VI (CA VI) is a 36 KD zinc metalloglycoprotein. Its synthesis in nasal mucus may take place in nasal serous glands (in the oral parotid glands). It can act as a taste bud growth factor in the oral cavity and as an olfactory receptor growth factor in the nasal cavity. It can also act on taste bud and olfactory receptor stem cells to induce growth and development of the entire panoply of cell types for the taste buds and olfactory epithelium. Its decreased synthesis may induce both loss of taste and smell. Its resumed synthesis may return cell growth to normal. Treatment which increases synthesis of CA VI may involve several complex processes including increasing zinc-cofactor concentration. Administration of zinc ion to some patients who are either zinc deficient or who may have metabolic processes which inhibit zinc incorporation into the protein, may have their taste and smell function improved through this treatment. Since the carbohydrates in this protein are part of its function, any process that repairs glycoprotein incorporation into this protein may also therapeutically be effective in restoring taste and smell function.

Table 27 in the examples illustrates decrease in CA VI in patients with smell and taste loss. Table 28 in the examples illustrates loss of smell function by disease etiology with respect to measurements of CA VI concentration in nasal mucus. Results indicate that patients with post influenza hyposmia hypogeusia (PIHH), allergic rhinitis and post anesthesia have significantly decreased CA VI concentrations in nasal mucus. These results provide a method for the detection and measurement of CA VI in nasal mucus as an index of smell and taste loss and its continual measurement during treatment of these disorders in order to monitor efficacy of therapy. The detection of CA VI in nasal mucus provides a non invasive method of diagnosing various diseases related to human physiology and pathology. The diagnosis can further lead to treatment of diseases by modulating the concentrations of CA VI by use of drugs Some embodiments of the invention include diagnosing a disease by detecting cAMP and cGMP in the nasal specimen. Table 29 in the examples illustrates detection and measurement of cAMP and cGMP in saliva and in nasal mucus in normal subjects. Table 30 in the examples illustrates comparison of the measurement of cAMP and cGMP in normal subjects with the patients with taste and smell loss. Results indicated that patients with smell loss had decreased levels of cAMP in their nasal mucus. These results indicate that cAMP in nasal mucus can be an index of smell loss and that its secretion may be inhibited in smell loss. The results provide a non-invasive method for the detection of cAMP and cGMP in nasal mucus.

Table 31 in the examples illustrates detection and measurement of cAMP and cGMP secretion in nasal mucus in patients with graded severity of smell loss (anosmia<Type I hyposmia<Type II hyposmia from most severe to least severe). Data indicates that as degree of smell loss increased, levels of cAMP in nasal mucus decreased. These data confirm the relationship between cAMP secretion in nasal mucus and degree of smell loss. Results also indicate that there was less significant difference between cGMP in nasal mucus in normal subjects or in patients with hyposmia. However, the concentration of cGMP in saliva is essentially similar to that of cAMP, phenomena different from that observed in other tissues.

The ability to smell and, in part, the ability to taste or to obtain flavor from food is regulated by the olfactory nerve system. The olfactory nerve system is complex and interconnected with several systems in the brain. Olfactory receptors located in the nose are specialized bipolar neurons with cilia protruding into the mucous covering the epithelium. The axons of the bipolar neurons are packed into bundles that form connections in the olfactory bulb in the brain. The olfactory bulbs contain a rich supply of neurotransmitters and neuromodulators. Chemosensory dysfunctions are usually described by the following terms: ageusia (absence of taste), hypogeusia, (diminished sensitivity of taste), dysgeusia (distortion of normal taste), anosmia (absence of smell), hyposmia (diminished sense of smell), and dysosmia (distortion of normal smell).

Treatment with drugs which increase cAMP secretion (e.g., the phosphodiesterase theophylline or cilostazol) increases nasal mucus cAMP concentration and are associated with increases in smell function. Thus, cAMP measurements are critical to monitor both loss of smell function and changes in smell function following treatment. The detection of cAMP and cGMP in nasal mucus provides a non-invasive method of diagnosing various diseases related to human physiology and pathology. The methods of the present invention include treatment of diseases by modulating the concentrations of cAMP and cGMP by use of drugs or agents. The method of treatment is preferably by nasal administration.

Some embodiments of the invention include diagnosing a disease by detecting nitric oxide in the nasal specimen. Nitric oxide (NO) is a pletrophic-signaling molecule implicated in diverse biological processes including inhibition of platelet aggregation, regulation of neurotransmission, vasodilation, immune responses and inflammation. NO is synthesized from arginine and $O_2$ by three nitric oxide synthase (NOS) enzymes endothelial NOS (eNOS), neuronal NOS (nNOS), and inducible NOS (iNOS). Each enzyme isoform is expressed in a variety of tissues and cell types. While eNOS and nNOS generally exhibit constitutive expression and are involved in physiological signaling and cellular maintenance functions, iNOS expression may be induced by inflammatory stimuli and may be associated with both normal and pathological immune responses. Table 32 in the examples illustrates detection and measurement of NO in human saliva and nasal mucus. NO was found to be present is in both saliva and nasal mucus and its mean concentration in saliva were 21% lower in patients than in normal subjects whereas in nasal mucus mean levels were 25% lower in patients. Treatment which increases cAMP in nasal mucus and improves smell function may be mirrored by increases in nasal mucus NO.

Some embodiments of the invention include diagnosing a disease by detecting insulin-like growth factor I in the nasal specimen. Insulin-like growth factor I (IGF 1), also known as somatomedin C belongs to the family of insulin-like growth factors that are structurally homologous to proinsulin. IGF 1 is a potent mitogenic factor that mediates growth-promoting activities of growth hormone postnatally. IGF 1 also promotes growth during embryonic growth and differentiation. Table 34 in the examples illustrates detection and measurement of IGF 1 in human saliva and nasal mucus in 26 subjects. Results show that IGF 1 concentration in nasal mucus was significantly greater than in saliva. Results indicate that the measurement of nasal mucus IGF 1 can be used as an index of human physiology and pathology. The detection of IGF 1 in nasal mucus provides a non-invasive method of diagnosing various diseases related to human physiology and pathology. The diagnosis can further help in treatment of diseases by modulating the concentrations of IGF 1 by use of drugs.

Some embodiments of the invention include diagnosing a disease by detecting endoglin in the nasal specimen. Endoglin, also known as CD 105, is a type 1 integral membrane glycoprotein and is an accessory receptor for TGF-β super family ligands. Endoglin is expressed on vascular endothelial cells, chrondrocytes and syncytiotrophoblasts of term placenta. It is also found on activated monocytes, mesenchymol stem cells and leukemic cells of lymphoid and myeloid lineages. Table 39 illustrates detection and measurement of endoglin in the nasal mucus. Results indicate that the measurement of nasal mucus endoglin can be used as an index of human physiology and pathology. The detection of endoglin in nasal mucus provides a non invasive method of diagnosing various diseases related to human physiology and pathology.

Some embodiments of the invention include diagnosing a disease by detecting fibroblast growth factor (FGF) in the nasal specimen. FGF acidic is a member of the FGF family of mitogenic peptides. Unlike other members of the family, it lacks signal peptides. FGF is apparently secreted by mechanisms other than the classical protein secretion pathways. There are approximately 23 distinct members of this family. The nucleotide sequence of human FGF acidic is well known and it is a 155 amino acid protein. FGF mediates cellular responses by binding to and activating a family of four receptor tyrosine kinases. FGF is involved in wound healing as it binds heparin. It promotes endothelial cell proliferation by physical organization of endothelial cells into tubes. It promotes angiogenesis and stimulates the proliferation of fibroblasts that give rise to granulation tissue. It is a more potent angiogenic factor than either VFGF or PDGF. It acts on PC 12 cells; these cells also respond to NGF in a similar manner. Low levels of FGF have been found in blood of patients with depression. Acidic FGF was measured in blood plasma, urine, saliva and nasal mucus in 13 subjects. No FGF was found in any sample of plasma, urine or saliva. FGF was measured in three samples of the nasal mucus or in 23 percent of the subjects. Values ranged from 8-44 pg/ml with a mean±SEM of 24±13 pg/ml. These results suggest that FGF is present in nasal mucus and may be part of a feedback mechanism involving nasal cavity and brain since FGF is synthesized in the brain.

The diagnosis of the disease as disclosed herein can be used to enable or assist in the pharmaceutical drug development process for therapeutic agents. The analysis can be used to diagnose disease for patients enrolling in a clinical trail. The diagnosis can indicate the state of the disease of patients undergoing treatment in clinical trials, and show changes in the state during the treatment. The diagnosis can demonstrate the efficacy of a treatment, and can be used to stratify patients according to their responses to various therapies.

The methods of the present invention can be used to evaluate the efficacy of treatments over time. For example, sample of nasal secretions can be obtained from a patient over a period of time as the patient is undergoing treatment. The DNA from the different samples can be compared to each other to determine the efficacy of the treatment. Also, the methods described herein can be used to compare the efficacies of different therapies and/or responses to one or more treatments in different populations (e.g., different age groups, ethnicities, family histories, etc.).

Figure 2:
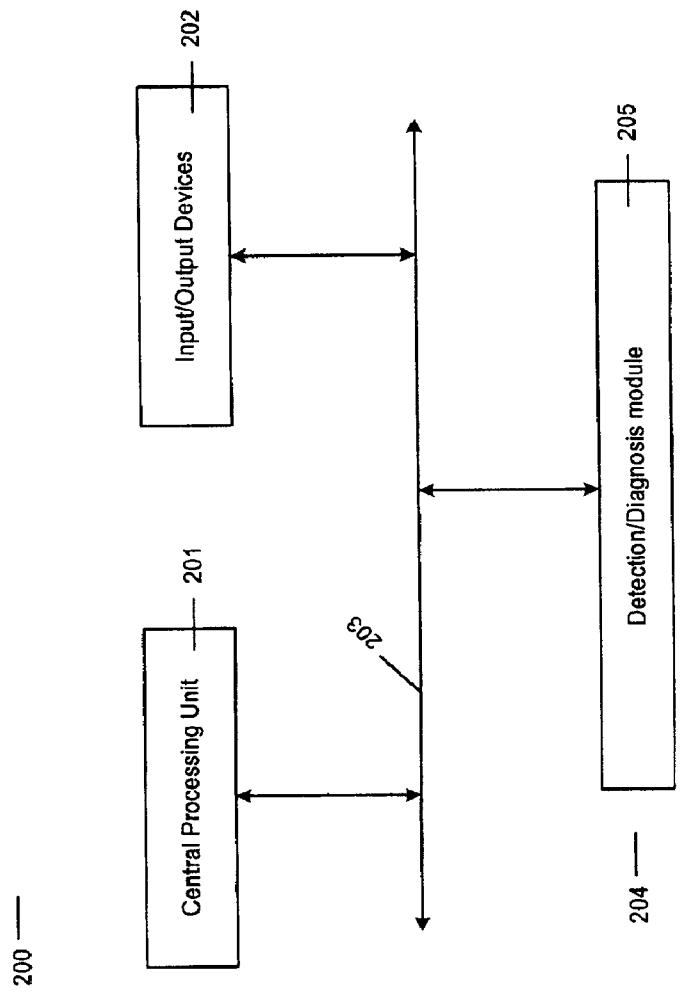
FIG. 2 illustrates a computer for implementing selected operations associated with the methods of the present invention.

In preferred embodiment, at least one step of the methods of the present invention is performed using a computer as depicted in FIG. 2. FIG. 2 illustrates a computer for implementing selected operations associated with the methods of the present invention. The computer 200 includes a central processing unit 201 connected to a set of input/output devices 202 via a system bus 203. The input/output devices 202 may include a keyboard, mouse, scanner, data port, video monitor, liquid crystal display, printer, and the like. A memory 204 in the form of primary and/or secondary memory is also connected to the system bus 203. These components of FIG. 2 characterize a standard computer. This standard computer is programmed in accordance with the invention. In particular, the computer 200 can be programmed to perform various operations of the methods of the present invention.

The memory 204 of the computer 200 may store a detection/diagnosis module 205. In other words, the detection/diagnosis module 205 can perform the operations associated with step 102, 103, and 104 of FIG. 1. The term "detection/diagnosis module" used herein includes, but not limited to, analyzing one or more biological substances, identifying the biological substance, and diagnosing the disease after the identification. The executable code of the detection/diagnosis module 205 may utilize any number of numerical techniques to perform the diagnosis.

Examples of Biological Substances

Various substances that can be diagnosed by the methods of the present invention include, by way of example only, proteins, carbohydrates, lipids, hormones (e.g., leptin, ghrelin) in control of appetite, cholesterol and other lipids and lipid carrying proteins in control of lipid metabolism, growth factors (e.g., hepatic growth factor, granulocyte colony growth factor, brain derived neurotrophic factor), liver enzymes (SGOT, SGPT) therapeutic and recreational drugs of abuse, trace metals [either excess as in toxicity (e.g., lead, mercury, arsenic) or in deficiency diseases involving zinc, copper, magnesium] and most other substances found in plasma, erythrocytes, urine and saliva. Each metabolite in nasal mucus may reflect both physiological and pathological changes in human body metabolism specific to each metabolite and may reflect the manner in which nasal mucus provides information both on human body metabolism such as provided by plasma, erythrocytes, urine and saliva or information relatively unique to nasal mucus.

The methods of the present invention include PCR to enable detection and/or characterization of specific nucleic acid sequences associated with infectious diseases, genetic disorders or cellular disorders. Various infectious diseases can be diagnosed by the presence in clinical samples of specific DNA sequences characteristic of the causative microorganism.

Infectious organisms may comprise viruses, (e.g., single stranded RNA viruses, single stranded DNA viruses, human immunodeficiency virus (HIV), hepatitis A, B, and C virus, herpes simplex virus (HSV), cytomegalovirus (CMV) Epstein-Barr virus (EBV), human papilloma virus (HPV)), parasites (e.g., protozoan and metazoan pathogens such as *Plasmodia* species, *Leishmania* species, *Schistosoma* species, *Trypanosoma* species), bacteria (e.g., *Mycobacteria, M. tuberculosis, Salmonella, Chlamydia, Neisseria, Streptococci, E. coli, Staphylococci, C. psittaci* and *C. pecorum*), fungi (e.g., *Acremonium; Absidia* (e.g., *Absidia corymbifera*). *Aspergillus* (e.g., *Aspergillus clavatus, Aspergillus flavus, Aspergillus fumigatus, Aspergillus nidulans, Aspergillus niger, Aspergillus terreus, Aspergillus versicolor*, etc), *Blastomyces* (e.g., *Blastomyces dermatitidis*, etc), *Candida* (e.g., *Candida albicans, Candida glabrata, Candida guilliermondii, Candida kefyr, Candida krusei, Candida parapsilosis, Candida stellatoidea, Candida tropicalis, Candida utilis*, etc.), *Cladosporium* (e.g., *Cladosporium trichoides*, etc), *Coccidioides* (e.g., *Coccidioides immitis*, etc), *Cryptococcus* (e.g., *Cryptococcus neoformans*, etc), *Cunninghamella* (e.g., *Cunninghamella elegans*, etc), *Dermatophyte, Exophiala* (e.g., *Exophiala dermatitidis, Exophiala spinifera*, etc), *Epidermophyton* (e.g., *Epidermophyton floccosum*, etc), *Fonsecaea* (e.g., *Fonsecaea pedrosoi*, etc), *Fusarium* (e.g., *Fusarium solani*, etc), *Geotrichum* (e.g., *Geotrichum candiddum*, etc), *Histoplasma* (e.g., *Histoplasma capsulatum* var. *capsulatum*, etc), *Malassezia* (e.g., *Malassezia furfur*, etc), *Microsporum* (e.g., *Microsporum canis, Microsporum gypseum*, etc), *Mucor, Paracoccidioides* (e.g., *Paracoccidioides brasiliensis*, etc), *Penicillium* (e.g., *Penicillium marneffei*, etc), *Phialophora, Pneumocystis* (e.g., *Pneumocystis carinii*, etc), *Pseudallescheria* (e.g., *Pseudallescheria boydii*, etc), *Rhizopus* (e.g., *Rhizopus microsporus* var. *rhizopodiformis, Rhizopus oryzae*, etc), *Saccharomyces* (e.g., *Saccharomyces cerevisiae*, etc), *Scopulariopsis, Sporothrix* (e.g., *Sporothrix schenckii*, etc), *Trichophyton* (e.g., *Trichophyton mentagrophytes, Trichophyton rubrum*, etc), *Trichosporon* (e.g., *Trichosporon asahii, Trichosporon cutaneum*, etc).), *Pneumocystis carinii*, and *prions*.

Other examples of biological substances, includes, but is not limited to, colony stimulating factors (1, 2, 3, GM, $\alpha$, $\beta$, $\gamma$, and the like), B cell factors (B cell growth factor and the like), T cell factors, protein A, suppressive factor of allergy, suppressor factors, cytotoxic glycoprotein, immunocytotoxic agents, immunotoxins, lymphotoxins, cachectin, oncostatins, tumor inhibitory factors, albumin, $\alpha$-1-antitrypsin, apolipoprotein, erythroid potentiating factors, erythropoietin, factor VII, factor VIII(c), factor IX, hemopoietin-1, kidney plasminogen activator, tissue plasminogen activator, urokinase, pro-urokinase, streptokinase, lipocortin, lipomodulin, macrocortin, lung surfactant protein, protein C, protein 5, C-reactive protein, renin inhibitors, collagenase inhibitors, superoxide dismutase, growth hormone, osteogenic growth factors, atrial naturetic factor, auriculin, atriopeptin, bone morphogenic protein, calcitonin, calcitonin precursor, calcitonin gene-related peptide, cartilage inducing factor, connective tissue activator protein, fertility hormones (follicle stimulating hormone, luteinizing hormone, human chorionic gonadotropin), growth hormone releasing factor, osteogenic protein, insulin, proinsulin, nerve growth factor, parathyroid hormone and analogues, parathyroid hormone antagonists, relaxin, secretin, somatomedin C, somatostatin and somatostatin analogues, inhibin, adrenocoricotrophic hormone, glucagon, vasoactive intestinal polypeptide, gastric inhibitory peptide, motilin, cholecystokinin, pancreatic polypeptide, gastrin releasing peptide, corticotropin releasing factor, thyroid stimulating hormone, growth inhibitory factors, vaccine antigens including antigens of HTLV-I, II, HTLV-III/LAV/HIV (AIDS virus), cytomegalovirus, hepatitis A, B, and non-A/non-B, herpes simplex virus-1, herpes simplex virus II, malaria, pseudorabies, retroviruses, feline leukemia virus, bovine leukemia virus, transmissible gastroenteritis virus, infectious bovine rhinotracheitis, parainfluenza, influenza, rotaviruses, respiratory syncytial virus, varicella zoster virus, epstein-barr virus, pertussis, and anti-infective antibodies including monoclonal and polyclonal antibodies to gram negative bacteria, pseudomonas, endotoxin, tetanus toxin, and other bacterial or viral or other infectious organisms.

In addition to naturally-occurring allelic forms of growth inhibitory factor, the present invention also embraces other inhibitory factor products such as polypeptide analogs of inhibitory factor. Such analogs include fragments of inhibitory factor. Other examples of biological substances, includes, substances that are associated with cancer (either active or remission) and/or with reaction to transplantation (either tissue acceptance or rejection).

We compared levels of many biologic substances in nasal mucus with those in blood, urine and saliva using a 96 plate colorimetric ELISA assay. Most of these substances are detectable in nasal mucus, sometimes at levels that are significantly higher compared to other biologic fluids. These results indicate that, while the specific mechanisms for the presence of these varied substances in nasal mucus are unclear, their presence reflects unique indicators of both human physiology and disease.

Methods of the present invention include methods for the detection of the following biologic substances in nasal mucus: agouti related protein, alpha fetoprotein (AFP), brain derived neurotrophic factor (BDNF), bone morphogenetic protein-2 (BMP-2), ciliary neurotrophic factor (CNTF), thymus and activation-regulated chemokines (CCL17/TARC) CC chemokines, cystatin, D-dimer, E selectin, endoglin, epidermal growth factor, (EGF), endothelial nitric oxide synthase, (eNOS), FAS ligand, fibroblastic growth factor basic (FGF basis), granulocyte macrophage colony stimulating factor (GM-CSF), hepatocyte growth factor (HGF), inducible nitric oxide synthase (iNOS), insulin-like growth factor 1 (IGF-1), interferon alpha (INF-α), interferon beta (INF-β), interferon gamma (INF-γ), interferon omega (INF-ω), intracellular adhesion molecule 1 (ICAM-1), interleukin-1 (IL-1), interleukin-1 receptor (IL-1 receptor), interleukin-2 (IL-2), interleukin-2 receptor (IL-2 receptor), interleukin-3 (IL-3), interleukin-6 (IL-6), interleukin-15 (IL-15), interleukin-17 (IL-17), interleukin-18 (IL-18), keratinocyte growth factor (KGF), L-selectin, leptin, leukemia inhibitor factor (LIF), matrix metalloproteinase 1 (MMP-1), migrating inhibitory factor (MIF), nerve growth factor (NGF), P selectin, placental growth factor (PlGF), platelet derived growth factor-AA (PDGF-AA), platelet derived growth factor-BB (PDGF-BB), pro-B type natiuretic peptide, receptor for abdominal glycation end product (RAGE), stem cell factor (SCF), substance P, triggering receptor expressed on myeloid cells (TREM-1), transforming growth factor alpha (TGF-alpha), transforming growth factor beta (TGF-beta), tumor necrosis factor (TNF), tumor necrosis factor receptor 1 (TNF-R1), tumor necrosis factor receptor 2 (TNF-R2), TNF-related apoptosis-inducing ligand (TRAIL), vascular cell adhesion molecule 1 (VCAM1), vascular endothelial growth factor C (VEGF-C), vascular growth factor D (VEGF-D), vascular endothelia growth factor receptor 1 (VEGFR1), or vascular endothelia growth factor receptor 2 (VEGFR2). Levels of these biologic substances are directly or indirectly associated with numerous disease processes or condition and their concentration in nasal mucus may increase or decrease during the course of disease progression. Detection of a biologic substance in nasal mucus can be used as a diagnostic method for identifying a disease and ascertaining the stage of the disease process. Levels of some biologic substances may change prior to the appearance of disease symptoms and may therefore represent a means by which a disease or condition may be detected early, providing the opportunity for early treatment including prophylactic treatment. Additionally, the level of these biologic substances may change with the appropriate disease treatment and therefore, response to treatment can also be used to measure through nasal mucus levels of these substances. Furthermore, as many of these substances are themselves potent biologic agents, they can be administered prophylactically or with intent to treat a particular disease. Nasal mucus monitoring then provides a way to titrate the administered dosage to achieve the desired therapeutic response and to ensure that the patient is receiving a medically adequate dose.

Detection of biological substances can also provide information from which the likelihood of the occurrence of a disease or condition can be calculated. Table 47. This information can be used by a health care provider in developing a preventative treatment strategy. For example, if detection of a biological substance is linked to an increased risk of a myocardial infarction, the health care provider can counsel the patient to make changes to the patient's diet, initiate or intensive an exercise program, prescribe a medication or change medications. Detection of a biological substance can also indicate the likelihood and/or rate of disease progression. Based on the information current treatment can be modified, including adding therapeutic agents or modalities.

Some embodiments of the invention include diagnosing a disease by detecting alpha fetoprotein (AFP). AFP is a fetal/tumor associated protein that is also a member of the albuminoid super family. AFP can act as carrier protein binding several types of molecules including steroids, bilirubin, fatty acids, retinoids and flavanoids. AFP can also regulate cell growth and survival. It is secreted by certain cancers such as hepatocellular cancer, cancers of the gastrointestinal track, endodermal sinus tumors, neuroblastoma, and hepatoblastoma and hence, increased levels of APF can serve as a biomarker indicating the presence, hematogenous spread and response to therapy of these cancers. Elevated levels are also seen in multiple gestation as well as in a number of fetal abnormalities, such as neural tube defects including spina bifida and anencephaly, abdominal wall defects and Ataxia-telangiotosis. AFP is also elevated in chronic hepatitis C infection. In contrast, low levels of maternal serum AFP are associated with, Down syndrome and Trisomy 18. Patients with abnormal levels need to undergo detailed obstetric ultrasonography. The information is then used to decide whether to proceed with amniocentesis. AFP levels may be predictive of a chromosomally abnormal fetus in the $2^{nd}$ trimester, fetal Trisomy 18, hepatocellular cancer and gastric cancer with liver metastasis. Table 46.

Some embodiments of the invention include diagnosing a disease by detecting agouti-related protein (AGRP), a neuropeptide and a functional antagonist of aMSH on melanocortin (MC) 3 and MC4 receptors, both of which are implicated in obesity. It shares sequences and structural homology with Agouti protein. Increased levels are associated with obesity and anorexia and hence, AGRP may serve as a biomarker for appetite related diseases. Furthermore, AGRP and related analogs can serve as therapeutic drugs to treat appetite changes and nasal mucus monitoring may be an ideal way to ascertain drug levels. It was discovered that nasal mucus levels of AGRP to be approximately 10% that of plasma ($p<0.001$) and saliva to be approximately 17% of plasma. Table 46.

Some embodiments of the invention include diagnosing a disease by detecting brain-derived neurotrophic factor (BDNF), a member of the NGF family of neurotrophic factors. It is required for differentiation and survival of specific neuronal subpopulations in both central and peripheral neurons systems. High levels of BDNF are found in hippocampus, cerebellum, fetal eye and placenta. High levels are associated with medulablastoma and increased itching in eczema. Decreased levels are associated with Huntington's disease, depression, schizophrenia, obsessive-compulsive disorder, Alzheimer's disease, and dementia, and medulloblastoma. Increasing levels of BDNF, additionally, may be predictive of the development of Parkinson's disease. It was found that nasal mucus levels of BDNF to be approximately 0.2% of the plasma level ($p<0.001$) with saliva and urine having undetectable levels. Table 46.

Some embodiments of the invention include diagnosing a disease by detecting bone morphogenetic protein-2 (BMP-2), a secreted signaling molecule that composes a subfamily of the TGF-β superfamily. BMP-2 was originally specified as a regulator of cartilage and bone formation. There are at least 20 structurally and functionally active BMPs most of which play roles in embryogenesis and morphogenesis of various body tissues and organs. Active BMPs are usually heterodimers containing a characteristic cysteine-knot structure. It is a potent inducer of bone function. Increased levels of BMPs are associated with gastric and ovarian cancer, malignant melanoma, and chronic renal fibrosis. Table 46.

Some embodiments of the invention include diagnosing a disease by detecting cyclic AMP (cAMP) a growth factor which acts on stem cells in taste buds and olfactory epithelium. If cAMP levels decrease, taste and smell loss follows. cAMP is also involved as a "second messenger" in all endocrine and many physiological processes.

Some embodiments of the invention include diagnosing a disease by detecting carbonic anhydrase, an enzyme involved in the functional process of pH control, respiration and sensory function. It acts as a growth factor for stem cells in taste buds and olfactory epithelium. If carbonic anhydrase levels decrease, taste and smell loss follow.

Some embodiments of the invention include diagnosing a disease by detecting thymus and activation-regulated chemokines (CCL17/TARC) that comprise a subfamily of the chemokines superfamily. They are defined by the arrangement of the first two of four invariant cysteine residues found in all chemokines. In CC chemokines these two cysteines are adjacent. Chemokines bind to multiple 7-transmembrane G protein-coupled CC chemokine receptors. These are small secreted molecules that function in leukocyte trafficking, recruitment and activation. They also play roles in normal and pathological processes including allergic responses, infection and autoimmune disease, angiogenesis, inflammation and tumor growth and metastasis. Increased levels of TARC are associated with Hodgkin's lymphoma, Adult T-cell leukemia/lymphoma (ATL), allergic disease, asthma, atopic dermatitis, systemic lupus erythematosis, angioedema, Trisomy 7 and *Paragonimus westermani* infection. Thymic tumors may secrete an excessive amount of CCL17/TARC and thus may be a good marker for disease activity, either before or after tumor treatment. It was found that nasal mucus levels of TARC were approximately 150% of plasma levels, however, the difference was not statistically significant. Table 46. TARC was not detectable in saliva or urine.

Some embodiments of the invention include diagnosing a disease by detecting ciliary neurotrophic factor (CNTF), a molecule that is structurally similar to IL-6, IL-11, CLC and DSM. CNTF is a trophic factor for embryonic chick ciliary parasympathetic neurons in culture and is also a survival factor for several neuronal cell types including dorsal root ganglion sensory neurons, sympathetic ganglion neurons, embryonic motor neurons, major pelvic ganglion neurons and hippocampal neurons. Decreased levels are associated with motor neuron degeneration, amyotrophic lateral sclerosis (ALS), multiple sclerosis (MS), and Huntington's disease. Table 46.

Some embodiments of the invention include diagnosing a disease by detecting caspase 3 (CP3), also known CPP32/Yama. Caspases are a family of cytosolic aspartate-specific cysteine proteases involved in the initiation and execution of apoptosis. They are expressed as latent zymogens and are activated by auto-proteolytic mechanisms by processing by other proteases (frequently other caspases). Caspases can be subdivided into three function groups—caspase 3 belong to the apoptosis execution group along with caspase 5 and 7. Some embodiments of the invention include diagnosing a disease by detecting C reactive protein (CRP). It is a member of the class of acute phase reactants. Levels of CRP rise dramatically during an acute inflammatory event. The basal level of CRP is indicative of the general health of a patient. Patients with elevated basal levels of CRP are at an increased risk for diabetes, hypertension and cardiovascular disease. Colon cancer patients have an elevated level of CRP. Approximately 20% of individual with increasing blood levels of CRP develop chronic obstructive pulmonary disease (COPD) one to eight years later. Monitoring patients for CRP by nasal mucus may provide a way to identify patients prone to the disease enabling prophylactic treatment.

Some embodiments of the invention include diagnosing a disease by detecting cystatin, an inhibitor of cysteine proteases. It is both intracellular and extracellular. It is a homolog of fetuin, HPRG and kininogen. It regulates protease activity. It is involved in many physiological and pathological processes such as tumor invasion and metastases, inflammation and neurological diseases. Mutations in cystatins B & C cause progressive myoclonus epilepsy and a hereditary form of amyloid angiopathy.

Some embodiments of the invention include diagnosing a disease by detecting D-dimer, also known as fragment D-dimer, or fibrin degradation fragment. Elevated levels of D-dimer are associated with deep vein thrombosis (DVT), disseminated intravascular coagulation (DIC) and pulmonary embolism. D-dimer levels can also be monitored to assess the effectiveness of thrombolytic therapy. A preferred embodiment is to assess risk of a repeat thromboembolic event. D-dimer levels in the blood can increase when patients stop anticoagulation therapy for treatment of thromboembolism. Among patients that stop anticoagulation therapy, about 15% have abnormal D-dimer levels and are at high risk for a repeat thromboembolic event. Thus, measurement of D-dimer levels in blood can be used to predict the onset of repeat thromboembolic events among patients who have had a previous event of this type and have stopped anticoagulation therapy. The importance of this finding is that prior to the discovery of D-dimer in blood and the association with repeat thromboembolic events, it was impossible to predict the length of time necessary to continue anticoagulation therapy to inhibit repeat thromboembolism. Now, it may be possible to screen patients for D-dimer by sampling nasal mucus to provide a simple, rapid and low cost screening method for patients at risk for a repeat thromboembolic event and continue these patients on anticoagulation therapy.

Some embodiments of the invention include diagnosing a disease by detecting E selectin, also known as CD62E. E selectin, is a cell adhesion molecule expressed only on endothelial cells activated by cytokines. Elevated E selectin levels are associated with angiomas, essential hypertension, non-insulin dependent diabetes mellitus, rheumatoid arthritis, and blood forming tumors.

Some embodiments of the invention include diagnosing a disease by detecting endoglin, a transmembrane glycoprotein. It is an accessory receptor for TGF-β superfamily ligands. It is highly expressed on vascular epithelial cells, chondrocytes and syncytiotrophoblasts of term placenta. It is also found on activated monocytes, mesenchynal stem cells and leukemic cells of lymphoid and myeloid integers. It is increased in eclampsia and preeclampsia. In a preferred embodiment, endoglin in nasal mucus is used as a prognostic indicator of for the development of preeclampsia in pregnancy. Preeclampsia occurs in 3-5% of all pregnancies in the world. It is a significant cause of maternal and fetal mortality. It has recently been demonstrated that circulating levels of soluble endoglin are present in serum of pregnant women with preeclampsia. Table 48. It has also been demonstrated that circulatory levels of soluble endoglin are significantly elevated in pregnant women with preterm preeclampsia. Table 48. Further, circulating levels of soluble endoglin are elevated in pregnant women up to 10 weeks prior to the onset of clinical manifestations of preeclampsia, however, soluble endoglin is not elevated in women who have gestational hypertension or in women who remain normotensive, but deliver growth-restricted neonates. In this sense, elevated endoglin levels in blood plasma can be used to predict the onset of preeclampsia prior to its clinical manifestation.

Levels of endoglin in blood plasma, nasal mucus, saliva and urine in a group of patients with a variety of clinical disorders were compared using a 96 plate colorimetric ELISA assay. Endoglin in plasma ranged from 1.1-6.0 ng/ml (2.7±0.2 mean±SEM) whereas in nasal mucus it ranged from 0.02-3.0 ng/ml (0.8±0.5); it was not measurable in saliva or urine in any of these patients. Table 49. While levels of endoglin were approximately three times higher in plasma than in nasal mucus, the collection of nasal mucus does not require any invasive procedure and is more easily performed and accepted by patients than venipuncture.

Some embodiments of the invention include diagnosing a disease by detecting endostatin, a 20 KD C-terminal fragment of collagen XVIII that functions as an angiogenesis antagonist. Decreased levels are associated with cancer including metastatic cancer, gastric ulcers and impaired wound healing.

Some embodiments of the invention include diagnosing a disease by detecting endothelial nitric oxide synthase (eNOS), also known as constitutive NOS (cNOS) or type III. eNOS is one of three enzymes that synthesize nitric oxide (NO) from L-arginine. Endothelial NOS constitutively provides a basal release of NO to blood vessels, where NO release is involved with regulating vascular function. Decreased levels of eNOS are associated with heart failure, vascular disease and impaired wound healing. Table 46.

Some embodiments of the invention include diagnosing a disease by detecting epidermal growth factor (EGF), a growth factor derived from membrane-anchored precursors. EGF promotes proliferation and differentiation of mesenchynal and epithelial cells. It is involved in signaling in a wide variety of physiological processes including human carcinomas. Increased levels are associated with breast cancer, lung cancer and pituitary adenoma. It was found that nasal mucus levels are approximately 150-fold higher than plasma levels ($p<0.0001$) and saliva levels approximately 26-fold higher than plasma levels ($p<0.001$). Table 46.

Some embodiments of the invention include diagnosing a disease by detecting erythropoietin (EPO), a 30 KD heavily glycosylated protein produced primarily by the kidney. EPO is the principle factor (hormone) that regulates erythropoiesis (in the bone marrow where is acting as a growth factor). Its synthesis is increased by hypoxia or anemia. Decreased levels are associated with anemia including chemotherapy induced anemia, renal failure, severe kidney disease, myelodysplasia syndromes, aplastic anemia, and uremia. Increased or increasing levels of EPO are associated with hemodialysis patient response to iron therapy.

Some embodiments of the invention include diagnosing a disease by detecting FAS-ligand, a 40 KD Type II transmembrane protein belonging to the TNF superfamily. It is expressed predominantly on activated T cells and natural killer (NK) cells, whereas FAS is expressed on various cell types. FAS-ligand/FAS system plays a crucial role in modulating immune responses by inducing cell specific apoptosis. Human FAS-ligand shares 81% sequence identity with mouse FAS-ligand. Defective Fas mediated apoptosis may lead to oncogenesis as well as drug resistance in existing tumors. Germline mutation of Fas is associated with autoimmune lymphoproliferative syndrome (ALPS), a childhood disorder of apoptosis. Increased levels of FAS-ligand are associated with leukemia, primary cancers, including lung, colon, pancreas, metastatic cancer, lymphoproliferative diseases, MS, SLE, HIV, hepatitis, and pulmonary fibrosis. It was discovered that nasal mucus FAS-ligand levels were approximately 6% of plasma levels ($p<0.001$), but approximately 5.5-fold higher than urine levels ($p<0.05$). Table 46.

Some embodiments of the invention include diagnosing a disease by detecting fibroblast growth factor (FGF) acidic, also known as FGF1. FGF acidic is a part of a large family of secreted proteins involved in many aspects of cellular development including cell proliferation, growth and differentiation. FGF acidic acts on several cell types to regulate physiological functions including angiogenesis, cell growth, pattern formation, embryonic development, metabolic regulation, cell migration, neurotrophic effects and tissue repair. Activities are mediated by receptor tyrosine kinases and are facilitated by hepatic sulfate. Increased levels are associated with bladder cancer, pancreatic cancer, glioblastoma multiforme, meningioma, atheroma, inflammatory arthritis, Crouzon syndrome and spinal cord injuries.

Some embodiments of the invention include diagnosing a disease by detecting fibroblast growth factor (FGF) basic, also known as bFGF or FGF2, a member of the fibroblast growth factor family. FGF basic stimulates the proliferation of all cells of mesodermal origin and many cells of neuroectodermal, ectodermal, and endodermal origin. FGF basic induces neuron differentiation, survival, and regeneration. FGF basic also modulates embryonic development and differentiation. FGF basic may play a role in vivo in the modulation of angiogenesis, wound healing and tissue repair, embryonic development and differentiation, and neuronal function and neural degeneration. Increased levels of FGF basic are associated with bladder and pancreatic cancers. Decreased levels of FGF basic are associated with ischemia cardiac function, Kaposi's sarcoma and brain tumors. It was discovered that FGF basic can be detected in nasal mucus, but not in the other bodily fluids. Table 46.

Some embodiments of the invention include diagnosing a disease by detecting granulocyte macrophage growth factor (GM-CSF), a 22 KD monomeric hematopoietic cytokine characterized initially as a growth factor that supported in vitro colony formation of granulocyte macrophage progenitors. GM-CSF is produced by several cell types including activated T cells, B cells, macrophages, mast cells, endothelial cells and fibroblasts in response to cytokine or immune and inflammatory stimuli. GM-CSF is species specific. Elevated GM-CSF levels are associated with asthma, acute and chronic bronchitis, chronic sinusitis, acute myeloblastic leukemia (AML) and melanoma.

Some embodiments of the invention include diagnosing a disease by detecting hepatocyte growth factor (HGF) also known as hepatopoeitin A. HGF is mitogenic for several cell types including endothelial and epithelial cells, melanocytes and keratinocytes. It is identical to scatter factor, a fibroblast-derived soluble factor that promotes dissociation of epithelial and vascular endothelial cell colonies in monolayer cultures by stimulating cell migration. It is excreted as an inactive single chain precursor and is converted to the active heterodimeric form by HGF activation. Elevated levels are associated with hepatitis, hepatic failure, cirrhosis, liver regeneration post transplantation, lung regeneration post transplantation, acute kidney injury, kidney disease, myocardial infarction, glioma, and pancreatic cancer.

Inducible nitric oxide synthase (iNOS), also known as type II, is one of three enzymes that synthesize nitric oxide (NO) from L-arginine. Nasal mucus levels of iNOS were twice that of plasma levels, but the differences were not statistically significant. Table 46. Saliva levels of iNOS were approximately 60% of nasal mucus levels.

Some embodiments of the invention include diagnosing a disease by detecting insulin-like growth factor 1 (IGF-1). IGF-1 is mainly secreted by the liver as a result of stimulation by growth hormone (GH) and plays an important role in childhood growth with anabolic effects in adults. Increased levels of IGF-1 are associated with diabetes. Decreased levels of IGF-1 result in growth deficiencies in children. Administration of IGF-1 can ameliorate the problem. It was found that IGF-1 levels in nasal mucus are approximately 3-fold higher then IGF-1 levels in saliva (p<0.001). Table 46.

Some embodiments of the invention include diagnosing a disease by detecting intracellular adhesion molecule 1 (ICAM-1) or CD 54, a transmembrane protein that contains 2-9 extracellular Ig-like C-2 type domains. ICAMs bind to LFA-1 integrins and mediate adhesion interaction with cells of the immune system. It is differentially expressed on epithelial, endothelial and hematopoietic cells and may be expressed in brain. Elevated levels of ICAM-1 are associated with carotid arteriosclerosis, cardiac ischemia, cardiac transplantation, subarachnoid hemorrhage (SAH), stroke, asthma, HIV, melanoma, and lymphoma. It was discovered that nasal mucus levels are approximately 26% of plasma levels (p<0.001) with saliva at approximately 15% of plasma levels. Table 46.

Some embodiments of the invention include diagnosing a disease by detecting interferon alpha (IFN-α) a member of the Type I interferon family, that share a common receptor complex. IFN-α has both antiviral and immunomodulating activities on target cells. Increased levels of IFN-α are associated with viral infections including hepatitis C. IFN-α is administered to treat viral infections including hepatitis C, and cancers such as bladder cancer, renal cell cancer, melanoma and chromamyelocyte leukemia. Nasal mucus monitoring represents a new method to measure treatment levels of IFN-α in patients receiving IFN-α treatment It was discovered that nasal mucus levels of IFN-α are almost twice that of plasma (p<0.01), while saliva was almost six-fold higher than plasma. Table 46. Patients with allergic diseases had increased levels of IFN-α compared to controls.

Some embodiments of the invention include diagnosing a disease by detecting interferon β (IFNβ), a member of the Type I interferon family. It shares a common cell surface receptor with IFNα and IFNγ. IFN-β is a potent antiviral substance. It can be used as an antiviral and antitumor treatment through nasal inhalation. IFN-β may also antagonize the effects of IFN-γ and other proinflammatory cytokines, such as tumor necrosis factor and IL-1, and thereby down-regulate T-cell activity.

IFN-β is administered to treat hepatitis C, papilloma virus, multiple sclerosis, condylomatosis, lung fibrosis and melanoma. Nasal mucus monitoring represents a new method to measure treatment levels of IFN-β in patients receiving IFN-β treatment. It was discovered that nasal mucus levels are approximately half of plasma levels, but the difference was not statistically significant. Table 46. Nasal mucus levels are approximately 15-fold greater than saliva levels. Patients with allergic diseases had increased levels of IFN-β compared to controls, as did post influenza patients.

Some embodiments of the invention include diagnosing a disease by detecting interferon-γ (IFN-γ), a type II interferon or immune interferon produced by T cells and natural killer (NK) cells. It shares no significant homology with IFNβ or IFNα. It exists in mature form as a non-covalently linked homodimer Decreased levels of IFN-γ are associated with tuberculosis, chlamydia, atopic disease, and cervical cancer. Interferon-γ (INFγ) is the initial and primary inducer of immunoproteasomes during viral infection. It is a major cytokine in many viral infections, and is known to alter the composition and function of many viral infections (4). INFγ induces the transcription and translation of the 3 immunoproteasome subunits β1i (LMP2), β2i (MECL-1) and β5i (LMP7) which replace their constitutive counterparts β1, β2 and β5, respectively, during de novo assembly of proteosomes (5). INFγ plays an important role in the induction of immunoproteasomes as demonstrated in a murine model of fungal infection (5). Many viruses induce a vigorous Type 1 INF response. INFγ can be found at the site of active viral infection. It has been well studied as both an active and more chronic indication of viral disease. Decreased levels of INFγ are associated with tuberculosis, chlamydia, atopic disease and cervical cancer. Increased levels may be predictive of atopic eczema.

INFγ could not be detected in plasma, saliva or urine but it is found only in nasal mucus ranging from 0-333 pg/ml (85±18 pg/ml, Mean±SEM). Table 46. This finding in nasal mucus is independent of the presence of blood or active infection in the nose. This finding suggests that the nasal cavity is an active portal of entry of viral particles into the body and that INFγ in the nasal cavity reflects an important reaction to this entry. Its level can reflect endogenous susceptibility to infection, resistance to infection and/or activity of infection. As such its measurement may be an important step in recognizing how viruses of any type alter human metabolism as related to immune system activity. Interestingly, these results with INFγ and other substances that are elevated in viral infections may provide useful surrogate markers to define the extent and severity of a specific disease—e.g. levels of INFγ in viral diseases such as hepatitis, HIV AIDS, etc. They may even substitute for measurements of active viral loads.

Some embodiments of the invention include diagnosing a disease by detecting interferon-ω (IFN-ω), also known as leukocyte (II) interferon. IFN-ω is a monomeric glycoprotein distantly related to IFNα and β but unrelated to IFNγ. Its binding characteristics are similar to those of other interferons. IFN-ω can be used to treat hepatitis B and C, other viral infections and forms of cancer. It was discovered that nasal mucus levels of IFN-ω are similar to plasma levels, while IFN-ω was undetectable in urine. Table 46.

Some embodiments of the invention include diagnosing a disease by detecting interferon receptor, comprising two subunits, IFNAR1 and IFNAR2. Nasal mucus levels were approximately 6-fold higher than saliva levels at 271±14 pg/ml versus 43.3 pg/ml. Interestingly, patients with allergic disease had nasal mucus levels of approximately 3.5-fold higher than control levels, while post influenza patients had approximately 4.6-folder higher level.

Some embodiments of the invention include diagnosing a disease by detecting interleukin 1 alpha (IL-1), a cytokine produced by a variety of cells in response to inflammation, infection and/or microbial toxins. Increased levels of IL-1 are associated with leukemia, solid tumors, Down's syndrome, Alzheimer's disease, HIV, meningococcal shock, adult periodontal disease, and ulcerative colitis. Increasing levels of IL-1 may be predictive of premature labor. It was discovered that nasal mucus levels are approximately 69-fold higher compared to saliva levels and over 1900-fold higher compared to plasma levels in normal individuals. Table 46. Additionally, nasal mucus levels are elevated in patients with head injuries and decreased in patient with allergic disease. Some embodiments of the invention include diagnosing a disease by detecting interleukin 1 receptor. Increased levels of interleukin 1 receptor are associated with rheumatoid arthritis, osteoarthritis, silicosis, cerebral ischemia, stroke, traumatic brain injury, gastritis, septic shock, and abdominal aortic aneurysm. Increased levels may be predictive for the development of peridontal disease and inflammatory skin diseases. It was discovered that nasal mucus levels of interleukin 1 receptor are approximately 9% of plasma levels (p<0.001), while saliva levels were approximately 1.1% of plasma levels. Table 46. Increased levels of interleukin 1 receptor were noted in patients with head injury.

Some embodiments of the invention include diagnosing a disease by detecting interleukin 2 (IL-2), a T cell growth factor produced by T cells following activation by mitogens or antigens. It has also been shown to stimulate growth and inhibition of B cells, NK cells, lymphocyte-activated killer cells (LAK), monocytes/macrophages and oligodendrocytes. Increased IL-2 levels are associated with cancers including gastric cancer and melanoma and in diabetic nephropathy. It was discovered that IL-2 could only be detected in nasal mucus and not in the other bodily fluids. Table 46. Elevated levels of IL-2 were noted in post influenza patients and those with active allergies.

Some embodiments of the invention include diagnosing a disease by detecting interleukin 2 receptor (IL-2 receptor). Increased levels of IL-2 receptor are associated with myelodysplastics syndrome and leukemia. Increasing levels of IL-2 receptor may be predictive of the development of gastic cancer and metastatic disease and colon cancer and metastatic disease. It was discovered that the level of IL-2 receptor in nasal mucus was approximately 7% of plasma levels (p<0.001), while saliva levels were approximately 1.2% of plasma levels. Table 46.

Some embodiments of the invention include diagnosing a disease by detecting interleukin 3 (IL-3), also known as mast cell growth factor. It is a pleotropic factor produced by activated T cells. IL-3 can stimulate proliferation and differentiation of pluripotent hematopoeitic stem cells as well as various lineage-committed progenitors. Increased levels of Il-3 are associated with myeloproliferative syndrome and acute myelogenous leukemia. IL-3 was detectable in both nasal mucus and saliva. Table 46.

Some embodiments of the invention include diagnosing a disease by detecting interleukin 6 (IL-6), a multifunctional a helical cytokine that plays important roles in host defense, acute phase reaction, immune response and hematopoiesis. It is expressed by both normal and transformed cells including T cells, B cells, monocytes/macrophages, fibroblasts, hepatocytes, keratinocytes, astrocytes, vascular endothelial cells and various tumor cells. Interleukin 6 (IL-6) binds to a high affinity receptor complex consisting of two membrane glycoproteins: an 80 KD component receptor that bind IL-6 with low affinity (IL6-R) and a signal-transducing component of 130 KD that does not bind IL-6 itself but is required for high-affinity binding of IL-6 by the complex. Increased levels of IL-6 are associated with osteoporosis, rheumatoid arthritis, meningococcal shock, sepsis, systemic lupus erythemitosis, glomerulnephritis, prostate cancer and active HIV. Increased levels of IL-6 may be predictive of future myocardial infarction, development of coronary disease, unstable angina, or preterm labor. It was discovered that IL-6 levels in nasal mucus are approximately 17-fold greater than plasma levels (p<0.001). Table 46. Post influenza patients and those with allergic disease had about a 3-fold higher level of IL-6 than controls.

Some embodiments of the invention include diagnosing a disease by detecting interleukin 15 (IL-15), a cytokine with structural similarity to IL-2 that is secreted by mononuclear phagocytes following viral infection. IL-15 induces cell proliferation of natural killer cells; cells of the innate immune system whose principal role is to kill virally infected cells. Increased levels of IL-15 are associated with rheumatoid arthritis, ulcerative colitis, inflammatory bowel disease, hepatitis C induced liver disease, hepatocellular carcinoma, cardiac disease, fibromyalgia, lymphoproliferative disorder of granular lymphocytes (LDGL) and other chronic lymphoproliferative diseases, hairy cell and B cell leukemia, and transplant rejection. It was discovered that IL-15 levels in nasal mucus are approximately 32-fold higher compared to plasma levels (p<0.001), while saliva levels were similar to plasma levels. Table 46.

Some embodiments of the invention include diagnosing a disease by detecting interleukin 17 (IL-17), also known as IL-17A, a member of the IL-17 family that includes IL-17B, IL-17C, IL-17D, IL-17E (also called IL-25), and IL-17F. All members of the IL-17 family have a similar protein structure, yet they have no sequence similarity to any other known cytokines. Increased levels of IL-17 are associated with rheumatoid arthritis, MS, scleroderma, osteoarthritis, chronic obstructive pulmonary disease (COPD), and lung inflammation. Nasal mucus and saliva levels of IL-17 were similar, however, IL-17 was not detectable in plasma. Table 46.

Some embodiments of the invention include diagnosing a disease by detecting interleukin 18 (IL-18), also known as interferon-gamma-inducing factor (IGIF) or IL-IF4, IL-18 shares biologic activity with IL-12. It is synthesized as a propeptide that is cleaved to create a 19 KD monoglycosylated monomer. Increased levels of IL-18 are associated with unstable angina, atherosclerosis, myocardial infarction and other cardiovascular diseases, liver disease, diabetes mellitus type 1, systemic lupus erythematosus, biliary artesia, pancreatic necrosis, sarcoidosis, tuberculosis, and sepsis. It was discovered that nasal mucus levels of IL-18 are similar to plasma levels. Table 46.

Some embodiments of the invention include diagnosing a disease by detecting keratinocyte growth factor (KGF), also known as FGF7, a member of the fibroblast growth factor family. KGF is a paracrine-acting, epithelial mitogen produced by cells of mesenchymal origin and acts exclusively through a subset of FGF receptor isoforms (FGFR2b) expressed predominantly by epithelial cells. The upregulation of KGF after epithelial injury suggested it had an important role in tissue repair. Elevated levels of KGF are associated with breast cancer, inflammatory bowel disease and psoriasis. Decreased levels are associated with congenital lung abnormalities, alopecia greata, and ulcerative colitis. It was discovered that nasal mucus levels of KGF are approximately 5-fold higher than plasma levels ($p<0.005$), while KGF was undetectable in saliva. Table 46.

Some embodiments of the invention include diagnosing a disease by detecting L selectin, also known as CD62L, a cell adhesion molecule found on leukocytes. It belongs to the selectin family of proteins, which recognize sialylated carbohydrate groups. Elevated L selectin levels are associated with diabetes mellitus, and colon cancer. Decreased levels are associated with myocardial injury and those undergoing acute inflammatory processes. Nasal mucus levels of L selectin were not significantly different from plasma levels, while L selectin was not detected in saliva. Table 46.

Some embodiments of the invention include diagnosing a disease by detecting leptin, a 16 kDa protein hormone that plays a key role in regulating energy intake and energy expenditure, in part, by decreasing appetite and increasing metabolism. Administration of leptin intranasally is suggested to be the clinically beneficial manner to inhibit obesity. Leptin dosing can be monitored through nasal mucus sampling.

Some embodiments of the invention include diagnosing a disease by detecting leptin-receptor, a cellular receptor responsive to leptin with characteristics similar to insulin receptors.

Some embodiments of the invention include diagnosing a disease by detecting leukemia inhibitory factor (LIF), a member of the interleukin 6 family of cytokines. Functionally it has been implicated in many physiological processes including hematopoiesis, bone metabolism and inflammation. Some cell types known to express LIF include activated T cells, monocytes, astrocytes, keratinocytes, regenerating skeletal muscle, mast cells and fibroblasts. Elevated levels of LIF are associated with rheumatoid arthritis. Decreased LIF levels are implicated in deficiencies in placentation that result in early abortion, or pre-eclampsia and intrauterine growth restriction leading to impaired fetal health, including intrauterine growth retardation, prematurity and maternal death. LIF was detected in nasal mucus, but not in plasma, urine or saliva. Table 46.

Some embodiments of the invention include diagnosing a disease by detecting migration inhibitory factor (MIF), produced by activated macrophages where it sustains macrophage survival and function by suppressing activation-induced, p53-dependent apoptosis. Increased levels are associated with glomerulonephritis, metastatic prostate cancer, rheumatoid arthritis. Increasing levels of MIF may be prognostic for tumor growth including the development of lung cancer. Decreased serum MIF concentrations during early gestation were found in pregnant women suffering from recurrent miscarriage of fetuses with normal fetal chromosome karyotype. Decreased levels are also associated with septic shock and respiratory distress syndrome. It was discovered that MIF levels in nasal mucus are approximately 48-fold higher than in plasma ($p<0.001$), while MIF was not detectable in saliva or urine. Table 46. Some embodiments of the invention include diagnosing a disease by detecting matrix metalloproteinase 1 (MMP-1), also known as interstitial collagenase, a member of the MMP extracellular protease family. MMP-1 plays a critical role in extracellular matrix remodeling under both physiological and pathological conditions. Additional substrates include cytokines, chemokines, growth factors, binding proteins, cell/cell adhesion molecules and other proteinases. Increased levels of MMP-1 are associated with chronic peptic ulcers, caroitid atherosclerosis, oral lichen planus, oral carcinoma, aortic aneurysm, and esophageal cancer. Increasing levels of MMP-1 may be associated with poor prognosis of colon cancer patients. Decrease MMP-1 levels are associated with rheumatoid arthritis. Nasal mucus levels of MMP-1 were less than half of plasma levels, but the difference was not statistically significant. Table 46. MMP-1 was not detectable in saliva and urine.

Some embodiments of the invention include diagnosing a disease by detecting nerve growth factor (NGF), a three unit protein consisting of $\alpha$, $\beta$ and $\gamma$ subunits of which only the $\beta$ subunit is physiologically active. This is the 2.55 subunit which induces neurite outgrowth in various tissues.

Some embodiments of the invention include diagnosing a disease by detecting nitric oxide (NO), a signaling molecule produced from arginine by nitric oxide synthase. Endothelium cells release nitric oxide to signal surrounding smooth muscle to relax, resulting in vasodilation and increasing blood flow. NO is toxic to bacteria and other pathogens and is released by macrophages and neutrophils as part of the immune response. Increased levels of NO are associated with asthma and breast cancer. Decreased levels are associated with atherosclerosis and hypertension. NO is also used as a treatment for respiratory distress syndrome and pulmonary hypertension.

Some embodiments of the invention include prognosis a disease by detecting the inactive N-terminal fragment from pro-brain natriuretic peptide (NT-proBNP) that is co-secreted with brain natriuretic peptide (BNP). NT-proBNP serum levels are predictive of mortality among patients with acute coronary syndrome and serve as a prognostic marker in patients with stable coronary heart disease and acute congestive heart failure (CHF). NT-pro-BNP has been measured in serum samples of patients with acute and chronic coronary heart disease. NT-pro-BNP levels were significantly lower in patients who survived than among those who died with acute or chronic disease [120 pg/ml for survival vs 386 pg/ml for deaths ($p<0.001$)]. Patients with NT-pro-BNP levels in the highest quartile were older, had a lower left ventricular ejection fraction (LVEF), a lower creatinine clearance rate and were more likely to have a history of myocardial infarction, clinically significant coronary artery disease and diabetes than patients with NT-pro-BNP levels in the lowest quartile. The hazard ratio for death for patients with NT-pro-BNP levels in the highest quartile compared to those in the lowest quartile was 2.4 ($p<0.001$). This NT-pro-BNP level added prognostic information beyond that provided by conventional risk factors including patient age, sex, family history of ischemic heart disease, presence or absence of history of myocardial infarction, angina, hypertension, diabetes, chronic heart failure, creatinine clearance rate, body mass index, smoking status, plasma lipid levels, LVEF or the presence or absence of clinically significant coronary artery disease or angiography. Thus NT-pro-BNP levels can be used, not only as an acute marker, but also a marker of long-term mortality in patients with stable coronary heart disease and provides prognostic information above and beyond that provided by environmental cardiovascular risk functions and degree of left ventricular systolic dysfunction. Now, it may be possible to screen patients for NT-pro-BNP by sampling nasal mucus to provide a simple, rapid and low cost screening method to classify cardiac disease patients based on predicted mortality rate or prognosis and provide the appropriative therapeutic and support care based on the predicted mortality rate or prognosis.

Some embodiments of the invention include diagnosing a disease by detecting P selectin, also known as CD62P, Granule Membrane Protein 140 (GMP-140), or Platelet Activation-Dependent Granule to External Membrane Protein (PADGEM). P selectin is a cell adhesion molecule (CAM) found in granules in endothelial cells (cells lining blood vessels) and activated platelets. P-selectin is involved in the initial recruitment of leukocytes to injury sites during the initial inflammatory response. Elevated levels of P selectin are associated with atherosclerosis, hypertension, unstable angina, brain ischemia, diabetes mellitus, nasal polyposis, and tumor metastasis. Decreasing levels may be predictive of lung injury. It was discovered that P selectin levels in nasal mucus are approximately 5% of plasma levels ($p<0.001$). Table 46. P selectin was not detectable in saliva or urine.

The platelet derived growth factor (PDGF) family consists of PDGF-A, -B, -C and -D, which form either homo- or heterodimers. PDGF is the principal mitogen in serum for mesenchymal cells. Increased levels of PDGF-AA are associated with meningioma, and renal tissue injury. PDGF-AA can be used therapeutically for the treatment of chronic pressure ulcer, periodontal disease, non-healing wounds and pulmonary edema. Increased levels of PDGF-BB are associated with astrocytoma, and artheroma formation. Decreased PDGF-BB levels are associated with impaired wound healing of diabetic patients. Nasal mucus levels of PDGF-AA were slightly less than plasma levels, but the result was statistically significant. Table 46.

Some embodiments of the invention include diagnosing a disease by detecting placenta derived growth factor (PlGF), a member of the vascular endothelial growth factor (VEGF) family. PlGF exists in at least 4 different isoforms as a result of alternative splicing. It was first identified in human placenta and is expressed in various tissues including blood vessels, human umbilical vein, endothelia, bone marrow, uterine NK cells, and keratinocytes. PlGF is upregulated under specific pathological conditions including wound healing, tumor function and pregnancy. It is an indicator of for predicting the development of preeclampsia during pregnancy and may be present in blood up to 10 weeks prior to onset of symptoms of this disorder. We have discovered, for the first time, the presence of PlGF in nasal mucus. In plasma, PlGF ranged from 0-79 ng/ml (19.5±7.6, Mean±SEM) whereas in nasal mucus PlGF ranged from 0-1402 ng/ml (350±90). Table 49. PlGF concentration in saliva varied from 0-65 pg/ml (16.6±6.2) and urine from 0-84 pg/ml (23.3±9.4). These results indicate PlGF in nasal mucus is 18 times higher than in plasma, 21 times than in saliva and 15 times higher than in urine. This indicates that PlGF is found in significantly higher concentrations in nasal mucus than in other body fluids. Higher concentration coupled with the ease of measurement and patient comfort and acceptance makes PlGF a more useful marker of PDF than is any other body fluid.

Furthermore, PlGF was found in nasal mucus in 94% of patients, but in plasma in only 65% of patients, in saliva in only 59% of patients and in urine in only 67% of patients. Thus, measurement of PlGF in nasal mucus is a significantly more reliable measurement than is plasma, saliva or urine ($X^2$, $p<0.01$).

These findings suggest that nasal mucus concentration of PlGF can be measured alone or in tandem with endoglin to predict the occurrence of preeclampsia prior to its onset of clinical symptomology. Through nasal mucus testing for biomarkers for the development of preeclampsia, it may be possible to intervene before symptoms manifest and thereby ameliorate or avoid fetal growth restriction, appearance of the HELP syndrome (hemolysis, elevated liver enzymes and low platelets) and potential fetal wastage associated with preeclampsia. It is critical to note that levels of endoglin and PGF were not elevated in patients who were destined to have gestational hypertension or to remain normotensive but deliver growth-restricted neonates.

Endoglin and PlGF can be measure individually or in combination using nasal mucus as a diagnostic test for preeclampsia. With combination testing, separate diagnostic devices can be used or the two substances can be tested simultaneously on the same device. Nasal mucus can be sampled by the direct placement of a swab or similar sampling device directly into one nasal naris. The collected nasal mucus can be transferred to a diagnostic device. Alternatively, nasal mucus can be collect using a swab or other collection means that is engineered into a diagnostic device. The device will have one or more substances that react with one or more biological substances present in nasal mucus. In one embodiment, the reactive substances are antibodies to endoglin and PlGF. Upon application to the device or collection of nasal mucus with the device, the biologic substances of interest will react directly with the reactive substances and over the course of several minutes of the reaction, a colorimetric result will be readable. The device may further include a biologic substance reactive with a ubiquitously occurring nasal mucus substance so as to produce a positive control signal demonstrating the correct functioning of the assay device. The simple colormetric readout of the device will allow non-professional or low-skilled health personnel in any environment, developed or non-developed countries, to obtain rapid, specific quantitative measurements of both endoglin and PlGF without use of any external equipment. This will allow the prediction of the occurrence of preeclampsia at least 10 weeks prior to the onset of symptoms of this pathology.

Some embodiments of the invention include diagnosing a disease by detecting receptor for abdominal glycation end (RAGE) products, a multi-ligand transmembrane glycoprotein belonging to the immunoglobulin superfamily. RAGE ligands include advanced glycation end products (AGEs) amyloid-13 and several members of the S-100 protein superfamily. Elevated levels of RAGE are associated with Alzheimer's disease, diabetes nephropathy, glomerulosclerosis, and macular degeneration. Increasing levels of RAGE may be predictive for diabetes and peripheral vascular disease. Table 46.

Some embodiments of the invention include diagnosing a disease by detecting stem cell factor (SCF) also known as KIT ligand or Steel factor. SCF is a cytokine that binds CD117 (c-Kit). SCF is an important growth factor for the survival, proliferation, and differentiation of hematopoietic stem cells and other hematopoietic progenitor cells. Increased levels of SCF are associated with breast cancer, testicular cancer, gynecological cancers, leukemia, and cutaneous mastocytosis. It was discovered that nasal mucus levels of SCF were approximately 4% of plasma levels (p<0.001). Table 46.

Some embodiments of the invention include diagnosing a disease by detecting substance P, an 11 amino acid peptide that belongs to the tachykinin neuropeptide family. It is synthesized as a large protein and the enzymatically converted to its active form. Substance P is widely distributed in the central and peripheral systems where it acts as a neurotransmitter. In the peripheral nervous system it is localized to primary sensory neurons and neurons intrinsic to the gastrointestinal tract. Increased levels of Substance P are associated with fibromyalgia, pancreatitis, Raynaud's phenomena, and Rheumatoid arthritis. Decreased levels are associated with psoriasis. It was discovered that nasal mucus levels of substance P were similar to plasma levels and about twice the level found in saliva. Table 46.

Some embodiments of the invention include diagnosing a disease by detecting tissue inhibitor of metalloproteinase (TIMP-1), one member of a group of five TIMPs, each of which is capable of inhibiting almost every member of the matrix metalloproteinases. Increased levels of TIMP-1 are associated with breast, colon, and gastric cancer. Increasing levels of TIMP-1 are associated with poor prognosis in patients with breast, colon or gastric cancer. It was discovered that nasal mucus levels of TIMP-1 were approximately 10-fold higher than plasma levels (p<0.001) and 20-fold higher than saliva levels (p<0.001). Table 46.

Some embodiments of the invention include diagnosing a disease by detecting transforming growth factor alpha (TGFα), a member of the EGF family of cytokines. TGFα plays a role in cell-cell adhesion and in juxtacrine stimulation of adjacent cells. Its expression is widespread in tumors and transformed cells. It is expressed in normal tissues during embryogenesis and in adult tissues including pituitary, brain, keratinocytes and macrophages. Increased levels of TGF-α are associated with various cancers including squamous cell cancer of the head and neck, breast cancer, esophageal cancer, colon cancer and liver cancer. It was discovered that TGF-α was detectable in nasal mucus, but was undetectable in plasma, saliva or urine. Table 46.

Some embodiments of the invention include diagnosing a disease by detecting transforming growth factor-β (TGF-β). TGF-β acts as a potent growth inhibitor for most types of cells. Decreased levels of TGF-β associated with the formation of cleft palate and abnormal neonatal lung development. Increased levels may be predictive for the development of renal disease including renal fibrosis. It was discovered that nasal mucus levels of TGF-β were over twice plasma levels (p<0.05) and also over twice saliva levels. Table 46.

Some embodiments of the invention include diagnosing a disease by detecting triggering receptor expressed on myeloid cells (TREM-1), a cell surface molecule on neutrophils and monocytes/macrophages implicated in the amplification of inflammatory responses by enhancing degranulation and secretion of proinflammatory mediators. Increased levels of TREM-1 are associated with septic shock, sepsis, acute pancreatitis, and pneumonia.

Some embodiments of the invention include diagnosing a disease by detecting tumor necrosis factor (TNF), also known as cachexin or cachectin and formally known as tumor necrosis factor-alpha) is a cytokine involved in systemic inflammation and is a member of a group of cytokines that stimulate the acute phase reaction. Increased levels of TNF are associated with psoriasis, rheumatoid arthritis, Crohn's disease, glomerulonephritis, Parkinson's disease, head injury including ischemic brain injury, and dementia. Increased levels of TNF may be predictive for the development of insulin resistance. It was discovered that nasal mucus levels of TNF were approximately 65% of plasma levels and over 5-fold higher than saliva levels. Table 46. TNF levels in nasal mucus are elevated almost 6-fold in post influenza patients almost 7-fold in post surgery patients.

Some embodiments of the invention include diagnosing a disease by detecting tumor necrosis factor beta (TNFβ), also known as lymphotoxin alpha (LTα). TNFβ binds to cell surface receptors and produces a vast range of effects. Increased levels of TNFβ are associated with B cell lymphomas and multiple sclerosis. Table 46.

Some embodiments of the invention include diagnosing a disease by detecting tumor necrosis factor receptor 1 (TNF-R1) is also known as P55/P60 TNFR. TNF-R1 is a high affinity receptor for TNFα and β. It is involved in the mediation of multiple aspects of inflammatory immune response. TNF-R1 forms homodimers on oligomers upon ligand binding. Monomers have an extracellular domain which includes four cysteine rich repeats. Increased levels of TNF-R1 are associated with obesity, rheumatoid arthritis, and chronic inflammatory diseases. It was discovered that nasal mucus levels of TNF-R1 are approximately 60% of plasma levels (p<0.01), but are almost 8-fold higher than saliva levels. Table 46. Elevated nasal mucus levels were noted in patients with head injury or those that are post influenza.

Some embodiments of the invention include diagnosing a disease by detecting tumor necrosis factor receptor 2 (TNF-R2) is also known as P75/P80 TNFR. TNF-R2 is a receptor protein in the same family as TNFR1 with some similar characteristics to TNFR1. Increased levels of TNF-R2 are associated with idiopathic pulmonary fibrosis and may be predictive of insulin resistance. Decreased levels may be predictive of liver disease. It was discovered that TNF-R2 levels in nasal mucus are approximately 50% of plasma levels, but over 9-fold higher than saliva levels. Table 46. Elevated levels of TNF-R2 were discovered in patients with allergic diseases or oral burns.

Some embodiments of the invention include diagnosing a disease by detecting TNF-related apoptosis-inducing ligand (TRAIL) is also known as apo-2 ligand and TNFSF-10. It is a type of Type II transmembrane protein with a carboxy terminal extracellular domain that exhibits homology to other TNF superfamily members. It is the most homologous to FAS-ligand sharing 28% amino acid identity. It reflects an end product of cellular apoptosis. Patients with allergic diseases and those post surgery had elevated nasal mucus levels.

Some embodiments of the invention include diagnosing a disease by detecting vascular cell adhesion molecule (VCAM1), a member of the immunoglobulin superfamily. It is a cell surface protein expressed by activated endothelial cells and certain leukocytes such as macrophages. Expression of VCAM1 is induced by IL-1β, IL-4, TNFα and IFN-γ. It binds to leukocyte integrins; VLA-4 and integrin α2 β7. Elevated levels of VCAM1 may be predictive of early atherosclerosis and the development of lupus nephritis. Nasal mucus levels of VCAM1 were approximately 11% of plasma levels and similar to saliva levels. Table 46.

Some embodiments of the invention include diagnosing a disease by detecting members of the vascular endothelial growth factor (VEGF), family. This family is related to PlGF and modulates various physiological and pathological processes including vasculogenesis, angiogenesis and lymphangiogenesis.

One VEGF family member is VEGF-C, also known as Flt4 ligand is an important and specific regulatory factor for lymphatic endothelial proliferation and lymphangiogenesis. Increased levels are associated with prostate cancer.

Increased or increasing levels of VEGF-C may be predictive of breast, gastric, and head and neck cancer metastasis. It may also be predictive for the development of colon cancer. It was discovered that VEGF-C levels in nasal mucus are approximately 10-fold higher than plasma levels (p<0.001) and approximately 9-fold higher than saliva levels. Table 46.

Another VEGF family member is VEGF-D, an important and specific regulatory factor for lymphatic endothelial proliferation and lymphangiogenesis. Increased VEGF-D serum levels are significantly elevated in patients with angiosarcoma. Increased or increasing levels of VEGF-D may be predictive of tumor metastasis in the lymphatic system and of ovarian cancer metastasis. It was discovered that nasal mucus levels of VEGF-D are approximately 6% of plasma levels (p<0.001), but over 4-fold higher than saliva levels. Table 46.

Some embodiments of the invention include diagnosing a disease by detecting vascular endothelial growth factor receptor 1 (VEGFR1). VEGFR1 binds VEGF-A and is thought to modulate VEGFR-2 signaling. VEGFR1 is a member of the class III superfamily of receptor tyrosine kinases (RTKs). All receptors contain 7 immunoglobulin-like repeats in their extracellular domains and kinase insert domains in their intracellular region. They regulate VEGF mediated vasculogenesis, angiogenesis and lymphangiogenesis. They also mediate neurotrophic activity and regulate hematopoietic development. Increased or increasing levels of VEGFR1 may be prognostic for endometrial cancer. It was discovered that nasal mucus levels of VEGF-R1 are approximately 4-fold higher than plasma levels and 3-fold higher than saliva levels. Table 46.

Some embodiments of the invention include diagnosing a disease by detecting vascular endothelial growth factor receptor 2 (VEGFR2). Increased or increasing levels of VEGFR2 may be prognostic for oxygen induced retinopathy and vascular retinopathy. It was discovered that nasal mucus levels of VEGFR2 are approximately 7% of plasma levels (p<0.001), but 3.5-fold higher than saliva levels. Table 46.

Trace elements can also be measured in nasal mucus. Wilson's disease, also known as hepatolenticular degeneration is an example of a disease that can be diagnosed and/or prognosed through nasal mucus sampling. Table 47. Wilson's disease is an autosomal recessive disorder wherein copper accumulates in tissue in resulting in liver disease and neurological symptoms including taste and smell deficits. Wilson's disease is currently diagnosed by measuring ceruloplasmin in blood. Over 80% of Wilson disease patients have suppressed levels of ceruloplasmin, typically about 30% of normal. More accurate measurements can be obtained by assaying urine, blood or a liver biopsy sample for copper. Of particular importance is the observation that increased tissue levels of copper is predictive of the later development of Wilson's disease in 95-100% of the individuals tested. Additionally, abnormal copper levels can be observed one to ten years before symptoms appear allowing treatment with chelating agents to reduce tissue levels of copper and prevent future build up along with instructions to follow a low-copper diet.

It was discovered that patients with Wilson's disease have abnormally low levels of copper in their nasal mucus, with an approximately 50-fold reduction compared to controls, 2±1 (mg/l) and 99±8 (mg/l), respectively. Table 50.

Patients with other taste and smell deficits appear to have increased copper levels in their nasal mucus, saliva and urine compared to control. Table 50. Nasal mucus sampling for copper represents a simple, non-invasive technique that can be used to screen, or prognose for the development of Wilson's disease in addition to diagnosing the disease.

Zinc is another element that is associated with taste and smell loss. In patients with a taste and smell deficit that is not attributable to Wilson's disease, nasal mucus contain over twice the level of zinc at 236±37 (mg/l) compared to controls at 96±10 (mg/l). Table 51. Again, nasal mucus represents a simple, non-invasive technique to ascertain trace element levels in a patient.

Measurement Techniques

We have measured these substances in blood, urine, saliva and nasal mucus using a 96 plate colorimetric ELISA procedure. This procedure, while very sensitive, is complex, time consuming and requires special equipment for performance of the procedure. We plan to reduce this complex technique to a point-of-care (POC) nasal swab test. For this technique we intend to insert a nasal swab directly into the nose, the swab coated as noted below such that the presence of nasal mucus in the nose will provide the antigen for the POC test. We would also develop a test such that secreted nasal mucus could be deposited directly onto the swab and the colorimetric POC test performed outside of the body directly on the swab. By use of this technique we will measure these prognostic, diagnostic substances independent of blood in a safe, rapid and powerful manner to screen patient with these potential disorders worldwide and thereby, with the initiation of appropriate therapy, utilize these diagnostic techniques to ward off onset of symptoms of these diseases prior to the onset of the full-blown disease pathology.

We have been involved in the development of a simplified ELISA procedure in which the nasal swab contains all the necessary colorimetrics to perform an ELISA procedure. There are several procedures we have been developing to perform this test. One such procedure involves a lateral-flow immunoassay rapid strip test (6). This technique has been used previously in several diagnostic test devices and can be adapted to use quantum dots, SNP detection, nucleic acid detection, hexapet and other novel labeling techniques. This embodies a chromatographic device which employs nanoparticles of antibody coated with materials that bind to the analyte to be measured (in nasal mucus) within the specified environment of the nasal swab. The analyte-nanoparticle complex flows laterally through a series of overlapping membranes until it is captured on the antibody line achieving a specific antigen-antibody complex. A visual result, eliciting a color is achieved within a few minutes. A control line is always available to define specificity. Even an unskilled operator can readily interpret the test results on a semi-quantitative basis without any need for complex or expensive equipment. We plan to adapt this general technique to a swab (plastic or some similar structure) which we will place into the nose to read the reaction directly on the swab or to take expelled nasal mucus and apply it directly onto the swab (as noted above) to read the reaction independent of the nose per-se. These adaptations involve novel technology which is part of this new art and will allow rapid and simple substance identification using adaptations of the current available devices. By use of this new technology which we are proposing in this application we intend to demonstrate that many substances using present day technology are present in nasal mucus at levels below the threshold for present day determination. We intend to demonstrate that this new technology we propose will allow identification of these substances in nasal mucus by use of a combination of amplification methods. One method for accomplishing this is to use a combination which will include both immunoassay and PCR methodologies which can detect substances in nasal mucus at a sensitivity approximately that of detection of nucleic acids. This technique is embodied in a modification of a prior technique called immuno-PCR (IPCR) which was first described in 1992 (7). By this modification we project that we can detect all necessary diagnostic substances in nasal mucus by adsorbing the required substance (as the antigen) onto microtiter plate wells through contact with a series of substances—antibody, followed by protein A avidin chimera and then by biotinylated plasmid DNA. Detection will be amplified by eliminating the background signal which previously limited sensitivity. The details of this procedure and others that may also be used will be subjects of other applications since the purpose of this application is to present mainly the use of nasal mucus and the substances contained therein as prognostic, diagnostic indicators for the diagnosis of human physiology, pathology and disease.

Examples of Diseases

Without limiting the scope of the present invention, the examples of some of the diseases which can be diagnosed by detecting the biological substance, is provided herein. However, these examples are not intended to limit the scope of the invention. The disease as provided herein include, infections, hematological disorders, oncological disorders, endocronological disorders, metabolic disorders, immunological disorders, neurological disorders, vascular disorders, mast cell disorders, psychiatric disorders, neoplastic disorders, nutritional disorders, post irradiation disorders, and changes in the trace metal metabolism.

Infectious diseases include acute and chronic parasitic and/or infectious diseases from bacterial, viral or fungal sources, but are not limited to, single or multiple cutaneous lesions, mucosal disease, chagas' disease, toxoplasmosis, leishmaniasis, trypanosomiasis, shistosomiasis, cryptosporidiosis, *mycobacterium avium* infections, leprosy, dengue, yellow fever, inner ear infections, urinary tract infections, bacterial endocarditis, osteomyelitis, *h. pylori* associated ulcers, antibiotic associated colitis, sexually transmitted diseases, malaria, rheumatoid arthritis, inflammatory bowel disease, interstitial cystitis, fibromyalgia, autonomic nervous dysfunction, pyoderma gangrenosum, chronic fatigue, chronic fatigue syndrome, sepsis syndrome, cachexia, circulatory collapse and shock resulting from acute or chronic bacterial infection, AIDS (including symptoms of cachexia, autoimmune disorders, AIDS dementia complex and infections), wegners granulomatosis, aneurysms, hemorrhoids, sarcoidosis, chronic inflammatory bowel disease, Crohn's disease, vascular inflammatory pathologies, such as, but not limited to, disseminated intravascular coagulation, atherosclerosis, and Kawasaki's pathology, inflammatory diseases such as coronary artery disease, hypertension, stroke, asthma, chronic hepatitis, multiple sclerosis, peripheral neuropathy, chronic vascular headaches (including migraines, cluster headaches, and tension headaches), demyelinating diseases, such as multiple sclerosis and acute transverse myelitis, extrapyramidal and cerebellar disorders, such as lesions of the corticospinal system, disorders of the basal ganglia or cerebellar disorders, hyperkinetic movement disorders such as Huntington's chorea and senile chorea, drug-induced movement disorders, such as those induced by drugs which block CNS dopamine receptors, hypokinetic movement disorders, such as Parkinson's disease, progressive supranucleo palsy, cerebellar and spinocerebellar disorders, such as astructural lesions of the cerebellum, spinocerebellar degenerations (spinal ataxia, Friedreich's ataxia, cerebellar cortical degenerations, multiple systems degenerations (mencel, Dejerine-Thomas, Shi-Drager, and Machado Joseph)), systemic disorders (Refsum's disease, abetalipoprotemia, ataxia, telangiectasia, and mitochondrial multi-system disorder), disorders of the motor unit, such as neurogenic muscular atrophies (anterior horn cell degeneration, such as amyotrophic lateral sclerosis, infantile spinal muscular atrophy and juvenile spinal muscular atrophy), Alzheimer's disease, Down's Syndrome in middle age, diffuse Lewy body disease, senile dementia of lewy body type, Wernicke-Korsakoff syndrome, chronic alcoholism, Creutzfeldt-Jakob disease, subacute sclerosing panencephalitis, Hallerrorden-Spatz disease, and Dementia pugilistica, dermatophytosis (e.g., trichophytosis, etc), pityriasis versicolor, candidiasis, cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, mycotic keratitis, otomycosis, and pneumocystosis.

Ocular neovascularization, psoriasis, duodenal ulcers etc can also be treated when demonstrated by the diagnostic procedures described herein. Similarly, other diseases (their biological substances in parenthesis), include, but not limited to, neutropenia, gout, dwarfism or congenital short stature (growth hormone releasing hormone (GHRH)); congestive heart disease (atrial natriuretic peptide or factor (ANP or ANF)); osteoporosis (parathyroid hormone (PTH)); Paget's disease (calcitonin); accromegally, insulin sparing effects, treatment of long term complications of diabetes and treatment of various endocrine secreting tumors (somatostatin); Addison's Disease and Cushing's Syndrome, shipping fever (bovine respiratory syndrome) or ulcers, and stress-induced immunosuppression (corticotrophin releasing factor (CRF)); contraception, fertility control, suppression or interruption of heat, treatment of ovarian cysts, precocious puberty, prostatic hyperplasia and tumors, gynecologic diseases, and termination of pregnancy (luteinizing hormone-releasing hormone (LHRH)); aplastic anemia, paroxysmal nocturnal hemoglobinurea, chronic myelocytic leukemia, polycythemia vera, essential thrombocythemia, myelofibrosis, myelodysplastic syndrome and acute leukemia; and hematological diseases such as megaloblastic anemia, AIDS, multiple myeloma, metastatic cancer of the bone marrow, and drug-induced myelosuppression (hematopoietic stem cell growth factor (SCGF)); body weight disorders, including obesity, cachexia, and anorexia, and diabetes, neoplasms, and hyperamylinemia (agouti-related protein); impairment of functions, increased ceramide formation, which triggers nitric oxide-mediated lipotoxicity and lipoapoptosis, obesity and hyperphagia (leptin); hypolipidimia, coronary heart disease, Niemann Pick Disease, Gaucher's disease, Batten's syndrome, Farber's lipogranulomatosis, Krabbe's disease, metachromic leukodystrophy, Tay-Sach's disease, GM1 gangliosidoses, Fabry's disease, cystinosis, aspartylglycosaminuria (lipid profile which includes triglycerides, LDL-cholesterol and HDL-cholesterol), and generalized vascular disease, chronic hyperglycemia, obesity, hypertension, atherosclerosis and heart disease, carbohydrate deficient glycoprotein syndrome type 1a, glycogenoses, and galactosemia (carbohydrates).

Detection of the concentration of the caspases in the nasal secretion can provide diagnosing a disorder or selection of therapeutic strategies involving, e.g., inappropriate apoptosis and/or excessive cell proliferation, such as an inflammatory disease, a neurodegenerative disease, cancer, a cardiovascular disease and, any disorder or disease characterized by a gradual and prolonged development of apoptosis. Apoptosis functions in maintaining normal tissue homeostasis in a variety of physiological processes including embryonic development, immune cell regulation, normal cellular turnover and programmed cell death of cancer cells. Thus, the dysfunction or loss of regulated apoptosis can lead to a variety of pathological disease states. For example, the loss of apoptosis can lead to the pathological accumulation of self-reactive lymphocytes such as occurs in many autoimmune diseases. Inappropriate loss of apoptosis can also lead to the accumulation of virally infected cells and of hyperproliferative cells such as neoplastic or tumor cells. Inappropriate activation of apoptosis can contribute to a variety of diseases such as AIDS, neurodegenerative diseases and ischemic injury.

Dysregulation of apoptosis has been implicated in numerous diseases such as neurodegenerative disorders including Alzheimer's disease, Parkinson's disease, Huntington's disease, and amyotrophic lateral sclerosis (ALS), cerebellar degeneration, stroke, traumatic brain injury, CNS ischemic reperfusion injury including neonatal hypoxic-ischemic brain injury or myocardial ischemic-reperfusion injury, injury caused by hypoxia, cardiovascular diseases (e.g., myocardial infarction), especially those which are associated with apoptosis of endothelial cells, degenerative liver disease, multiple sclerosis, rheumatoid arthritis, hematological disorders including lymphoma, leukemia, aplastic anemia, and myelodysplastic syndrome, osteoporosis, polycystic kidney disease, AIDS, myelodysplastic syndromes, aplastic anemia and baldness. Diseases of the eye include glaucoma, retinitis pigmentosa and macular degeneration.

Inflammatory disease states include systemic inflammatory conditions and conditions associated locally with migration and attraction of monocytes, leukocytes and/or neutrophils. Inflammation may result from infection with pathogenic organisms (including gram-positive bacteria, gram-negative bacteria, viruses, fungi, and parasites such as protozoa and helminths), transplant rejection (including rejection of solid organs such as kidney, liver, heart, lung or cornea, as well as rejection of bone marrow transplants including graft-versus-host disease (GVHD)), or from localized chronic or acute autoimmune or allergic reactions. Autoimmune diseases include acute glomerulonephritis; rheumatoid or reactive arthritis; chronic glomerulonephritis; inflammatory bowel diseases such as Crohn's disease, ulcerative colitis and necrotizing enterocolitis; granulocyte transfusion associated syndromes; inflammatory dermatoses such as contact dermatitis, atopic dermatitis, psoriasis; systemic lupus erythematosus (SLE), autoimmune thyroiditis, multiple sclerosis, and some forms of diabetes, or any other autoimmune state where attack by the subject's own immune system results in pathologic tissue destruction. Allergic reactions include allergic asthma, chronic bronchitis, acute and delayed hypersensitivity. Systemic inflammatory disease states include inflammation associated with trauma, burns, reperfusion following ischemic events (e.g. thrombotic events in heart, brain, intestines or peripheral vasculature, including myocardial infarction and stroke), sepsis, ARDS or multiple organ dysfunction syndrome. Inflammatory cell recruitment also occurs in atherosclerotic plaques.

Examples of pathological conditions resulting from increased cell survival include cancers such as lymphomas, carcinomas and hormone-dependent tumors (e.g., breast, prostate or ovarian cancer). Abnormal cellular proliferation conditions or cancers that may be treated in either adults or children include solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, astrocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Karposi's sarcoma.

Viral infections that may be detected include infections caused by herpesviruses (including CMV, HSV-1, HSV-2, VZV, EBV, HHV-6, HHV-7 and HHV-8), paramyxoviruses (including parainfluenza, mumps, measles, and respiratory syncytial virus (RSV)), picornaviruses (including enteroviruses and rhinoviruses), togaviruses, coronaviruses, arenaviruses, bunyaviruses, rhabdoviruses, orthomyxoviruses (including influenza A, B and C viruses), reoviruses (including reoviruses, rotaviruses and orbiviruses), parvoviruses, adenoviruses, hepatitis viruses (including A, B, C, D and E) and retroviruses (including HTLV and HIV). Treatments of both acute and chronic infection are contemplated.

Adenylyl cyclases are a family of enzymes that catalyze the formation of Adenosine-3':5-cyclic monophosphate (cAMP) from adenosine-5'-triphosphate (5'ATP), mediate the physiological effects of numerous hormones and neurotransmitters, and belong to a super family of membrane-bound transporters and channel proteins. Adenosine-3':5'-cyclic monophosphate (cAMP) is the second messenger involved in signal transduction for numerous neurotransmitters and hormones, and thus may have an impact upon some of the mediators for smooth muscle cells (SMC) proliferation and migration. Many hormones and other substances may activate cAMP and may activate the subsequent signaling cascades via their indirect influence on adenylyl cyclase. cAMP is a growth factor for neurite growth and is involved in development in tissue culture of sympathetic ganglion cells similar to the action of NGF. Adenylyl cyclase is a growth factor which acts on stem cells in taste buds and olfactory epithelium to induce growth and development of all cell types in taste buds and olfactory epithelium. cGMP, guanosine 3',5"-cyclic monophosphate is formed by the action of guanylyl cyclase on GTP. cGMP is present at levels typically lower than cAMP in most tissues. Hormones, such as insulin and oxytocin as well as other substances including acetylcholine, serotonin and histamine may increase cGMP levels. Stimulators of cGMP may include vasodilators and peptides that relax smooth muscle.

Adenylyl cyclases also play a role in the disease progression of Congestive heart failure (CHF). CHF is defined as an abnormal heart function resulting in an inadequate cardiac output for metabolic needs. Heart failure is usually not recognized until a more advanced stage of heart failure which is referred to as congestive heart failure. On physical examination, patients with CHF tend to have elevations in heart and respiratory rates, rates (an indication of fluid in the lungs), edema, jugular venous distension, and, in general, enlarged hearts. The most common cause of CHF is atherosclerosis which causes blockages in the blood vessels (coronary arteries) that provide blood flow to the heart muscle. Ultimately, such blockages may cause myocardial infarction (death of heart muscle) with subsequent decline in heart function and resultant heart failure.

Fibroproliferative vasculopathy includes restenosis following coronary bypass surgery and PTCA (percutaneous transluminal coronary angioplasty), allograft arteriosclerosis in chronic allograft rejection, diabetic angiopathy and all forms of common arteriosclerosis. Vascular intimal dysplasia and remodeling are characteristic features of reinjury following balloon angioplasty, coronary bypass surgery and in chronic allograft rejection. An initial response to vascular injury is inflammatory and involves attraction of lymphocytes, macrophages and thrombocytes to the site of injury and secretion of cytokines, eicosanoids and growth factors. Under the influence of growth factors and cytokines, smooth muscle cells (SMC) may proliferate and migrate from the media to the intima and contribute to intimal hyperplasia and stenosis. cAMP has an impact upon some of the key mediators for SMC proliferation and migration.

Glucose is irreversibly oxidized within the cells to produce water and carbon dioxide. In the presence of a catalyst, especially a carbonic anhydrase enzyme (of which several forms exist, of which the form present depends upon the type of tissue cells present), the water and carbon dioxide may reversibly produce a hydrogen ion and a bicarbonate ion. Hydrogen ion produced by carbonic anhydrase enzymes can be acted upon by cytochrome system, which can then be utilized as the energy source of the ion pump that maintains the integrity of the cell membrane comprising and enclosing each cell. It can also be a source of the brain's electric current. Disruption of the process may cause depolarization of the cell wall membrane, hence sodium (Na), water, and other chemicals can enter the cell in uncontrolled amounts and potassium (K) can exit uncontrollably, leading to the death and destruction of the involved cells followed by cellular edema. As this edema progresses, the cell dies. Along with the progressive and gradual death of cells, gliosis may follow resulting in the aging in the brain. The deficiency of carbonic anhydrase can cause conditions of aging associated with a decreased presence of cell-specific carbonic anhydrase enzymes in the brain, such as chronic neurodegenerative conditions including dementia such as Alzheimer's disease, or showing other forms of dementia or neurodegenerative diseases.

Methods of Treatment

The substances secreted into saliva and nasal mucus act on local oral and nasal tissues, respectively, to induce physiological effects. There are several effects of gland secretion at distant sites: (1) endocrine-secretions from a gland and subsequent action at a distant site, the secretion carried in blood to the distant site; (2) paracrine-secreted substances act at a distant site within the local reach of the fluid; (3) exocrine-secretions from a gland which have direct local effects, e.g, β-cells in the pancreas which act directly to secrete insulin in response to local changes in blood glucose. This is a one directional effect, a secretion from the gland, into the biological fluid, acting at a distant but local site.

There are feedback mechanisms such that whatever effects the gland secretion had on its receptor, the receptor also interacted with the site of secretion. For example, increased glucose induces increased secretion of insulin but as insulin secretion increases, insulin receptor number in liver and pancreas change in response to the increased insulin secretion. This feedback concept can also be exemplified by brain secretion of peptide hormones which acted as master feedback mechanisms to control peripheral hormone secretion. Thus, there are interactions between brain, gland and a receptor with the interactions proceeding in both directions. For example, TRH secreted from the brain hypothalamus stimulates pituitary TSH which acts to stimulate thyroid $T_3$ and $T_4$ which can act back on both pituitary and brain in the form of both long (to brain) and short (to pituitary) feedback loops.

Figure 11:
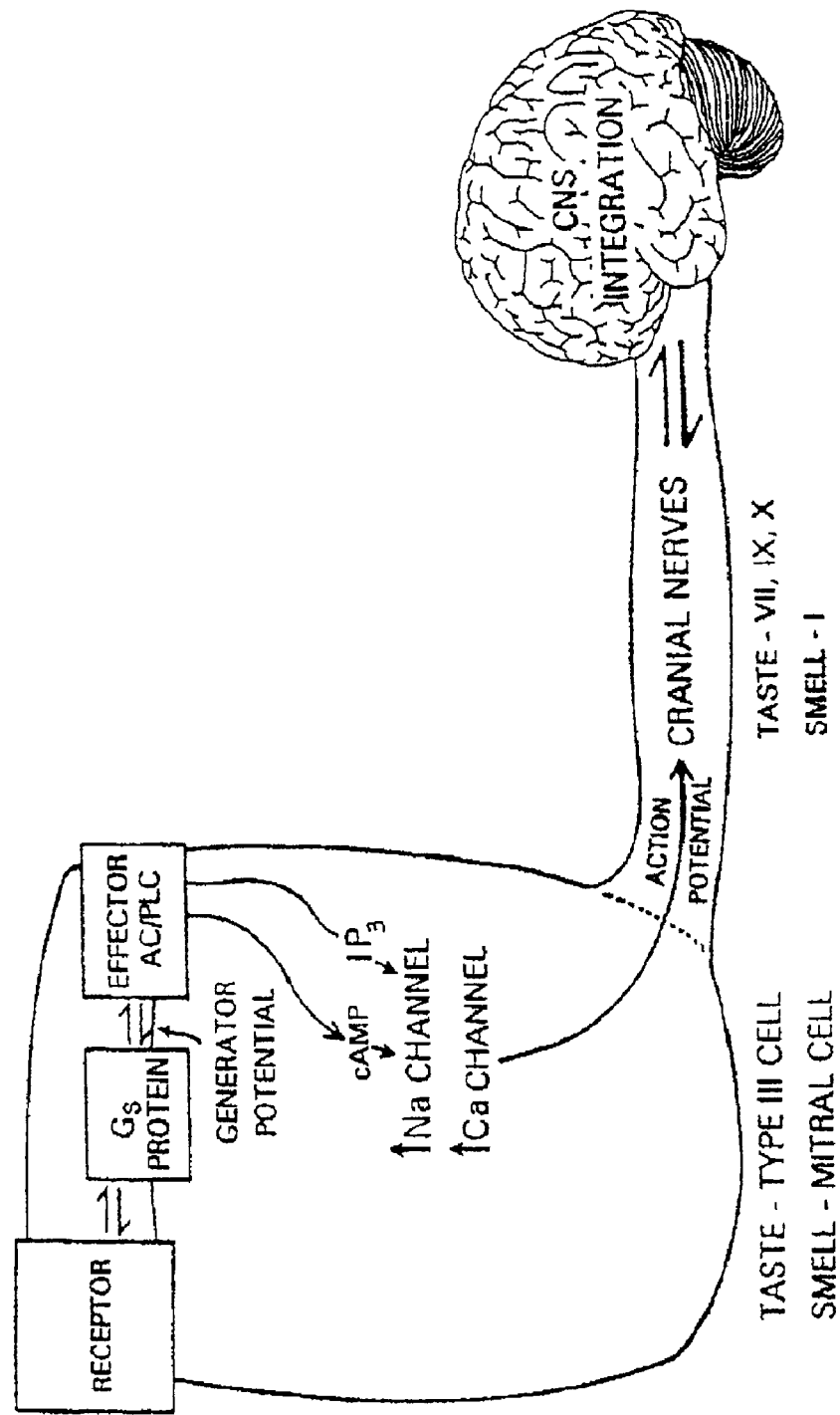
FIGS. 11 and 12 reflect a feedback mechanism with effects acting from nose to brain and from brain to nose.
Figure 12:
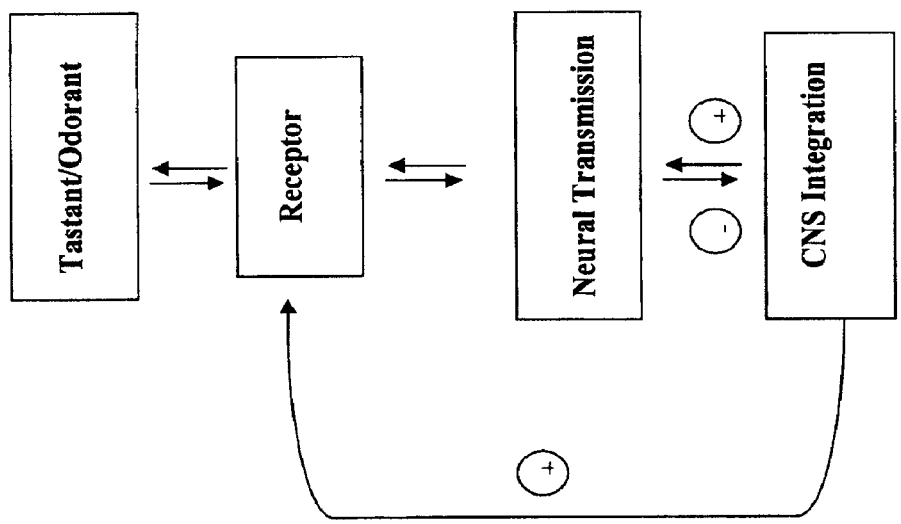

Henkin, R. I., Olfaction and Taste XI, (Kurihara, K., Suzuki, N., Ogawa, H., Eds.), Springer Verlag, 1994, pp. 568-573, incorporated herein by reference in its entirety, described the concept involving saliva and nasal mucus secretions related to taste and smell function (FIGS. 11 and 12). These results suggest that tastants and odorants affect brain function and vice versa. Since saliva and nasal mucus are the critical factors in maintaining the taste and smell systems, respectively, it is understandable that substances in these fluids also affect brain function and vice versa. Therefore, nasal administration of substances can affect brain function and thereby affect various physiological and pathological problems. For example, nasal administration of leptin (to control obesity), agouti-related protein (to increase appetite in anorexic patients), glucose, albumin, insulin (to treat diabetes), hormones (hormonal disorders), etc.

These effects may act through the large arteriovenous plexus of blood vessels in the nose such that absorption of the substances may be enhanced by direct contact and absorption through these exposed vessels. FIGS. 11 and 12 reflect a feedback mechanism with effects acting from nose to brain and from brain to nose, as in both a short and long loop feedback system.

Treatment with Drug

Theophylline treatment restores smell function in some patients with hyposmia (loss of smell). Theophylline is a phosphodiesterase (PDE) inhibitor; it restores smell function through PDE inhibition thereby increasing cAMP, a growth factor which stimulates maturation of olfactory epithelial stem cells, cells whose functions are inhibited among patients with hyposmia. Theophylline may also restore smell function through other mechanisms. One such mechanism may operate through inhibition of excessive apoptosis, a normal process which, if excessively increased, can become pathological and impair cellular anatomy of the olfactory epithelium and cause hyposmia.

Table 16 illustrates detection and measurement of TRAIL in nasal mucus in patients with hyposmia before and after treatment with theophylline at various doses. Data indicated that treatment with theophylline which returned smell function to normal in a dose-dependent manner was associated with a dose-dependent decrease in TRAIL. These data indicate that treatment with a drug demonstrated a dose dependent decrease in TRAIL which indicates a decrease in the abnormal apoptotic processes. These data also indicate both a biochemical and functional improvement in smell function by treatment with theophylline. Without limiting the scope of the present invention, other drugs are also considered with in the scope of the present invention for the treatment of various diseases. This is one of the example of the multiple examples of drugs to treat disease in which changes of various substances found in nasal mucus reflect biochemical normalization and functional improvement in the disease process.

Table 33 in the examples illustrates NO in nasal mucus in patients treated with theophylline in various doses before and after drug treatment. NO levels in nasal mucus changed following the treatment of patients with smell loss. Results show treatment of patients with graded increasing doses of theophylline and measurement of both smell function and NO in nasal mucus in patients with hyposmia. Results indicated that prior to the treatment levels of NO in nasal mucus were lower than in normal subjects. After treatment with theophylline in graded doses there were increases in nasal mucus NO associated with graded increases in smell function. These data demonstrate that treatment with drugs that increase smell function to or toward normal, returns smell function to normal. These results demonstrate the measurements of various substances in nasal mucus as an index of both human physiology and pathology of various diseases. Its continual measurement during treatment of the disorders helps in monitoring efficacy of therapy. The detection of NO in nasal mucus provides a non invasive method of diagnosing various diseases related to human physiology and pathology. The methods of the present invention include treatment of diseases by modulating the concentrations of NO by use of drugs or agents. The method of treatment is preferably by nasal administration.

Tables 36-38 illustrate detection and measurement of TNFα, TNFR 1 and TNFR 2 in nasal mucus of patients with graded loss of smell following treatment with theophylline. Results indicate that detection and measurements of TNFα, TNFR 1 and TNFR 2 in nasal mucus can be used as an index of the disease process and of changes toward normal as the disease is successfully treated, in the present case with theophylline. Further, nasal mucus can be used as an index of disease, disease severity and efficacy of disease treatment. Without limiting the scope of the present invention, this approach is applicable to other substances in nasal mucus in relationship to other disease processes (e.g., cancer, stroke) and to follow-up of their treatment with any drug.

Treatment with Transcranial Magnetic Stimulation

Loss of taste and smell acuity (hypogeusia and hyposmia, respectively) with subsequent gustatory and olfactory distortions in the absence of oral or external olfactory stimuli [(phantageusia and phantosmia, respectively) labeled sensory distortions], are symptoms which may occur in some patients without other neurological or psychological disorders.

Transcranial magnetic stimulation (TCMS) use has been limited by lack of objective methods to measure efficacy of its application. One aspect of the invention includes method of treatment of patients with loss of taste and/or smell (hypogeusia and/or hyposmia, respectively) with subsequent gustatory and/or olfactory distortions (phantageusia and/or phantosmia, respectively) with repetitive TCMS (rTCMS) which improved their sensory acuity and decreased their sensory distortions.

Increased CA VI secretion has been considered a marker for both increased taste and smell function. Thus, before and after rTCMS, CA VI activity and other salivary proteins were measured in patients with both sensory loss and presence of sensory distortions. Since CA VI is a zinc containing glycose talloprotein, the salivary zinc and copper concentrations were also measured to determine if changes in these parameters correlated with changes in CA VI activity. The possibility of the changes in other salivary proteins was also investigated. Changes in erythrocyte CA I, II as well as concentrations of zinc and copper in both erythrocytes and in blood plasma, were also measured.

Example 40 shows the study of ninety-three patients with hyposmia, hypogeusia, phantosmia and/or phantageusia before and after rTCMS. Measurements were made of activities of CA I, II in erythrocytes and of CA VI, of concentrations of zinc and copper in parotid saliva, blood serum, and erythrocytes and of appearance of proteins in saliva by SELDI-TOF mass spectrometry. Results showed that after rTCMS, significant increases occurred in CA I, II, CA VI, and in concentrations of zinc and copper in blood plasma, erythrocytes and saliva. Salivary proteins at m/z value of 21.5K with a repeating pattern at intervals of 5K m/z were induced.

These results demonstrate the biochemical changes in specific enzymatic activities and trace metal concentrations following rTCMS. These changes may relate not only to several aspects of clinical abnormalities of sensory function but also to other neurological disorders including epilepsy, parkinsonism, Alzheimer disease, head injury and motor neuron disease. Example 41 shows efficacy of treatment with rTCMS for patients with these cognitive impairments such as hypogeusia, hyposmia, phantageusia, and phantosmia.

Other Example of Drugs

Drugs that may be used in the methods of treatment of the present invention may be selected from the following, viz. vaccination, alcohol abuse preparations, drugs used for Alzheimer's disease, anesthetics, acromegaly agents, analgesics, antiasthmatics, anticancer agents, anticoagulants and antithrombotic agents, anticonvulsants, antidiabetics antiemetics, antiglaucoma, antihistamines, anti-infective agents, antiparkinsons, antiplatelet agents, antirheumatic agents, antispasmodics and anticholinergic agents, antitussives, carbonic anhydrase inhibitors, cardiovascular agents, cholinesterase inhibitors, treatment of CNS disorders, CNS; stimulants, contraceptives, cystic fibrosis management, dopamine receptor agonists, endometriosis management, erectile dysfunction therapy, fertility agents, gastrointestinal agents, immunomodulators and immunosuppressives, memory enhancers, migraine preparations, muscle relaxants, nucleoside analogues, osteoporosis management, parasympathomimetics, prostaglandins, psychotherapeutic agents, sedatives, hypnotics and tranquilizers, drugs used for slain ailments, steroids and hormones; Examples of alcohol abuse preparations are chlorazepate, chlordiazepoxide, diazepam, I disulfuram, hydroxyzine, naltrexone and their salts.

Examples of analgesics are acetaminophen, aspirin, bupivacain, boprenorphine, butorphanol, celecoxib, clofenadol, choline, clonidine, codeine, diflunisal, dihydrocodeine, dihydroergotamine, dihydromorphine, ethylmorphine, etodolac, eletriptan, eptazocine, ergotamine, fentanyl, fentoprofen, hyaluronic acid, hydrocodon, hydromorphon, hylan, ibuprofen, lindomethacin, ketorolac, lcetotifen, levomethadon, levallorphan, levorphanol, lidocaine, mefenamic acid, meloxicam, meperidine, metl1adone, morphine, nabumetone, nalbuphin, nefopam, nalorphine, naloxone, naltrexone, naproxen, naratriptan, nefazodone, mormethadon, oxaprozin, oxycodone, oxymorphon, pentazocin, pethidine, phenpyramid, piritramid, piroxicam, propoxyphene, refecoxib, rizatriptan, salsalaketoprofen, sulindac, sumatriptan, tebacon, tilidin, tolmetin, tramadol, zolmitriptan and their salts.

Examples of antiasthmatics are ablukast, azelastine, bunaprolast, cinalukast, cromitrile, cromolyn, enofelast, isamoxole, ketotifen, levcromekalin, lodoxamide, montelukast, ontazolast, oxarbazole, oxatomide, piriprost potassium, pirolate, pobilukast edamine, quazolast, repirinast, ritolukast, sulukast, tetrazolastmeglumine, tiaramide, tibenelast, tomelukast, tranilast, verlukast, verofylline, szarirlukast.

Examples of anticancer agents are adriamycin, aldesleukin, allopurinol, altretamine, amifostine, anastrozole, asparaginase, betamethasone, bexarotene, bicalutamide, bleomycin, busulfan, capecitabine, carboplatin, cannustine, chlorambucil, cisplatin, cladarabine, conjugated estrogen, cortisone, cyclophosphamide, cylarabine, dacarbazine, daunorubicin, dactinomycin, denileukin, dexamethasone, discodermolide, docetaxel, doxorubicin, eloposidem, epirubicin, epoetin, epothilones, estramustine, esterified estrogen, ethinyl estradiol, etoposide, exemestane, flavopirdol, fluconazole, fludarabine, fluorouracil, flutamide, floxuridine, gemcitabine, gemtuzumab, goserelin, hexamethylmelamine, hydrocortisone, hydroxyurea, idarubicin, ifosfamide, interferon, irinotecan, lemiposide, letrozole, leuprolide, levamisole, levothyroxine, lomustine, mechlorethamine, melphalan, mercaptopurine mechlorethamine, megesterol, methotrexate, methylprednisolone, methyltestosterone, mithramycin, mitomycin, mitotane, mitoxantrone, mitozolomide, mutamycin, nilutamide, paclitaxel, pamidronate, pegaspargase, pentostatin, plicamycin, porfimer, prednisolone, procarbazine, rituximab, sargramostim, semustine, skeptozocin, tamoxifen, temozolomide, teniposide, testolactone, thioguanine, thiotepa, tomudex, topotecan, toremifene, trastumuzab, tretinoin, semustine, skeptozolocin, valrubicin, verteporfin, vinblastine, vincristine, vindesine, vinorelbine and their salts.

Examples of anticoagulants and antithrombic agents are warfarin, dalteparin, heparin, tinzaparin, enoxaparin, danaparoid, abciximab, alprostadil, altiplase, anagralide, aniskeplase, argatroban, ataprost, beraprost, camonagreel, cilostazol, clinprost, clopidogrel, cloricromen, dermatan, desirudin, domitroban, drotaverine, epoprostenol, eptifibatide, gabexate, iloprost, isbogrel, lamifiban, lamoteplase, lepirudin, levosimendan, lexipafant, melagatran, nafagrel, nafamostsat, nizofenone, orbifiban, ozagrel, pamicogrel, parnaparin, quinobendan, reteplase, sarpogralate, satigrel, silteplase, simendan, ticlopidine, vapiprost, tirofiban, xemilofiban, Y20811 and their salts.

Examples of anticonvulsants are carbamazopine, clonazepam, clorazepine, diazepam, divalproex, ethosuximide, ethotion, felbamate, fosphenyloin, gabapentin, lamotrigine, levetiracetam, lorazepam, mephenyloin, mephobarbital, metharbital, methsuximide, oxcarbazepine, phenobarbital, phenyloin, primidone, tiagabine, topiramate, valproic acid, vigabatrin, zonisamide, and their salts. Examples of antidiabetic agents are acarbose, acetohexamide, carbutamide, chlorpropamide, epalrestat, glibornuride, gliclazide, glimepiride, glipizide, gliquidone, glisoxepid, glyburide, glyhexamide, metformin, miglitol, nateglinide, orlistat, phenbutamide, pioglitazone, repaglinide, rosiglitazone, tolazamide, tolbutamide, tolcyclamide, tolrestat, troglitazone, voglibose and their salts.

Examples of antiemetics are alprazolam benzquinamide, benztropine, betahistine, chlorpromazine, dexamethasone, difenidol, dimenhydrinate, diphenhydramine, dolasetron, domperidone, dronabinol, droperidol, granisetron, haloperidol, lorazepam, meclizine, methylprednisolone, metoclopramide, ondansetron, perphenazine, prochlorperazine, promethazine, scopolamine, tributine, triethylperazine, triflupromazine, trimethobenzamide, tropisetron and their salts.

Examples of antiglaucoma agents are alprenoxime, dapiprazole, dipivefrin, latanoprost, naboctate, pirnabine and their salts.

Examples of antihistamines are acrivastine, activastine, albuterol, azelastine, bitolterol, alimemazine, amlexanox, azelastine, benzydamine, brompheniramine, cetirizine, chlorpheniramine, cimetidine, clemastine, cycloheptazine, cyproheptadine, diclofenac, diphenhydramine, dotarizine, ephedrine, epinastine, epinephrine, ethyluorepinephrine, fenpoterol, fexofenadine, flurbiprofen, hydroxyzine, ibuprofen, isoetharine, isoproterenol, ipratropium bromide, ketorolac, levocetirizine, loratidine, mequitazine, metaproterenol, phenylephrine, phenylpropanol amine, pirbuterol, promethazine, pseudo ephedrine, pyrilamine, salmeterol, terbutaline, tranilast, xanthine derivatives, xylometazoline and their salts.

Examples of anti-infective agents are abacavir, albendazole, amantadine, amphotericin, amikacin, aminosalicylic acid, amoxycillin, ampicillin, amprenavir, atovaquin, azithromycin, aztreonam, carbenicillin, cefaclor, cefadroxil, cefamandole, cefazolin, cefdinir, cefepime, cefixime, cefoperazone, cefotaxime, cefotitam, cefoperazone, cefoxitin, ceLpodoxine, cefprozil, ceftazidime, ceftibuten, ceftizoxime, ceftriaxone, cefuroxime, cephalexin, chloroquine, cidofovir, cilastatin, ciprofloxacin, clarithromycin, clavulinic acid, clindamycin, colistimethate, dalfopristine, dapsone, daunorubicin, delavirdin, demeclocycline, didanosine, doxycycline, doxorubicin, efavirenz, enoxacin, erythromycin, ethambutol, ethionamide, famsiclovir, fluconazole, flucytocin, foscarnet, fosfomycin, ganciclovir, gatifloxacin, griseofulvin, hydroxychloroquine, imipenem, indinavir, interferon, isoniazide, itraconazole, ivermectin, ketoconazole, lamivudine, levofloxacin, linezolide, lomefloxacin, lovacarbef, mebendazole, mefloquine, meropenem, methanamine, metronidazole, minocycline, moxefloxacin, nalidixic acid, nelfnavir, neomycin, nevirapine, nitrofurantoin, norfloxacin, ofloxacin, olseltamivir, oxytetracycline, palivizumab, penicillins, perfloxacin, piperacillin, praziquantel, pyrazinamide, pyrimethamine, quinidine, quinupristine, retonavir, ribavirin, rifabutine, rifampicin, rimantadine, saquinavir, sparfloxacin, stavudine, streptomycin, sulfamethoxazole, teramycin, terbinafine, tetracycline, ticarcillin, thiabendazole, tobramycin, trimethoprim, trimetraxate, troleandomycin, trovafloxacin, valacyclovir, vancomycin, zalcitabine, zanamivir, zidovudine and their salts.

Examples of antiparkinsons are amantadine, adrogolide, altinicline, benztropine, biperiden, brasofensine, bromocriptine, budipine, cabergoline, dihydrexidine, entacapone, etilevodopa, idazoxan, iometopane, lazabemide, melevodopa, carbidopa/levodopa, mofegiline, moxiraprine, pergolide, pramipexole, quinelorane, rasagiline, ropinirole, seligiline, talipexole, tolcapone, trihexyphenidyl and their salts. Examples of antirheumatic agents are azathiprine, betamethasone, celecoxib, cyclosporin, diclofenac, hydroxychloroquine, indomethacin, infliximab, mercaptobutanedioic acid, methylprednisolone, naproxen, penicillamine, piroxicam, prednisolone, sulfasalazine and their salts.

Examples of platelet agents are abciximab, anagrelide, aspirin, cilostazol, clopidogrel, dipyridamole, epoprostenol, eptifbatide, ticlopidine, tinofban and their salts. Examples of antispasmodics and anticholinergic agents are aspirin, atropine, diclofenac, hyoscyamine, mesoprostol, methocarbamol, phenobarbital, scopolamine and their salts.

Examples of antitussives are acetaminophen, acrivastin, albuterol, benzonatate, beractant, brompheniramine, caffeine, calfactant, carbetapentane, chlorpheniramine, codeine, colfuscerin, dextromethorphan, dornase alpha, doxylamine, epinephrine, fexofenadine, guaiphenesin, iprakopium, levalbuterol, metaproterenol, montelukast, pentoxyphyline, phenylephrine, phenylpropanolamine, pirbuterol, poractant alpha, pseudoephedrine, pyrilamine, salbuterol, salmeterol, terbutaline, theophylline, zafirlukast, zileuton and their salts. Examples of carbonic anhydrase inhibitors are acetazolamide, dichlorphenamide, dorzolamide, methazolamide, sezolamide and their salts.

Examples of cardiovascular agents are abciximab, acebutolol, activase, adenosine, adrenaline, amidarone, amiloride, amlodipine, amyl nikate, atenolol, atorvastatin, benazepril, bepiridil, betaxalol, bisoprolol, candesartan, captopril, cartenolol, carvedilol, cerivastatin, chlorthalidone, chlorthiazole, clofibrate, clonidine, colestipol, colosevelam, digoxin, diltiazem, disopyramide, dobutamine, dofetilide, doxazosin, enalapril, epoprostenol, eprosartan, esmolol, ethacrynate, erythrityl, felodipine, fenoidapam, fosinopril, fleicamide, fluorosemide, fluvastatin, gewhibrozil, hydrochlorthiazide, hydroflumethazine, ibutilide, indapamide, isosorbide, irbesartan, labetolol, lacidipine, lisinopril, losartan, lovastatin, mecamylamine, metoprolol, metaraminol, metazolone, methylchlorthiazide, methyldopa, metyrosine, mexiletine, midrodine, milrinone, moexipril, nadolol, niacin, nicardipine, nicorandil, nifedipine, nimodipine, nisoldipine, nikoglycerin, phenoxybenzamine, perindopril, polythiazide, pravastatin, prazosin, procainamide, propafenone, propranolol, quanfacine, quinapril, quinidine, ranipril, reteplase, simvastatin, sotalol, spironolactone, skeptokinase, telmisartan, terazosin, timolol, tocainamide, tors-emide, kandolapril, kiamterene, kapidil, valsartan and their salts.

Examples of cholinesterase inhibitors are donepezil, edrophonium, neostigmine, pyridostigmine, rivasti.gmine, tacrine and their salts. Examples of CNS stimulants are caffeine, doxapram, dexoamphetamine, donepezil, edrophonium, methamphetamine, methylphenidate, modafinil, neostigwine, pemoline, phentermine, pyridostigmine, rivastigwine, tacrin and their salts. Examples of cystic fibrosis management are dornase alpha, pancrelipase, tobramycin and their salts. Examples of dopamine receptor agonists are amantadine, cabergoline, fenoldopam, pergolide, pramipexil, ropinirole and their salts. Examples of drugs used for endometriosis management are danazol, goserelin, leuprolide, nafarelin, norethindrone and their salts. Examples of drugs used for erectile dysfunction therapy are alprostadil, sildenafil, yohimbine and their salts. I Examples of gastrointestinal agents are aldosetron, bisacodyl, bismuth subsalicylate, celecoxib, difoxin, dipheoxylate, docusate, famotidine, glycopyrrolate, infliximab, lansoprazole, loperamide, metaclopramide, nizatidine, omeprazole, pantoprazole, rabeprazole, ranitidine, simethicone, sucralfate, and their salts.

Examples of immunomodulators and immunosupressives are azathioprin, ceftizoxine, cyclosporin, daclizumab, glatiramer, immunoglobulin, interferon, leflunomide, levamisol, mycophenolate, mausomanab, phthalidomide, ribavirin, sirolimus and their salts. Examples of drugs used in Alzheimer's disease are donepezil, galanthamine, metrifonate, rivastigwine, tacrine, TAK-147 and their salts. Examples of drugs used for migraine preparations are acetaminophen, dihydroergotamine, divalproex, ergotamine, propranolol, risatriptan, sumatriptan, trimetrexate and their salts. Examples of muscle relaxants are alcuronium-chloride, azapropazon, atracurium, baclofen, carisoprodol, quinine derivatives, chloromezanon, chlorophenesincarbamate, chlorozoxazon, cyclobenzaprine, dantrolene, decamethoniumbromide, dimethyltubocurariniumchloride, doxacurium, fenyrami dol, gall amintriethio dide, guaiphenesin, hexafluoreniumbromide, hexacarbacholinbromide, memantin, mephenesin, meprobamate, metamisol, metaxalone, methocarbamol, mivacurium, orphenadrin, pancuronium, phenazon, phenprobamate, pipecuronium, rapacuronium, rocuronium, succinylcholine, soxamethoniumchloride, tetrazepam, tizanidine, tubocurarine chloride, tybamate, vecuronium and their salts.

Examples of nucleoside analogues are abacavir, acyclovir, didanosine, ganciclovir, gewcitabine, lamivudine, ribavirin, stavudine, zalcitabine and their salts. Examples of drugs used for osteoporosis management are alendronate, calcitonin, estradiol, estropipate, medroxyprogesterone, norethindrone, norgestimate, pamidronate, raloxifen, risdronate, zolendronate and their salts. Examples of parasympathomimetics are bethanechol, piperidine, edrophonium, glycopyrolate, hyoscyamine, pilocarpine, tacrine, yohimbine and their salts. Examples of prostaglandins are alprostadil, epoprostenol, misoprostol and their salts. Examples of psychotherapeutic agents are acetophenazine, alentemol, alpertine, alprazolam, amitriptyline, aripiprazole, azaperone, batelapine, befipiride, benperidol, benzindopyrine, bimithil, biriperone, brofoxine; bromperidol; bupropion, buspirone, butaclamol, butaperazine; carphenazine, carvotroline, cericlamine, chlorazepine, chlordiazepoxide, chlorpromazine; chlorprothixene, cinperene, cintriamide, citalopram, clomacran, clonazopam, clopenthixol, clopimozide, clopipazan, cloroperone, clothiapine, clothixamide, clozapine; cyclophenazine, dapiprazole, dapoxetine, desipramine, divalproex, dipyridamole, doxepin, droperidol, duloxetine, eltoprazine, eptipirone, etazolate, fenimide, fibanserin, flucindole, flumezapine, fluoxetine, fluphenazine, fluspiperone, fluspirilene, flutroline, fluvoxamine, gepione, gevotroline, halopemide, haloperidol, hydroxyzine, hydroxynortriptyline, iloperidone, imidoline, lamotrigine, loxapine, enperone, mazapertine, mephobarbital, meprobamate, mesoridazine, mesoridazine, milnacipran, mirtazapine, metiapine, milenperone, milipertine, molindone, nafadotride, naranol, nefazodone, neflumozide, ocaperidone, odapipam, olanzapine, oxethiazine, oxiperomide, pagoclone, paliperidone, paroxitene, penfluridol, pentiapine perphenazine, phenelzine, pimozide, pinoxepin, pipamperone, piperacetazine, pipotiazine, piquindone, pilindole, pivagabine, pramipexole, prochlorperazine, prochlorperazine, promazine, quetiapine, reboxetine, remoxipride, remoxipride, risperidone, rimcazole, robolzotan, selegiline, seperidol, sertraline, sertindole; septiline, setoperone, spiperone, sunipitron, tepiindole, thioridazine, thiothixene, tiapride, tioperidone, tiospione, topiramate, tranylcypromine, trifluoperazine, trifluperidol, triflupromazine, triflupromazine, kimipramine, venlafaxine, ziprasidone and their salts.

Examples of sedatives, hypnotics and tranquilisers are bromazepam, buspione, clazolam, clobazam, chlorazepate, diazepam, demoxepam, dexmedetomitine, diphenyhydramine, doxylamine, enciprazine, estrazolam, hydroxyzine, ketazolam, lorazatone, lorazepam, loxapine, medazepam, meperidine, methobarbital, midazolam, nabilone, nisobamate, oxazepam, pentobarbital, promethazine, propofol, triazolam, zalelplon, zolpidem and their salts. Examples of drugs used for treatment of skin ailments are acitretin, alclometasone, allitretinoin, betamethasone, calciprotrine, chlorhexidine, clobetasol, clocortolone, clotriamozole, collagenase, cyclosporin, desonide, difluorosone, doxepine, eflornithine, finasteride, fluocinolone, flurandrenolide, fluticasone, halobetasol, hydrochloroquine, hydroquinone, hydroxyzine, ketoconazole, mafenide, malathion, menobenzone, neostigmine, nystatin, podoflox, povidone, tazorotene, tretinoin and their salts.

Examples of steroids and hormones are alclometasone, betamethasone, calcitonin, cikorelix, clobetasol, clocortolone, cortisones, danazol, desmopressin, desonide, desogestrel, desoximetasone, dexamethasone, diflorasone, estradiol, estrogens, estropipate, ethynlestradiol, i fluocinolone, flurandrenolide, fluticasone, glucagon, gonadotropin, goserelin, halobetasol, hydrocortisone, leuprolide, levonorgestrel, levothyroxine, medroxyprogesterone, menotropins, methylprednisolone, methyltestosterone, mometasone, naferelin, norditropin, norethindrone, norgestrel, octreolide, oxandrolone, oxymetholone, polytropin, prednicarbate, prednisolone, progesterone, sermorelin, somatropin, stanozolol, testosterone, urofollitropin and their salts.

Example of agents that are susceptible to the gastric environment such as proton pump inhibitors are pantoprazole, omeprazole, lansoprazole, esomeprazole, rabeprazole, paripraprazole, leminoprazole, or an enantiomer, isomer, derivative, free base or salt thereof; lipid-lowering agents such as lovastatin, pravastatin, atorvastatin, simvastatin; agents that are targeted to the intestine for local action such as 5-aminosalicylic acid, corticosteroids such as beclomethasone, budesonide, fluticasone, tixocortol useful in treating Crohn's disease and ulcerative colitis; agents that may be inactivated by the gastric contents such as enzymes like pancreatin, antibiotics such as erythromycin; agents that cause bleeding or irritation of the gastric mucosa such as aspirin, steroids, non-steroidal anti-inflammatory compounds like ibuprofen, naproxen, ketoprofen, fenoprofen, flurbiprofen, oxaprozin, diflunisal, diclofenac, indomethacin, tolmetin, sulindac, etodolac, acetaminophen, platelet inhibitors such as abciximab, intergrelin, dipyridamole; nucleoside analogs such as didanosine, transfer factor preparations, hormones, insulin, and other agents that have decreased stability in the gastric environment, as well as agents that are required for local action in the latter part of the gastrointestinal tract. The agents may be used as their base or as their pharmaceutically acceptable salt or solvate thereof.

The treatment can be via oral administration, transmucosal administration, buccal administration, nasal administration, inhalation, parental administration, intravenous, subcutaneous, intramuscular, sublingual, transdermal administration, and rectal administration. Nasal administration is a preferred mode in the present invention. Nasal administration may delay or obviate drug resistance that may occur through the other routes of administration, such as, oral or parentral.

Effective Dosages

Pharmaceutical compositions suitable for use in the present invention include compositions wherein the active ingredient is contained in a therapeutically or prophylactically effective amount, i.e., in an amount effective to achieve therapeutic or prophylactic benefit. Of course, the actual amount effective for a particular application will depend, inter alia, on the condition being treated and the route of administration. Determination of an effective amount is well within the capabilities of those skilled in the art, especially in light of the disclosure herein.

Therapeutically effective amounts for use in humans can be determined from animal models. For example, a dose for humans can be formulated to achieve circulating concentration that has been found to be effective in animals. The amount administered can be the same amount administered to treat a particular disease or can be an amount lower than the amount administered to treat that particular disease. Patient doses for oral administration of the drug may range from about 1 µg-1 gm/day. The dosage may be administered once per day or several or multiple times per day. The amount of the drug administered to practice methods of the present invention will of course, be dependent on the subject being treated, the severity of the affliction, the manner of administration and the judgment of the prescribing physician. The dose used to practice the invention can produce the desired therapeutic or prophylactic effects, without producing serious side effects.

Routes of Administration

The methods of treatment in the invention include by way of example only, oral administration, transmucosal administration, buccal administration, nasal administration such as inhalation, parental administration, intravenous, subcutaneous, intramuscular, sublingual, transdermal administration, and rectal administration.

In some embodiments of the present invention, the method of treatment is by nasal administration or inhalation. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. The compositions can be administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

In some embodiments of the present invention, the method of treatment is by oral administration. Oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the method of treatment of the present invention to provide tablets that disintegrate when exposed to an aqueous environment. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed. A solubilizer may also be added to increase the solubility of the hydrophilic drug and/or other components, such as surfactants, or to maintain the composition as a stable or homogeneous solution or dispersion.

Mixtures of solubilizers may be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The compositions for the treatment can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

The compositions for delivery can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

In some embodiments of the present invention, the method of treatment can be transdermal. Transdermal patches may be used to provide continuous or discontinuous infusion in controlled amounts, either with or without therapeutic agent. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical compositions may also be prepared with one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

Kits

Figure 3:
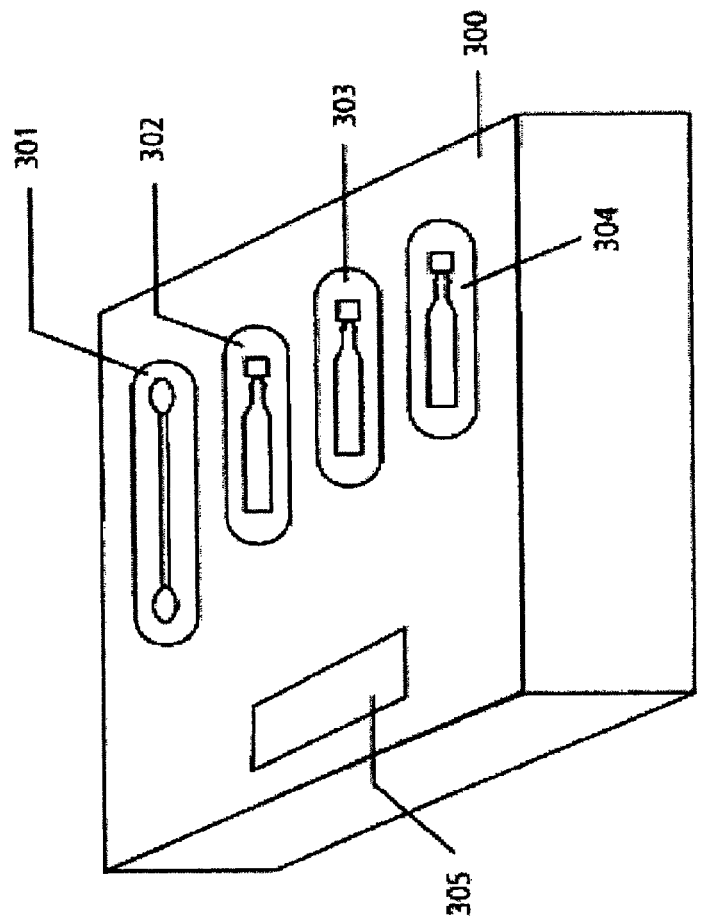
FIG. 3 depicts a kit for a detection of biological substance in a nasal specimen.

The invention also provides kits. As shown in FIG. 3, by way of example only, the kit 300 may include a sterile nasal swab 301 for collection of nasal secretions, an elongated storage and transport tube 302 for receiving the swab wherein the tube can be glass or plastic and the tube may have a replaceable end closure, and contain a sterile nutrient medium for isolation of the nasal secretions, a sterile assay solution 303 for addition to the transport tube, and a detector medium 304 for the detection of a biological substance in the nasal secretion. The kit may also include written instructions 305. In some embodiments, the therapeutic agent can also be provided as separate compositions in separate containers within the kit for the treatment. Suitable packaging and additional articles for use (e.g., measuring cup for liquid preparations, foil wrapping to minimize exposure to air, and the like) are known in the art and may be included in the kit.

The following preparations and examples serve to illustrate the invention. They should not be construed as narrowing it, or limiting its scope.

EXAMPLES

Example 1

PCR Analysis of a Specimen of Nasal Mucus

Figure 4:
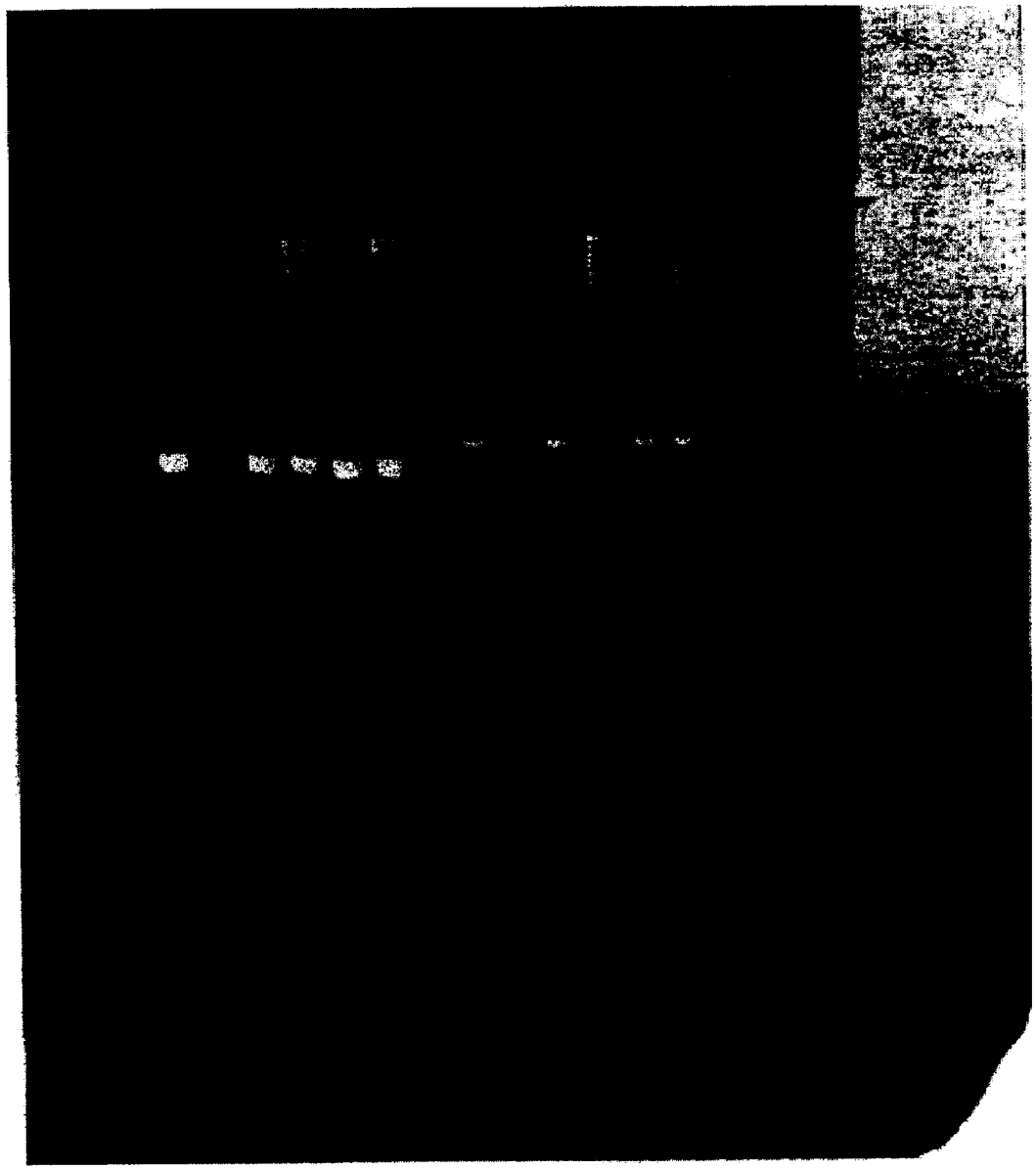
FIG. 4 depicts a polyacrylamide gel electrophoresis of samples as shown in Table 1.

Specimen of nasal mucus from different subjects was collected and analyzed using PCR. FIG. 4 depicts a polyacrylamide gel electrophoresis of samples as shown in Table 1. Lanes 1-7 in FIG. 4 reveal one major band consistent with the presence of HLA. Lanes 8-14 reveal one major band consistent with the presence of β globin. On the right are located molecular weight markers of various KD.

TABLE 1

Results of PCR analysis of two samples of nasal mucus obtained from normal subjects

| Rot. Pos. | Sample Name | Rep. of... | Sample Type* | Known Conc. | Tm1 (° C.) | Area 1 (Units) | Tm2 (° C.) | Area 2 (Units) | Tm3 (° C.) | Area 3 (Units) | Sample Comments |
|---|---|---|---|---|---|---|---|---|---|---|---|
| 1 | WB Pos Cont | | U | | 84.05 | 11.18 | | | | Pos | HLA |
| 2 | R. Blk | | U | | 82.08 | 10.96 | | | | Neg | HLA |
| 3 | Specimen # 1 | | U | | 83.91 | 9.602 | | | | Pos | HLA |
| 4 | Specimen # 2 | | U | | 84.74 | 10.86 | | | | Pos | HLA |
| 5 | Specimen # 1 ± Pos Cont | | U | | 83.40 | 7.006 | | | | Pos | HLA |
| 6 | Specimen # 1 ± Pos Cont | | U | | 84.63 | 8.658 | | | | Pos | HLA |
| 7 | R. Blk | | U | | 80.68 | 5.131 | | | | Neg | HLA |
| 8 | WB Pos Cont | | U | | 87.41 | 6.062 | | | | Pos | beta globin |
| 9 | R. Blk | | U | | 75.92 | 6.166 | | | | Pos | beta globin |
| 10 | Specimen # 1 | | U | | 86.97 | 7.534 | | | | Pos | beta globin |
| 11 | Specimen # 2 | | U | | 76.91 | 5.492 | 86.91 | 8.009 | | Pos | beta globin |
| 12 | Specimen # 1 + Pos Cont | | U | | 86.81 | 7.983 | | | | Pos | beta globin |
| 13 | Specimen # 1 + Pos Cont | | U | | 86.54 | 7.451 | | | | Pos | beta globin |
| 14 | R. Blk | | U | | | | | | | Neg | beta globin |

*P = Positive, U = Unknown, N = Negative, S = Standard, < > = De-Selected

Example 2

DNA Extraction Procedure from Body Fluids with QIAGEN Kit

All specimens and all reagents were equilibrated to room temperature. 20 µl Qiagen Protease (or proteinase K) was pipetted into the bottom of a 1.5 ml centrifuge tube. 200 µl of specimen (nasal mucus, plasma, saliva, urine and other biological fluids) was added to the centrifuge tube. In case of specimens containing less than 1 µg of DNA or RNA, 5-10 µg of carrier DNA or RNA (20 µl of poly dA or 8 µl of poly [C]) was added. 200 µl of AL buffer was added to the tube. Mixture was mixed by pulse-vortexing for 15 sec. Mixture was incubated at 56-60° C. for 15 min. Mixture was vortexed and centrifuged briefly. 200 µl of ethanol (96-100%) was added to the tube. Mixture was vortexed and centrifuged briefly. The mixture was carefully applied to a QIAamp spin column (in a 2 ml collection tube) without wetting the rim. Caps of the columns were closed and the mixture was centrifuged for 1 min. The spin column was placed in another clean collection tube and the tube containing the filtrate was discarded. 500 µl of buffer AW1 was added to the spin column, the lid was closed and the column was spun for 1 min. The column was placed in another clean collection tube and the tube containing the filtrate was discarded. 500 µl of buffer AW2 was added to the spin column, the lid was closed and the column was spun at for 3 minutes; the collection tube containing the filtrate was discarded. Since trace amounts of buffer AW2 inhibit PCR, complete removal of the buffer is desirable. The column is then placed in a clean 1.5 ml centrifuge tube and 50 µl of $H_2O$ was added to it. It was incubated at room temperature for 15 minutes and centrifuged for 3 minutes. The resulting DNA solution can be stored at 4° C. for several months.

Example 3

LightCycler Data Analysis Report

Figure 5:
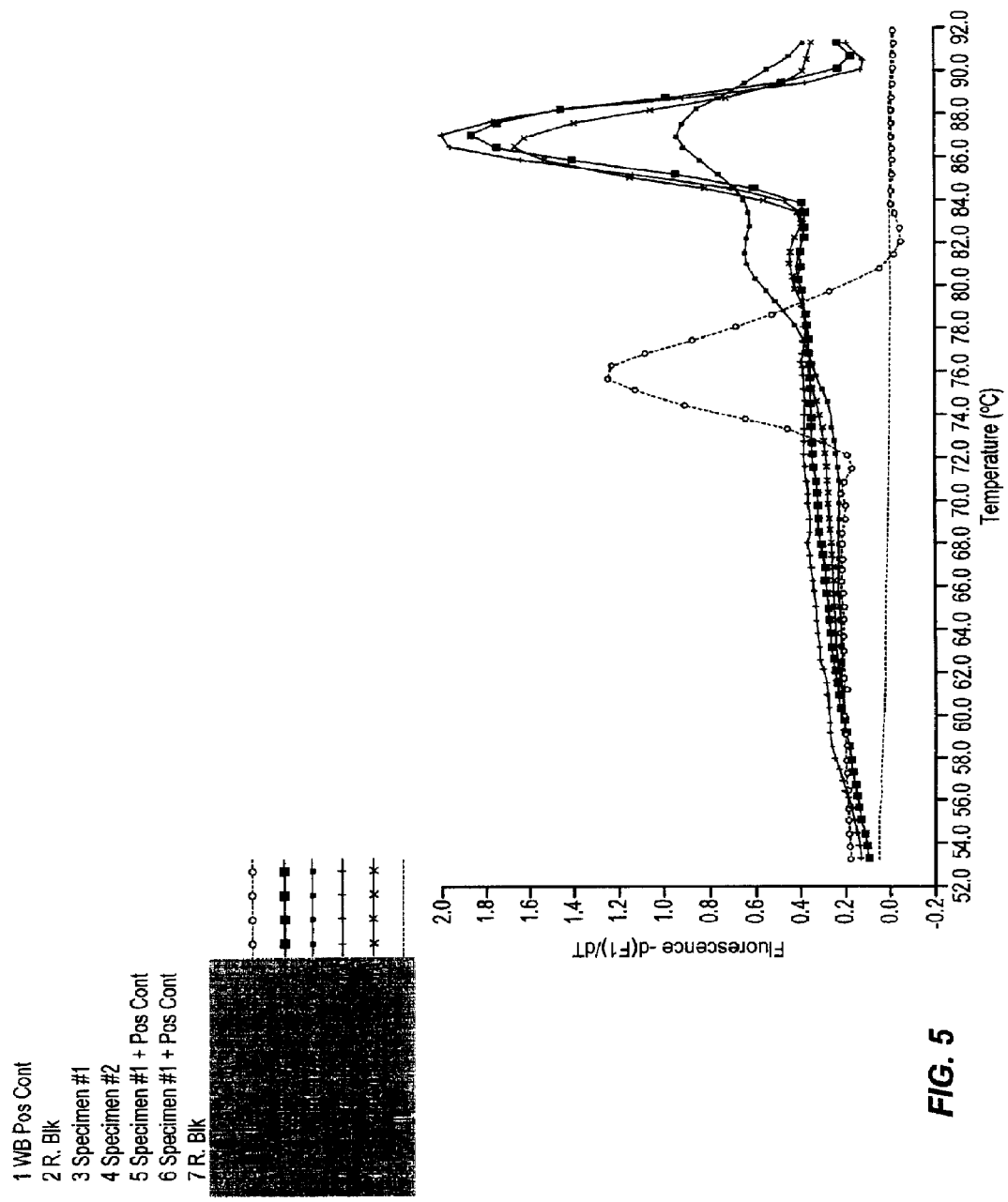
FIG. 5 depict LightCycler melting peak report on results of PCR analysis of two samples of nasal mucus. Fluorescence is plotted on ordinate, temperature on abscissa.
Figure 6:
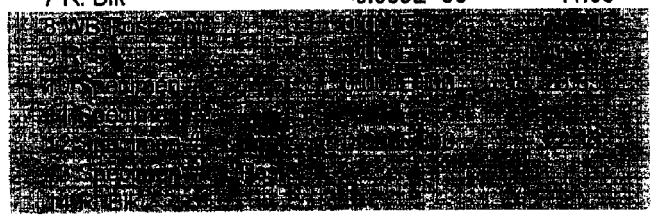
FIG. 6 depicts LightCycler data analysis report on results of PCR analysis of two samples of nasal mucus. Fluorescence is plotted on ordinate, cycle number on abscissa.
Figure 6:
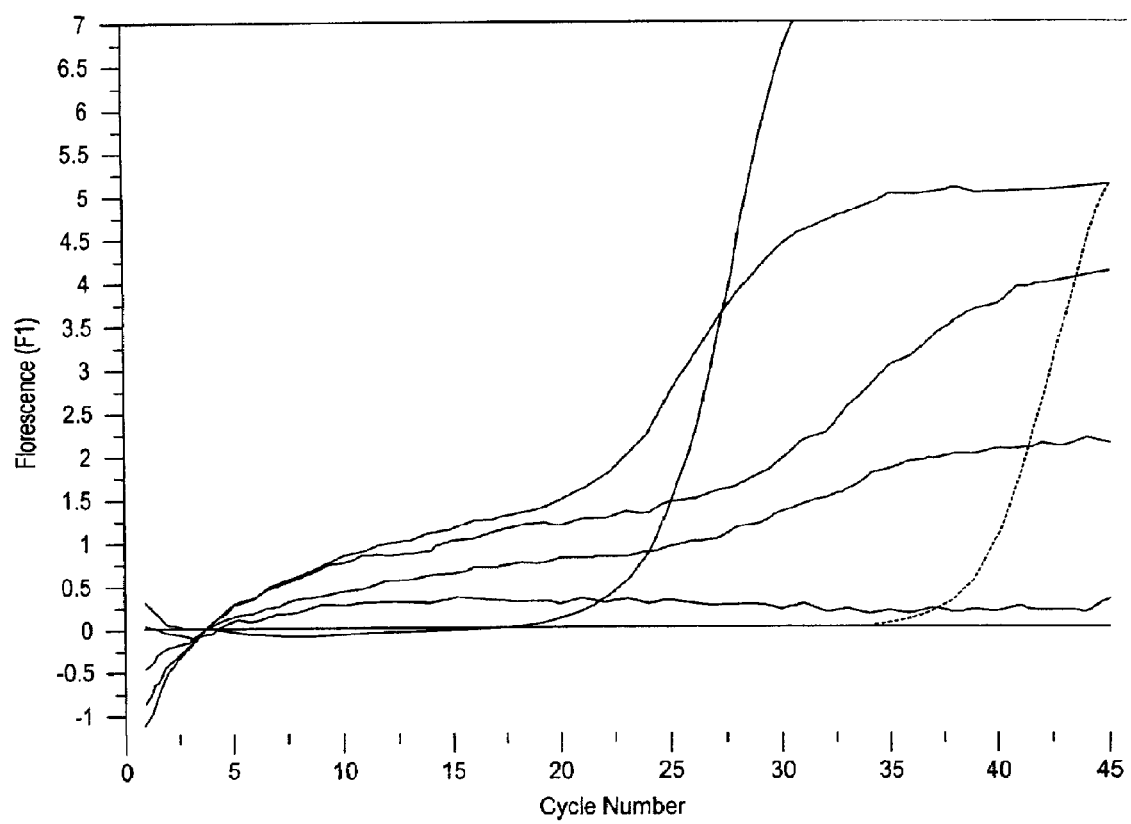
Figure 7:
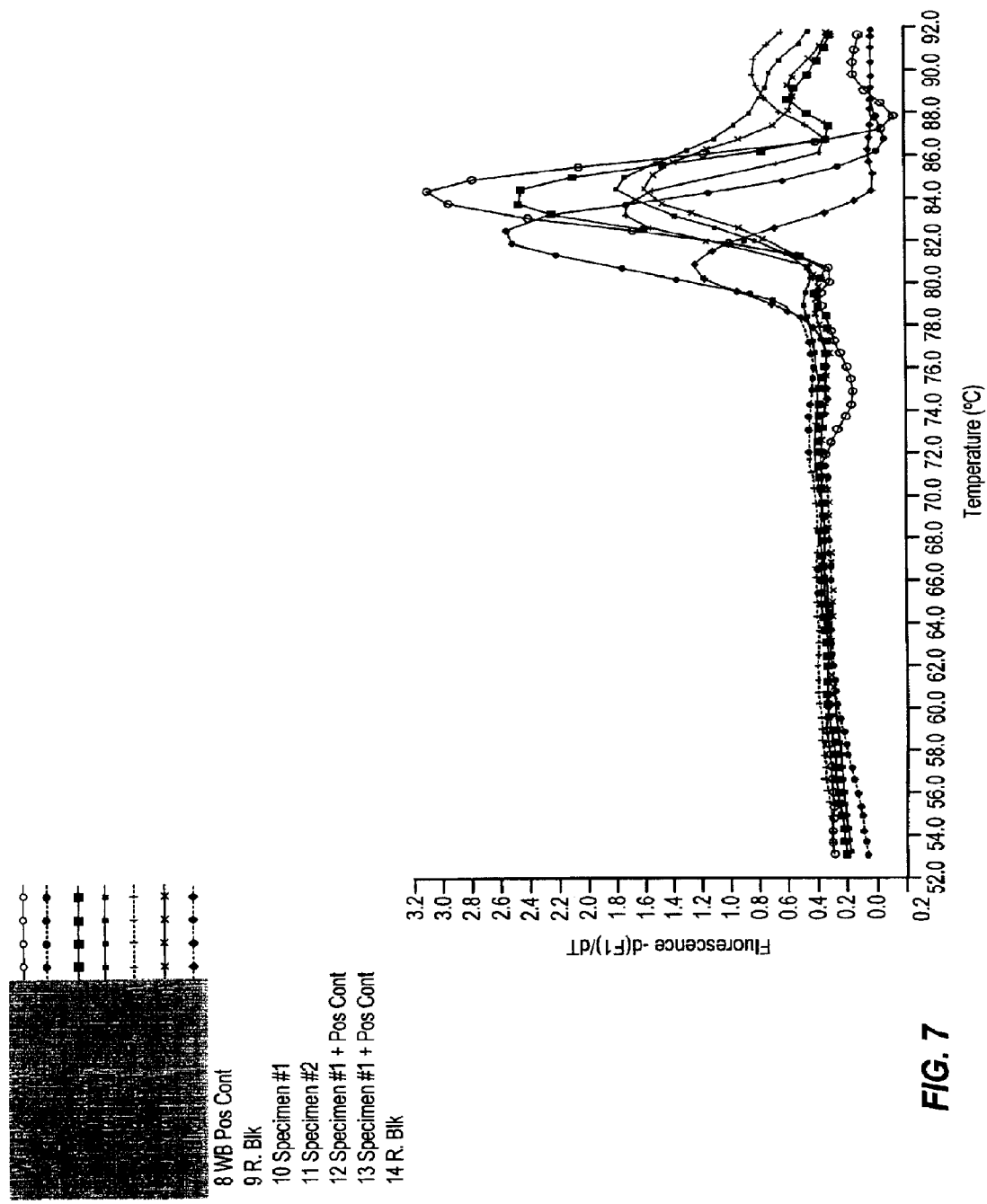
FIG. 7 depicts LightCycler melting peak report on results of PCR analysis of two samples of nasal mucus. Fluorescence is plotted on ordinate, temperature on abscissa.
Figure 8:
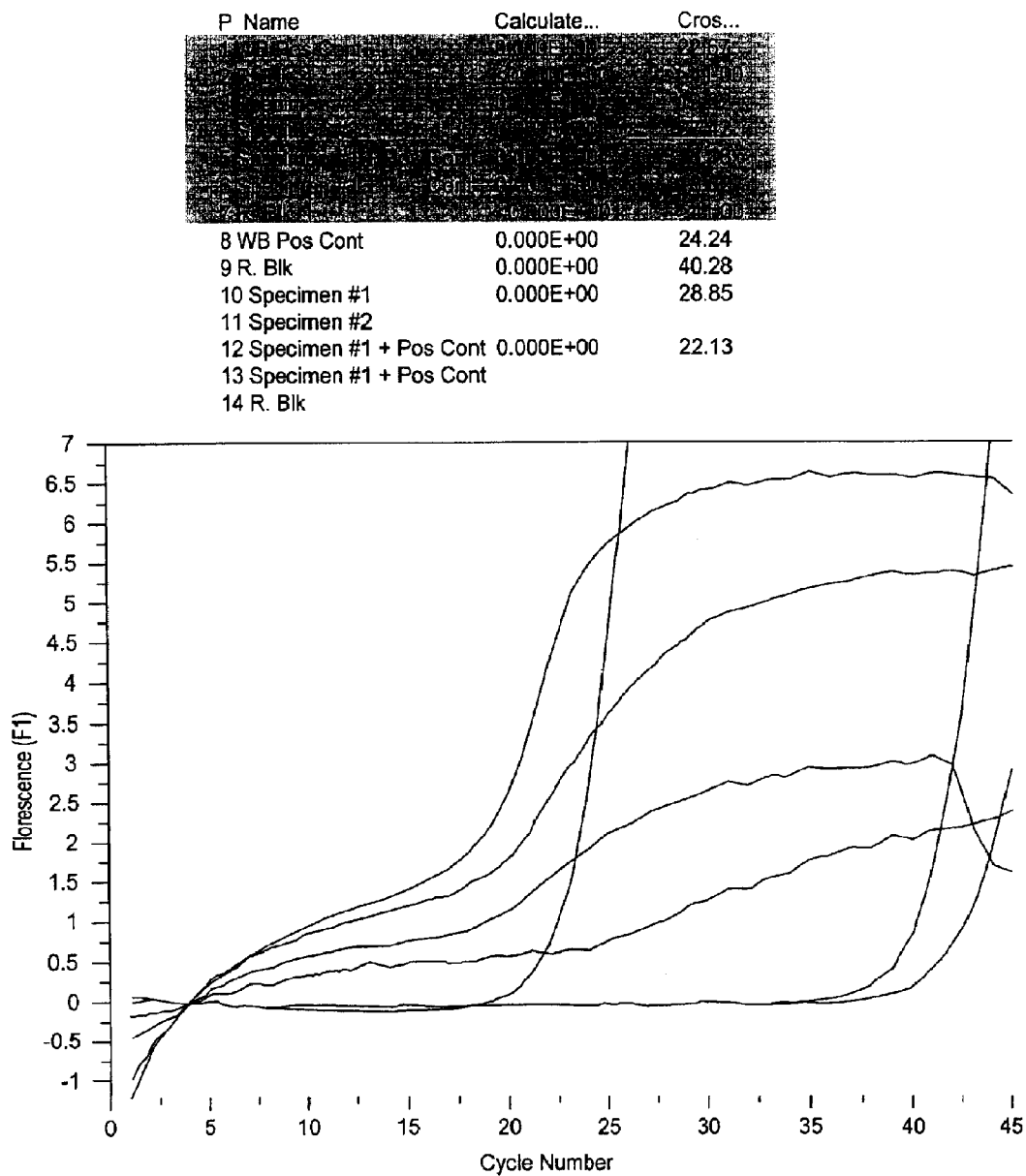
FIG. 8 depicts LightCycler data analysis report on results of PCR analysis of two samples of nasal mucus. Fluorescence is platted on ordinate, cycle number on abscissa.
Figure 9:
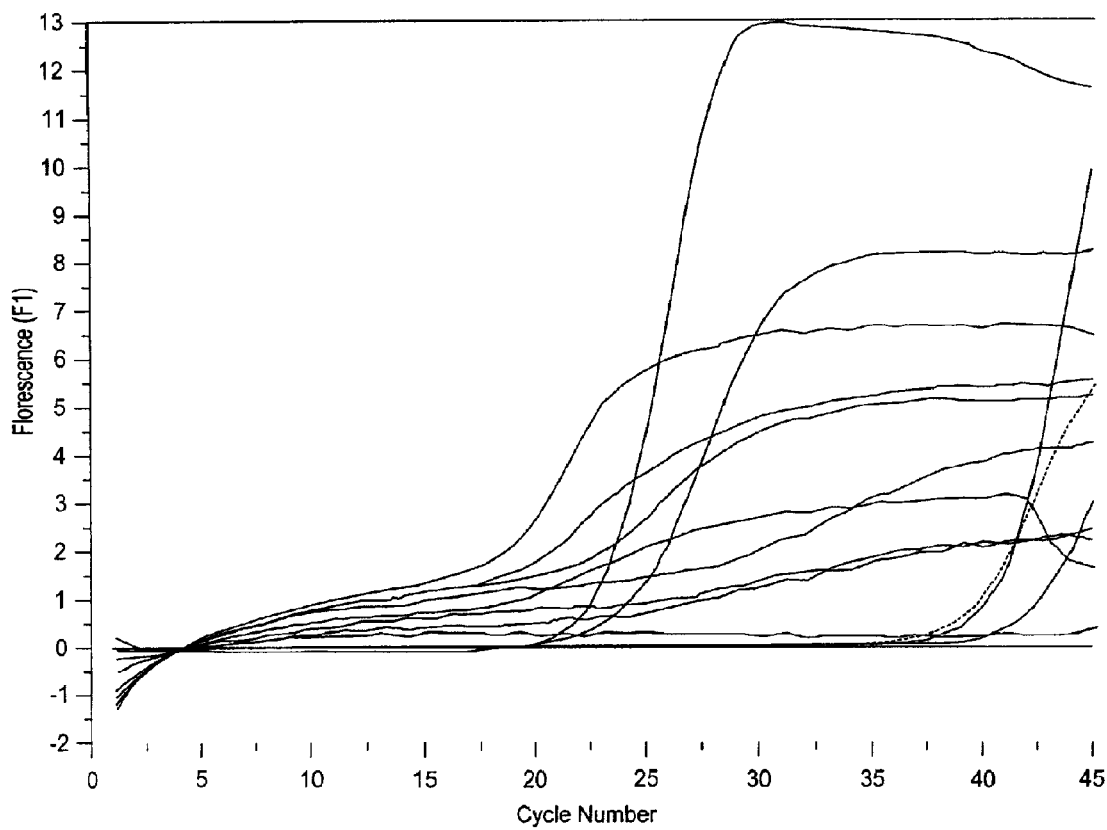
FIG. 9 depicts LightCycler data analysis report on results of PCR analysis of two samples of nasal mucus. Fluorescence is plotted on ordinate, cycle number on abscissa.

FIG. 5 depicts LightCycler melting peak report on results of PCR analysis of two samples of nasal mucus. Fluorescence is plotted on ordinate, temperature on abscissa. FIG. 6 depicts LightCycler data analysis report on results of PCR analysis of two samples of nasal mucus. Fluorescence is plotted on ordinate, cycle number on abscissa. FIG. 7 depicts LightCycler melting peak report on results of PCR analysis of two samples of nasal mucus. Fluorescence is plotted on ordinate, temperature on abscissa. FIG. 8 depicts LightCycler data analysis report on results of PCR analysis of two samples of nasal mucus. Fluorescence is platted on ordinate, cycle number on abscissa. FIG. 9 depicts LightCycler data analysis report on results of PCR analysis of two samples of nasal mucus. Fluorescence is plotted on ordinate, cycle number on abscissa.

TABLE 2

LightCycler Melting Analysis Report of Studies on each of two samples of nasal mucus analyzed by PCR Program: Denature
Type: None
Cycles 1

| Segment Number | Temperature Target (° C.) | Hold Time (sec) | Slope (C. °/sec) | 2° Target Temp (° C.) | Step Size (° C.) | Step Delay (Cycles) | Acquisition Mode |
|---|---|---|---|---|---|---|---|
| 1 | 95 | 600 | 20 | 0 | 0 | 0 | None |

Program: PCR
Type Quantification
Cycles 45

| Segment Number | Temperature Target (° C.) | Hold Time (sec) | Slope (C. °/sec) | 2° Target Temp (° C.) | Step Size (° C.) | Step Delay (Cycles) | Acquisition Mode |
|---|---|---|---|---|---|---|---|
| 1 | 95 | 10 | 20 | 0 | 0 | 0 | None |
| 2 | 58 | 15 | 20 | 0 | 0 | 0 | None |
| 3 | 72 | 12 | 20 | 0 | 0 | 0 | Single |

Program: melt
Type: None
Cycles 1

| Segment Number | Temperature Target (° C.) | Hold Time (sec) | Slope (C. °/sec) | 2° Target Temp (° C.) | Step Size (° C.) | Step Delay (Cycles) | Acquisition Mode |
|---|---|---|---|---|---|---|---|
| 1 | 95 | 0 | 20 | 0 | 0 | 0 | None |
| 2 | 50 | 60 | 20 | 0 | 0 | 0 | None |
| 3 | 95 | 0 | 0.2 | 0 | 0 | 0 | Continuous |

Program: cool
Type: None
Cycles 1

| Segment Number | Temperature Target (° C.) | Hold Time (sec) | Slope (C. °/sec) | 2° Target Temp (° C.) | Step Size (° C.) | Step Delay (Cycles) | Acquisition Mode |
|---|---|---|---|---|---|---|---|
| 1 | 40 | 30 | 20 | 0 | 0 | 0 | None |

| Flouresence Settings | | | | Melting Analysis Settings | |
|---|---|---|---|---|---|
| LED Power | CALIB | Display Mode | 3.5 Compatible | Channel Setting | F1/1 |
| Color | N/A | | | Program Name | melt |
| Compensation | N/A | | | Start Time | 0:52:39.85 Stop Time 0:56:28.2 |
| Car. Movement | Continuous | | | | |

Example 4

Analysis of Nasal Mucus Before and after Fasting

Table 3 depicts the results of the ELISA analysis of nasal mucus collected from 49 subjects before (fasting) and after (non-fasting). FL/VOL is flow rate in ml/min, PROT is protein, LEP is leptin, LEP/PR is leptin/protein, AG is agouti related protein, AG/PR is agouti related protein/protein, INS is insulin, INS/PR is insulin/protein, X is mean values of 49 subjects, and SD is standard deviation of results.

TABLE 3

| | Nasal mucus (nM) | | | | | | | |
|---|---|---|---|---|---|---|---|---|
| SUBJECT | BEFORE FL/VOL ml/min | AFTER FL/VOL ml/min | BEFORE PROT mg/ml | AFTER PROT mg/ml | BEFORE LEP pg/ml | AFTER LEP pg/ml | BEFORE LEP/PR ratio | AFTER LEP/PR ratio |
| 1 | 6.52 | | 2.198 | | 496 | | 226 | |
| 2 | 0.81 | | 2.771 | | | 90 | | |
| 3 | 0.31 | | 2.016 | | | 39 | | |
| 4 | 3.27 | | 2.494 | | | | | |
| 5 | 4.64 | | 2.811 | | 724 | | 258 | |
| 6 | 0.28 | 4.03 | 3.237 | 2.419 | 197 | | 61 | |
| 7 | 49.31 | 29.68 | 2.886 | 2.805 | 510 | 382 | 177 | 136 |
| 8 | 5.18 | | 3.272 | | | | | |
| 9 | 22.37 | 4.76 | 1.751 | 1.999 | | | | |
| 10 | | 3 | | 1.653 | | | | |
| 11 | 0.39 | | 3.865 | | 56 | | 14 | |
| 12 | 3.83 | | 1.192 | | | | | |
| 13 | | 18.38 | | 3.047 | | 230 | | 75 |
| 14 | 0.27 | | | | 2365 | | | |
| 15 | 1.37 | | 2.834 | | | | | |
| 16 | | 8.36 | | 2.252 | | 34 | | 15 |
| 17 | | 9.9 | | 2.644 | | 28 | | 11 |
| 18 | 29.13 | 21.63 | 3.859 | 3.093 | 45 | 51 | 12 | 16 |
| 19 | 2.93 | | 1.584 | | 18 | | 11 | |
| 20 | 1.32 | | 2.114 | | | | | |
| 21 | 5.84 | | 2.068 | | | | | |
| 22 | 5.94 | 1.63 | 2.16 | 2.673 | 107 | | 50 | |
| 23 | 3 | | 3.22 | | | | | |
| 24 | 2.72 | | 2.246 | | 39 | | 17 | |
| 25 | 3.87 | 4.87 | 2.28 | 2.339 | 39 | | 17 | |
| 26 | 1.99 | | 2.707 | | 174 | | 64 | |
| 27 | 27.24 | | 2.845 | | 85 | | 30 | |
| 28 | 3 | | 2.362 | | 79 | | 33 | |
| 29 | 2.21 | | 1.14 | | | | | |
| 30 | | 1.11 | | 3.226 | | | | |
| 31 | 5.59 | | 2.39 | | | | | |
| 32 | 6.77 | | | 2.811 | | 129 | | 46 |
| 33 | 0.55 | | 3.122 | | 388 | | 124 | |
| 34 | | 1.02 | | 2.062 | | 56 | | 27 |
| 35 | 23.8 | | 1.665 | | 56 | | 34 | |
| 36 | 1.13 | | 2.92 | | 225 | | 77 | |
| 37 | | 1.27 | | 1.323 | | 39 | | 29 |
| 38 | | 3.33 | | 3.537 | | 45 | | 13 |
| 39 | | 6.39 | | 1.901 | | 287 | | 151 |
| 40 | | 1.27 | | 1.356 | | 135 | | 100 |
| 41 | 1.22 | | 2.379 | | 183 | | 77 | |
| 42 | 3.35 | 2.72 | 2.609 | 2.892 | 73 | 107 | 28 | 37 |
| 43 | 10.23 | | 1.123 | | 124 | | 110 | |
| 44 | 13.07 | 10.58 | 3.531 | 1.74 | 540 | 1265 | 153 | 727 |
| 45 | 4.15 | | 2.552 | | 22 | | 9 | |
| 46 | 2.76 | 3.83 | 3.012 | 3.859 | 107 | 124 | 36 | 32 |
| 47 | 3.34 | | 3.37 | | 143 | | 42 | |
| 48 | 10.42 | 3.23 | 3.335 | 2.419 | 104 | 56 | 31 | 23 |
| 49 | | 1.09 | | 2.016 | | | | |
| X | 7.21 | 6.77 | 2.55 | 2.46 | 276.0 | 182.2 | 70.5 | 95.9 |
| SD | 10.23 | 7.65 | 0.71 | 0.68 | 475.0 | 296.1 | 69.7 | 180.3 |

| SUBJECT | BEFORE AG pg/ml | AFTER AG pg/ml | BEFORE AG/PR | AFTER AG/PR | BEFORE INS μIU/ml | AFTER INS μIU/ml | BEFORE INS/PR | AFTER INS/PR |
|---|---|---|---|---|---|---|---|---|
| 1 | 1 | | 0 | | 22 | | 10 | |
| 2 | | | | | | | | |
| 3 | | | | | | | | |
| 4 | 7 | | 3 | | 10 | | 4 | |
| 5 | 7 | | 2 | | 7 | | 2 | |
| 6 | 1 | 8 | 0 | 3 | 5 | 16 | 2 | 7 |
| 7 | | | | | 13 | 7 | 5 | 2 |
| 8 | 7 | | 2 | | 31 | | 9 | |
| 9 | | 2 | | 1 | 15 | 5 | 9 | 3 |
| 10 | | 7 | | 4 | | 23 | | 14 |

TABLE 3-continued

| | | | Nasal mucus (nM) | | | | |
|---|---|---|---|---|---|---|---|
| 11 | 6 | | 2 | | 8 | | 2 |
| 12 | 1 | | 1 | | 6 | | 5 |
| 13 | | 4 | | 1 | 10 | | 3 |
| 14 | | | | | | | |
| 15 | 5 | | 2 | | 1 | | 0 |
| 16 | | | | | | | |
| 17 | | | | | | | |
| 18 | 9 | 11 | 2 | 4 | 4 | 12 | 1 | 4 |
| 19 | 2 | | 1 | | 19 | | 12 | |
| 20 | 8 | | 4 | | 11 | | 5 | |
| 21 | 3.5 | | 2 | | 15 | | 7 | |
| 22 | 3 | 2 | 1 | 1 | 11 | 16 | 5 | 6 |
| 23 | 7 | | 2 | | 9 | | 3 | |
| 24 | 7 | | 3 | | 8 | | 4 | |
| 25 | 21 | 8 | 9 | 3 | 43 | 48 | 19 | 21 |
| 26 | 5 | | 2 | | 9 | | 3 | |
| 27 | 7 | | 2 | | 9 | | 3 | |
| 28 | 7 | | 3 | | 43 | | 18 | |
| 29 | 9 | | 8 | | 8 | | 7 | |
| 30 | | 8 | | 2 | | 31 | | 10 |
| 31 | 7 | | 3 | | 74 | | 31 | |
| 32 | | | | | | | | |
| 33 | 1 | | 0 | | 95 | | 30 | |
| 34 | | | | | | | | |
| 35 | 3 | | 2 | | 13 | | 8 | |
| 36 | 8 | | 3 | | 19 | | 7 | |
| 37 | | | | | | | | |
| 38 | | | | | | | | |
| 39 | | 6 | | 3 | | | | |
| 40 | | 6 | | 4 | | 27 | | 20 |
| 41 | 0 | | 0 | | 25 | | 11 | |
| 42 | 2 | 9 | 1 | 3 | 4 | 12 | 2 | 4 |
| 43 | 3 | | 3 | | 2 | | 2 | |
| 44 | | 2 | | 1 | 51 | 24 | 14 | 14 |
| 45 | | | | | 16 | | 6 | |
| 46 | 6 | 10 | 2 | 3 | 14 | 15 | 5 | 4 |
| 47 | 7 | | 2 | | 10 | | 3 | |
| 48 | 4 | 3 | 1 | 1 | 4 | 6 | 1 | 2 |
| 49 | | 6 | | 3 | | | | |
| X | 5.5 | 6.1 | 2.3 | 2.6 | 18.6 | 18.0 | 7.5 | 8.1 |
| SD | 4.0 | 3.0 | 1.9 | 1.2 | 20.6 | 11.8 | 7.5 | 6.4 |

Example 5

Analysis of Saliva Before and after Fasting

Table 4 depicts the results of the ELISA analysis of saliva collected from 50 subjects before (fasting) and after (non-fasting). FL/VOL is flow rate in ml/min, PROT is protein, LEP is leptin, LEP/PR is leptin/protein, AG is agouti related protein, AG/PR is agouti related protein/protein, INS is insulin, INS/PR is insulin/protein, X is mean values of 50 subjects, and SD is standard deviation of results.

TABLE 4

| | Saliva | | | | | | | |
|---|---|---|---|---|---|---|---|---|
| SUBJECT | BEFORE FL/VOL ml/min | AFTER FL/VOL ml/min | BEFORE PROT mg/ml | AFTER PROT mg/ml | BEFORE LEP pg/ml | AFTER LEP pg/ml | BEFORE LEP/PR | AFTER LEP/PR |
| 1 | 0.456 | | 2.483 | | 10 | | 4.03 | |
| 2 | | 0.61 | | 2.546 | | 7 | | 2.75 |
| 3 | | 0.673 | | 2.684 | | 6 | | 2.24 |
| 4 | 0.406 | | 1.941 | | | | | |
| 5 | 0.717 | | 3.623 | | 24 | | 6.62 | |
| 6 | 0.447 | 0.405 | 2.523 | 2.886 | 17 | | 6.74 | |
| 7 | 0.572 | 1.119 | 3.946 | 3.491 | 2 | 4 | 0.51 | 1.15 |
| 8 | 0.405 | | 3.473 | | | | | |
| 9 | | 0.315 | | 2.817 | | 2.177 | | |
| 10 | | 0.377 | | 2.39 | | | | |
| 11 | 0.84 | | 3.197 | | 12 | | 3.75 | |
| 12 | 0.635 | | 3.594 | | 10 | | 2.78 | |
| 13 | | 0.721 | | 3.306 | | 8 | | 2.42 |
| 14 | 0.908 | | 3.433 | | 5 | | 1.46 | |
| 15 | 0.908 | | 3.277 | | | | | |
| 16 | | 0.523 | | 3.508 | | 5 | | 1.43 |
| 17 | | 0.5 | | 2.85 | | 6 | | 2.11 |

TABLE 4-continued

| | | | Saliva | | | | | |
|---|---|---|---|---|---|---|---|---|
| 18 | 0.633 | 0.722 | 3.214 | 3.254 | 6 | 15 | 1.87 | 4.61 |
| 19 | 0.356 | | 3.3 | | 19 | | 5.76 | |
| 20 | 0.734 | | 1.855 | | 7 | | 3.77 | |
| 21 | 0.692 | | 3.398 | | | | | |
| 22 | 0.584 | | 3.646 | | | | | |
| 23 | 1.211 | 0.705 | 3.145 | 3.295 | 11 | | 3.50 | |
| 24 | 0.601 | | 2.483 | | | | | |
| 25 | 0.634 | | 1.377 | | 12 | | 8.71 | |
| 26 | 0.347 | 0.372 | 2.736 | 2.932 | 16 | | 5.85 | |
| 27 | 0.356 | | 2.413 | | 6 | | 2.49 | |
| 28 | 0.559 | | 3.012 | | 23 | | 7.64 | |
| 29 | 0.871 | | 3.076 | | 20 | | 6.50 | |
| 30 | 0.722 | | 2.091 | | | | | |
| 31 | | 0.946 | | 3.819 | | | | |
| 32 | 0.355 | | 2.989 | | | | | |
| 33 | | 0.496 | | 3.669 | | 11 | | 3.00 |
| 34 | 0.569 | | 3.456 | | 16 | | 4.63 | |
| 35 | | 0.34 | | 3.358 | | 12 | | 3.57 |
| 36 | 0.766 | | 2.033 | | 15 | | 7.38 | |
| 37 | 0.969 | | 3.024 | | 6 | | 1.98 | |
| 38 | | 0.824 | | 3.427 | | 22 | | 6.42 |
| 39 | | 0.624 | | 2.31 | | 7 | | 3.03 |
| 40 | | 0.71 | | 1.711 | | 3 | | 1.75 |
| 41 | | 0.905 | | 2.644 | | 8 | | 3.03 |
| 42 | 0.511 | | 2.483 | | 25 | | 10.07 | |
| 43 | 0.524 | 0.614 | 2.776 | 3.56 | 7 | 10 | 2.52 | 2.81 |
| 44 | 0.533 | | 3.185 | | 6 | | 1.88 | |
| 45 | 0.596 | 0.566 | 3.963 | 3.128 | 6 | 7 | 1.51 | 2.24 |
| 46 | 0.806 | | 2.068 | | 7 | | 3.38 | |
| 47 | 1.041 | 0.908 | 3.295 | 2.748 | 11 | 17 | 3.34 | 6.19 |
| 48 | 0.714 | | 2.863 | | 0 | | 0.00 | |
| 49 | 0.524 | 0.631 | 3.4 | 2.638 | 10 | 19 | 2.94 | 7.20 |
| 50 | | 0.841 | | 2.65 | | | | |
| X | 0.64 | 0.64 | 2.93 | 2.96 | 11.4 | 9.8 | 4.1 | 3.3 |
| SD | 0.21 | 0.21 | 0.62 | 0.53 | 6.7 | 5.5 | 2.6 | 1.8 |

| SUBJECT | BEFORE AG pg/ml | AFTER AG pg/ml | BEFORE AG/PR | AFTER AG/PR | BEFORE INS μIU/ml | AFTER INS μIU/ml | BEFORE INS/PR | AFTER INS/PR |
|---|---|---|---|---|---|---|---|---|
| 1 | 15 | | 6.04 | | 17 | | 6.85 | |
| 2 | | | | | | | | |
| 3 | | | | | | | | |
| 4 | 6 | | 3.09 | | 20 | | 10.30 | |
| 5 | 8 | | 2.21 | | 21 | | 5.80 | |
| 6 | 6 | 8 | 2.38 | 2.77 | 15 | 12 | 5.95 | 4.16 |
| 7 | | | | | 9 | 9 | 2.28 | 2.58 |
| 8 | 2 | | 0.58 | | 10 | | 2.88 | |
| 9 | | 8 | | 3.67 | 6 | 4 | 2.13 | 1.84 |
| 10 | | 7 | | 2.93 | | 28 | | 11.72 |
| 11 | 15 | | 4.69 | | 11 | | 3.44 | |
| 12 | 7 | | 1.95 | | 15 | | 4.17 | |
| 13 | | 2 | | 0.60 | | 19 | | 5.75 |
| 14 | | | | | 79 | | | |
| 15 | 13 | | 3.97 | | 27 | | | |
| 16 | | | | | | | | |
| 17 | | | | | | | | |
| 18 | 4 | 5 | 1.24 | 1.54 | 20 | 11 | 6.22 | 3.38 |
| 19 | 31 | | 9.39 | | 7 | | 2.12 | |
| 20 | | | | | 25 | | 13.48 | |
| 21 | 10 | | 2.94 | | 10 | | 2.94 | |
| 22 | 46 | | 12.62 | | 43 | | 11.79 | |
| 23 | 6 | 8 | 1.91 | 2.43 | 13 | 2 | 4.13 | 0.61 |
| 24 | 8 | | 3.22 | | 20 | | 8.05 | |
| 25 | 7 | | 5.08 | | 27 | | 19.61 | |
| 26 | 10 | 7 | 3.65 | 2.39 | 9 | 2 | 3.29 | 0.68 |
| 27 | 5 | | 2.07 | | 9 | | 3.73 | |
| 28 | 8 | | 2.66 | | 17 | | 5.64 | |
| 29 | 7 | | 2.28 | | 12 | | 3.90 | |
| 30 | 10 | | 4.78 | | 44 | | 21.04 | |
| 31 | | 4 | | 1.05 | | 27 | | 7.07 |
| 32 | 5 | | 1.67 | | 23 | | 7.69 | |
| 33 | | | | | | | | |
| 34 | | | | | 22 | | 6.37 | |
| 35 | | | | | | | | |
| 36 | 12 | | 5.90 | | 11 | | 5.41 | |

TABLE 4-continued

| | | | Saliva | | | | | |
|---|---|---|---|---|---|---|---|---|
| 37 | 7 | | 2.31 | | 5 | | 1.65 | |
| 38 | | | | | | | | |
| 39 | | | | | | | | |
| 40 | | 10 | | 5.84 | | | | |
| 41 | | 5 | | 1.89 | | 13 | | 4.92 |
| 42 | 10 | | 4.03 | | 13 | | 5.24 | |
| 43 | 23 | 5 | 8.29 | 1.40 | 25 | 7 | 9.01 | 1.97 |
| 44 | 8 | | 2.51 | | 4 | | 1.26 | |
| 45 | | 5 | | 1.60 | 17 | 7 | 4.29 | 2.24 |
| 46 | | | | | 15 | | 7.25 | |
| 47 | 7 | 5 | 2.12 | 1.82 | 3 | 11 | 0.91 | 4.00 |
| 48 | 11 | | 3.84 | | 19 | | 6.64 | |
| 49 | 3 | 14 | 0.88 | 5.31 | 21 | 3 | 6.18 | 1.14 |
| 50 | | 7 | | 2.64 | | | | |
| X | 10.7 | 6.7 | 3.7 | 2.5 | 18.4 | 11.1 | 6.2 | 3.7 |
| SD | 9.0 | 2.8 | 2.7 | 1.5 | 13.9 | 8.4 | 4.6 | 3.0 |

Example 6

Analysis of Plasma Before and after Fasting

Table 5 depicts the results of the ELISA analysis of plasma collected in 20 subjects before (fasting) and after (non-fasting). PROT is protein in mg/dl, LEP is leptin, LEP/PR is leptin/protein, AG is agouti related protein, AG/PR is agouti related protein/protein, INS is insulin, INS/PR is insulin/protein, X is mean values of 20 subjects, and SD is standard deviation of result.

Example 7

Analysis of Insulin Concentration in Nasal Mucus, Plasma, and Saliva

Specimens of nasal mucus from different subjects were collected and analyzed using ELISA. Table 6 depicts detection and measurement of human insulin in nasal mucus as compared to insulin in blood plasma and saliva under several physiological and pathological processes. In control subjects, in the fasting state, insulin concentrations were similar in each biological fluid measured. In the non-fasting state, the

TABLE 5

| | | | | | | | Plasma | | | | | | | |
|---|---|---|---|---|---|---|---|---|---|---|---|---|---|---|
| SUB-JECT | BE-FORE PROT mg/ml | AFTER PROT mg/ml | BE-FORE LEP pg/ml | AFTER LEP pg/ml | BE-FORE LEP/PR | AFTER LEP/PR | BE-FORE AG pg/ml | AFTER AG pg/ml | BE-FORE AG/PR | AFTER AG/PR | BE-FORE INS µIU/ml | AFTER INS µIU/ml | BE-FORE INS/PR | AFTER INS/PR |
| 1 | | 7.8 | | | | | | 35 | | 4 | | 55 | | 7 |
| 2 | | 7.2 | | | | | | | | | | 38 | | 5 |
| 3 | | 7.7 | | | | | | 37 | | 5 | | 36 | | 5 |
| 4 | | 8.6 | | | | | | 61 | | 7 | | 46 | | 5 |
| 5 | 7.9 | | 10661 | | 1349 | | 30 | | 4 | | 3 | | 0 | |
| 6 | | 6.5 | | 5345 | | | | 51 | | 8 | | 1 | | 0 |
| 7 | 6.9 | | | | | | 51 | | 7 | | 17 | | 2 | |
| 8 | 7.6 | | | | | | 38 | | 5 | | | | | |
| 9 | 7.9 | | | | | | 34 | | 4 | | 41 | | 5 | |
| 10 | | 7.4 | | | | | | 28 | | 4 | | 6 | | 1 |
| 11 | 7.1 | | | | | | 53 | | 7 | | | | | |
| 12 | 6.2 | 6.2 | 1793 | 1714 | 289 | 276 | 65 | | 10 | | 95 | 60 | 15 | 10 |
| 13 | 7.2 | | 5075 | | 705 | | 25 | | 3 | | 4 | | 1 | |
| 14 | | 7.2 | | | | | | 70 | | 10 | | 24 | | 3 |
| 15 | | 6.6 | | | | | | 34 | | 5 | | | | |
| 16 | | 7.2 | | 16860 | | 2342 | | 55 | | 8 | | 44 | | 6 |
| 17 | | 7.9 | | 16860 | | 2134 | | 33 | | 4 | | 1 | | 0 |
| 18 | | 7.3 | | 15826 | | 2168 | | 37 | | 5 | | 7 | | 1 |
| 19 | | 7.3 | | | | | | 37 | | 5 | | 18 | | 2 |
| 20 | | 6.6 | | | | | | 58 | | 9 | | | | |
| X | 7 | 7 | 5843 | 11321 | 781 | 1730 | 42 | 45 | 6 | 6 | 32 | 28 | 5 | 4 |
| SD | 1 | 1 | 4484 | 7240 | 534 | 973 | 14 | 14 | 3 | 2 | 38 | 21 | 6 | 3 | nasal mucus concentrations were significantly lower than in plasma or saliva. In obese subjects and in diabetics, in the fasting state, insulin concentrations were similar in plasma and nasal mucus but slightly elevated in saliva. However, in the non-fasting state, insulin concentrations increased in plasma and saliva in response to increased carbohydrate intake but in nasal mucus, insulin levels decreased.

ological and pathological conditions. In control subjects in the fasting state, insulin receptor concentrations measured were similar in plasma, saliva as well as nasal mucus. However, in the non-fasting state, where there was little change in receptor concentrations in plasma or saliva, there was a significant decrease in nasal mucus receptor concentration. In obese subjects and in diabetics, in the fasting state, insulin receptor concentrations decreased in each biological fluid measured. However, in the non-fasting state, there were no further decreases in receptor concentrations in plasma or in saliva but there was a decrease in receptor concentration in nasal mucus associated with an increase in carbohydrate intake.

TABLE 6

Insulin in plasma, saliva, and nasal mucus

| | AGE (years) | WEIGHT (lbs) | PLASMA GLUCOSE mg/ml | PLASMA μIU/ml | SALIVA μIU/ml | NASAL MUCUS μIU/ml |
|---|---|---|---|---|---|---|
| SUBJECTS | | | | | | |
| CONTROLS (56) | 56 ± 2 | 174 ± 8 | | | | |
| FASTING | | | 88 ± 1 | 17.1 ± 3.7 | 18.9 ± 2.3 | 19.0 ± 2.2 |
| NON-FASTING | | | 174 ± 8 | 29.4 ± 4.4 | 22.6 ± 2.6 | 7.5 ± 0.9 [c] |
| SUBJECTS (11) | | | | | | |
| OBESE | 51 ± 6 | 259 ± 26 | | | | |
| FASTING | | | 110 ± 24 | 20.0 ± 6.2 [†] | 34.1 ± 7.9 | 18.4 ± 6.5 |
| NON-FASTING | | | 259 ± 26 | 38.2 ± 11.7 | 36.3 ± 6.3 | 7.5 ± 2.6 [d b a] |
| DIABETES | 51 ± 6 | 243 ± 52 | | | | |
| FASTING | | | 142 ± 37 | 22.7 ± 10.2 | 36.8 ± 9.0 | 21.0 ± 9.3 |
| NON-FASTING | | | 243 ± 42 | 39.5 ± 19.0 | 38.2 ± 9.6 | 7.6 ± 2.3 [b] |

( ) Subject number
[†] MEAN ± SEM
[a] $p < 0.01$ with respect to non-fasting saliva
[b] $p < 0.005$ with respect to fasting saliva
[c] $p < 0.001$ with respect to fasting nasal mucus and non-fasting plasma, saliva
[d] $p < 0.05$ with respect to fasting plasma, non-fasting plasma
[e] $p < 0.02$ with respect to fasting plasma Example 8

Analysis of Insulin Receptor Concentration in Nasal Mucus, Plasma, and Saliva

Table 7 depicts the detection and measurement of human insulin receptor in nasal mucus as compared to the insulin receptor in plasma and saliva under several physi-

TABLE 7

Insulin receptor concentration in plasma, saliva, and nasal mucus

| | AGE (years) | WEIGHT (lbs) | PLASMA GLUCOSE mg/ml | PLASMA mg/ml | SALIVA mg/ml | NASAL MUCUS mg/ml |
|---|---|---|---|---|---|---|
| SUBJECTS (56) | | | | | | |
| CONTROLS (56) | 56 ± 2 [†] | 174 ± 8 | 84 ± 1 [$] | | | |
| FASTING | | | 88 ± 6 | 8.7 ± 1.8 [†] | 7.6 ± 0.7 | 8.5 ± 1.7 |
| NON-FASTING | | | 174 ± 8 | 7.5 ± 1.4 | 7.6 ± 0.6 | 3.2 ± 0.6 [a] |
| SUBJECTS (11) | | | | | | |
| OBESE | 51 ± 6 [‡] | 259 ± 26 | | | | |
| FASTING | | | 110 ± 24 [$] | 2.9 ± 0.9 [† b] | 6.0 ± 1.2 | 4.8 ± 0.6 [d] |
| NON-FASTING | | | 259 ± 26 | 3.0 ± 0.3 [b] | 5.2 ± 0.8 [c] | 2.1 ± 0.5 |
| THIN | | 122 ± 6 | | | | |
| FASTING | | | | | | 8.4 ± 2.7 |

TABLE 7-continued

Insulin receptor concentration in plasma, saliva, and nasal mucus

| | AGE (years) | WEIGHT (lbs) | PLASMA GLUCOSE mg/ml | PLASMA mg/ml | SALIVA mg/ml | NASAL MUCUS mg/ml |
|---|---|---|---|---|---|---|
| NON-FASTING DIABETES (4) | | 243 ± 52 | | | 9.4 ± 4.6 | |
| FASTING | | | 142 ± 37 | 4.0 ± 1.7 [b] | 4.0 ± 0.6 [c] | 4.7 ± 1.9 |
| NON-FASTING | | | 243 ± 42 | 3.4 ± 0.6 [a] | 4.6 ± 1.9 | 2.3 ± 1.6 |

[†] MEAN ± SEM
[‡] years
[$] mg/dl
[a] $p < 0.01$ with respect to nasal mucus fasting, plasma (fasting, non-fasting), saliva (fasting, non-fasting)
[b] $p < 0.005$ with respect to controls
[c] $p < 0.001$ with respect to controls
[d] $p < 0.05$ with respect to controls These results in Tables 6 and 7 indicate that the characteristics of nasal mucus reflect physiological and pathological conditions. The detection of the presence of insulin or insulin receptors in nasal mucus may offer an alternative method for diagnosis of diabetes, other disorders of carbohydrate metabolism and physiological measurements of insulin and insulin receptors. Its ease of measurement using a non-invasive technique may be preferable to invasive techniques such as venipucture. Its presence in nasal mucus may also offer a view into other aspects of both human physiology and pathology. In the non-fasting state insulin receptor concentration is down regulated to some extent under some conditions but is uniformly regulated in nasal mucus indicating that, its concentration in nasal mucus may indicate physiological phenomenon such as, appetite and brain, and the signal characteristics reflecting base human physiology and pathology. Its presence may influence human immune and autoimmune responses.

Example 9

Pearson-Product-Moment Correlations of Insulin with Plasma Glucose and Insulin with Weight Table 8 depicts Pearson-product-moment correlations of insulin with plasma glucose and insulin with weight. There was little positive correlation among controls in insulin in plasma or insulin in saliva, in either the fasting or non-fasting state. However, in nasal mucus this correlation was negative, indicating a down regulated direction. This signal in nasal mucus may reflect a control mechanism of appetite. Thus, in nasal mucus there may be substances which reflect both physiological parameters common or uncommon to blood or saliva which provides methods to diagnose body physiological and pathological events.

TABLE 8

Correlation (pearson product moment (r)) between insulin and independent variable (N = 60)

| | INSULIN CONCENTRATION | | | | | |
|---|---|---|---|---|---|---|
| | PLASMA (r) | | SALIVA (r) | | NASAL MUCUS (r) | |
| | FASTING | NON-FASTING | FASTING | NON-FASTING | FASTING | NON-FASTING |
| VARIABLE (CONTROLS) | | | | | | |
| PLASMA GLUCOSE(mg/dl) | 0.16 | 0.08 | 0.25 | 0.26 | −0.20 | −0.14 |
| WEIGHT(lbs) | 0.04 | 0.24 | 0.26 | 0.38 | −0.14 | −0.18 |
| VARIABLE (OBESE) | | | | | | |
| PLASMA GLUCOSE(mg/dl) | 0.87 | −0.01 | 0.33 | 0.39 | −0.30 | −0.37 |
| WEIGHT(lbs) | 0.62 | 0.72 | 0.08 | 0.65 | −0.44 | −0.55 |
| VARIABLE (DIABETES) | | | | | | |
| PLASMA GLUCOSE(mg/dl) | 1.00 [a] | 1.00 [a] | 0.65 | 0.59 | −0.26 | −0.64 |
| WEIGHT(lbs) | 1.00 | 0.99 [a] | 0.69 | 0.69 | −0.28 | −0.66 |

[a] $p < 0.01$

Example 10

Pearson-Product-Moment Correlations of Insulin Receptor with Plasma Glucose and Insulin Receptor with Weight Table 9 depicts relationships between insulin receptor concentration with plasma glucose and weight. There was little positive correlation among controls amongst insulin receptors in plasma or insulin receptors in saliva, in either the fasting or non-fasting state. However, in nasal mucus this correlation was negative, indicating a down regulated direction. This signal in nasal mucus may reflect a control mechanism of appetite. Thus, in nasal mucus there may be substances which reflect both physiological parameters common or uncommon to blood or saliva which may provide methods to diagnose body physiological and pathological events.

TABLE 9

Correlation (pearson product moment (r)) between insulin receptor concentration and independent variable (n = 60)

| | INSULIN RECEPTOR CONCENTRATION | | | | | |
|---|---|---|---|---|---|---|
| | PLASMA (r) | | SALIVA (r) | | NASAL MUCUS (r) | |
| | FASTING | NON-FASTING | FASTING | NON-FASTING | FASTING | NON-FASTING |
| VARIABLE (CONTROLS) | | | | | | |
| PLASMA GLUCOSE(mg/dl) | 0.20 | 0.12 | −0.24 | −0.14 | 0.03 | 0.11 |
| WEIGHT(lbs) | −0.11 | −0.07 | −0.08 | −0.19 | −0.21 | −0.17 |
| VARIABLE (OBESE) | | | | | | |
| PLASMA GLUCOSE(mg/dl) | 0.70 | 0.20 | −0.51 | −0.08 | 0.41 | 0.19 |
| WEIGHT(lbs) | −0.18 | −0.33 | 0.09 | −0.16 | 0.24 | −0.09 |

TABLE 9-continued

Correlation (pearson product moment (r)) between insulin receptor concentration and independent variable (n = 60)

| | INSULIN RECEPTOR CONCENTRATION ||||||
|---|---|---|---|---|---|---|
| | PLASMA (r) || SALIVA (r) || NASAL MUCUS (r) ||
| | FASTING | NON-FASTING | FASTING | NON-FASTING | FASTING | NON-FASTING |
| VARIABLE (DIABETES) | | | | | | |
| PLASMA GLUCOSE(mg/dl) | −0.57 | −0.43 | −0.78 | 0.25 | 0.15 | −0.22 |
| WEIGHT(lbs) | −0.60 | −0.52 | 0.56 | −0.34 | 0.18 | −0.19 |

Example 11

Analysis of Caspase 3 in Nasal Mucus and Saliva

Caspase 3 is one of the apoptotic substances involved in the apoptotic process. Table 10 illustrates a comparison between the detection and measurement of caspase 3 in nasal mucus and in saliva in 18 subjects. The presence of caspase in nasal mucus is about 13% of that in saliva and reflects the magnitude of the apoptotic process. The presence of caspase in nasal mucus indicates the activity of cellular death in both physiological and pathological processes.

diverse disease processes makes their diagnosis possible on a clinical basis since obtaining cellular diagnosis through tissue biopsy can not only be invasive but also difficult and at times dangerous. The concentration of TNFα in nasal mucus can be reflective of underlying disease processes and is easier to obtain. These results may make the use of this fluid an important method of diagnosis for these pathological processes which cannot be as conveniently made in plasma. These data suggest that various cancers can be diagnosed by measurements of TNFα in nasal mucus and their treatment can be monitored by following its concentration in nasal mucus.

TABLE 10

Caspase 3 in human saliva and nasal mucus

| | SALIVA ||| NASAL MUCUS |||
|---|---|---|---|---|---|---|
| Subjects | CASPASE 3 μg/ml | PROTEIN mg/dl | CASPASE 3 PROTEIN | CASPASE 3 μg/ml | PROTEIN mg/dl | CASPASE 3 PROTEIN |
| 18 | 2.87 ± 0.70[†] | 2.7 ± 0.2 | 2.88 ± 0.28 | 0.38 ± 0.13 | 2.2 ± 0.2 | 0.38 ± 0.17 |

[†]MEAN ± SEM

Example 12

Analysis of TNFα in Nasal Mucus and Saliva

Table 11 illustrates detection and measurement of TNFα in nasal mucus and saliva in 75 subjects. Results indicate that TNFα in nasal mucus is about 30 times higher than in saliva. Elevated levels of this substance in nasal mucus in Since levels of TNFα may also reflect the inflammatory aspects of disease processes inducing it, use of anti TNFα drugs through nasal administration may reflect a method of treating these various disease processes. Concentrations of TNFα in nasal mucus in patients with smell loss can be greater than for example, 5000 times that found in normal subjects thereby reflecting its function as a "death protein" indicator of excessive apoptosis as in its role in cancer.

TABLE 11

TNFα in human saliva and nasal mucus

| | SALIVA ||| NASAL MUCUS |||
|---|---|---|---|---|---|---|
| Subjects | TNFα μg/ml | PROTEIN mg/dl | TNFα PROTEIN | TNFα μg/ml | PROTEIN mg/dl | TNFα PROTEIN |
| 75 | 0.43 ± 0.03[†] | 3.1 ± 0.1 | 0.15 ± 0.01 | 12.8 ± 1.6[a] | 2.4 ± 0.09[a] | 5.5 ± 1.3[a] |

[†]MEAN ± SEM
With respect to saliva
[a]$p < 0.001$

Example 13

Analysis of TNFR I in Nasal Mucus and Saliva

Table 12 illustrates detection and measurement of TNFR I in 47 subjects. Results indicate that TNFR I in nasal mucus is about 16 times its concentration in saliva and its concentration is significantly increased over that found in plasma, red blood cells, or urine. The results show that TNFR I present in nasal mucus can reflect activity of many inflammatory, oncological and other pathological processes, including taste and smell dysfunction. Thus the methods of the present invention can be used to detect and establish clinical diagnoses of excessive apoptosis and can be used as a treatment modality in inhibiting pathological apoptosis.

TABLE 12

TNF receptor I in human saliva and nasal mucus

| | SALIVA | | | NASAL MUCUS | | |
|---|---|---|---|---|---|---|
| Subjects | TNFR I µg/ml | PROTEIN mg/dl | TNFR I PROTEIN | TNFR I µg/ml | PROTEIN mg/dl | TNFR I PROTEIN |
| 47 | $110 \pm 13^{\dagger}$ | $3.1 \pm 0.1$ | $38 \pm 5$ | $1753 \pm 357^{a}$ | $2.2 \pm 0.1^{a}$ | $837 \pm 161^{a}$ |

$^{\dagger}$MEAN ± SEM
With respect to saliva
$^{a}p < 0.001$

Example 14

Analysis of TNFR II in Nasal Mucus and Saliva

Table 13 illustrates detection and measurement of TNFR II in 47 subjects. Results indicate that TNFR II in nasal mucus is about 24 times its concentration in saliva and its concentration in nasal mucus is significantly higher than found in plasma, red blood cells, or urine. The results reflect that TNFR II present in nasal mucus provides a non invasive method of diagnosing various pathological processes. Thus the methods of the present invention can be used to detect and establish clinical diagnoses of excessive apoptosis and can be used as a treatment modality in inhibiting pathological apoptosis.

TABLE 13

TNF receptor II in human saliva and nasal mucus

| | SALIVA | | | NASAL MUCUS | | |
|---|---|---|---|---|---|---|
| Subjects | TNFR II µg/ml | PROTEIN mg/dl | TNFR II PROTEIN | TNFR II µg/ml | PROTEIN mg/dl | TNFR II PROTEIN |
| 47 | $48 \pm 2^{\dagger}$ | $3.1 \pm 0.1$ | $17 \pm 0.9$ | $1126 \pm 217^{a}$ | $2.2 \pm 0.1^{a}$ | $578 \pm 128^{a}$ |

$^{\dagger}$MEAN ± SEM
With respect to saliva
$^{a}p < 0.001$

Example 15

Analysis of TRAIL in Nasal Mucus and Saliva

Tables 14 and 15 illustrate detection and measurement of TRAIL in saliva and nasal mucus in normal subjects and in patients with smell loss. In Table 14, results indicate that TRAIL in nasal mucus is about 5 times higher than in saliva and both are significantly higher than in blood, red blood cells, or urine. TRAIL in nasal mucus in some patients with smell and taste loss varies from 500-10,000 times higher than in normal subjects and it may be elevated in nasal mucus in patients with inflammatory and oncological disease processes. Mean levels of increased TRAIL in nasal mucus reveal levels significantly greater than in other fluids. The results provide a non-invasive method for detecting TRAIL in nasal mucus.

that treatment with theophylline which returned smell function to normal in a dose-dependent manner was associated with a dose-dependent decrease in TRAIL, which indicates a decrease in the abnormal apoptotic processes. These data indicate both a biochemical and functional improvement in smell function by treatment with theophylline.

TABLE 14

Trail in saliva and nasal mucus in normal subjects and in patients with smell loss

| | SALIVA | | | NASAL MUCUS | | |
|---|---|---|---|---|---|---|
| SUBJECTS (Number) | TRAIL µg/ml | PROTEIN mg/dl | TRAIL PROTEIN | TRAIL µg/ml | PROTEIN mg/dl | TRAIL PROTEIN |
| NORMALS(17) | 336 ± 48[†] | 2.7 ± 0.1 | 122 ± 14 | 1639 ± 89 | 2.2 ± 0.01 | 770 ± 35 |
| PATIENTS(10) | 353 ± 31 | 2.7 ± 0.2 | 141 ± 20 | 2584 ± 430 | 1.4 ± 0.2 | 4753 ± 1400 |

[†]MEAN ± SEM

TABLE 15

Trail in saliva and nasal mucus in normal subjects and in patients with Hyposmia

| | SALIVA | | | | NASAL MUCUS | | |
|---|---|---|---|---|---|---|---|
| SUBJECTS(Number) | PROTEIN mg/dl | TRAIL µg/ml | FLOW RATE ml/sec | TRAIL FLOW RATE | PROTEIN mg/dl | TRAIL µg/ml | TRAIL PROTEIN |
| NORMALS(28) | 2.29 ± 0.10[†] | 123 ± 6 | 0.80 ± 0.03 | 343 ± 13 | 2.65 ± 0.12 | 1990 ± 119 | 7.56 ± 28 |
| PATIENTS(65) | 2.96 ± 0.09 | 330 ± 25[a] | 0.63 ± 0.03 | 582 ± 55[a] | 1.97 ± 0.11 | 4121 ± 54[a] | 3095 ± 591[a] |

( )Subject number
[†]Mean ± SEM
[a]$p < 0.001$ with respect to normal

Example 16

Analysis of TRAIL in Nasal Mucus in Patients with Hyposmia Before and after Treatment with Theophylline Table 16 illustrates detection and measurement of TRAIL in nasal mucus in patients with hyposmia before and after treatment with theophylline at various doses. Data indicate

TABLE 16

Nasal mucus Trail in patients with hyposmia before and after treatment with theophylline at various doses

| | | | THEOPHYLLINE TREATMENT | | | | | |
|---|---|---|---|---|---|---|---|---|
| | PRETREATMENT | | 200 mg | | 400 mg | | 600 mg | |
| SUBJECTS (Number) | TRAIL µg/ml | PROTEIN mg/dl | TRAIL µg/ml | PROTEIN mg/dl | TRAIL µg/ml | PROTEIN mg/dl | TRAIL µg/ml | PROTEIN mg/dl |
| PATIENTS(5) | 2584 | 1.36 | 855 | 1.29 | 791 | 2.06 | 247 | 2.00 |
| NORMALS(9) | 335 | | | | | | | |

[†] MEAN ± SEM

Example 17

Analysis of IL2 in Saliva and Nasal Mucus

Table 17 illustrates levels of IL2 in human nasal mucus and saliva. IL2 was not present in nasal mucus although it was found in plasma.

TABLE 17

| | IL 2 in human saliva and nasal mucus | | | | | |
|---|---|---|---|---|---|---|
| | SALIVA | | | NASAL MUCUS | | |
| SUBJECTS (Number) | IL 2 µg/ml | PROTEIN mg/dl | IL 2 PROTEIN | IL 2 µg/ml | PROTEIN mg/dl | IL 2 PROTEIN |
| (10) | 0 | 3.1 ± 0.2[†] | 0 | 0 | 2.2 ± 0.1 | 0 |

[†]MEAN ± SEM

Example 18

Analysis of IL3 in Saliva and Nasal Mucus

Table 18 illustrates measured IL 3 in both human saliva and nasal mucus. Levels of IL 3 in nasal mucus were found to be about ½ A the concentration in saliva but both levels were higher than that found in plasma, red blood cells, or urine. IL 3 present in nasal mucus provides a non invasive method of diagnosing various IL3 related diseases.

TABLE 18

| | IL 3 in human saliva and nasal mucus | | | | | |
|---|---|---|---|---|---|---|
| | SALIVA | | | NASAL MUCUS | | |
| SUBJECTS (Number) | IL 3 µg/ml | PROTEIN mg/dl | IL 3 PROTEIN | IL 3 µg/ml | PROTEIN mg/dl | IL 3 PROTEIN |
| (17) | 140 ± 32[†] | 3.1 ± 0.2 | 48 ± 15 | 63 ± 24 | 2.2 ± 0.1 | 43 ± 12 |

[†]MEAN ± SEM

Example 19

Analysis of Endostatin in Human Plasma, Urine, Saliva and Nasal Mucus

Table 19 illustrates detection and measurement of endostatin in plasma, urine, saliva and nasal mucus in 15 subjects. Endostatin levels in nasal mucus were 5 times higher than in saliva and about 7% of that found in plasma. On the basis of the endostatin/protein ratio, levels in nasal mucus are about 14% of that found in plasma. Presence of this 20 KD protein in nasal mucus illustrates a non-invasive method of detection of endostatin in nasal mucus and its use in diagnosing various endostatin related diseases. It may also be indicative of its synthesis in nasal mucus.

TABLE 19

| Endostatin in human plasma, urine, saliva and nasal mucus | | | | |
|---|---|---|---|---|
| BIOLOGICAL FLUIDS | (15) | ENDOSTATIN µg/ml | PROTEIN mg/dl | ENDOSTATIN PROTEIN |
| PLASMA | | 94 ± 10[†] | 6.9 ± 0.10 | 15 ± 1 |
| URINE | | 0.5 ± 0.04[a] | — | — |
| SALIVA | | 1.3 ± 0.3[a] | 2.6 ± 0.2 | 0.59 ± 0.04[a] |
| NASAL MUCUS | | 6.6 ± 1.3[a] | 3.0 ± 0.2 | 2.0 ± 0.43[a] |

( ) Subject number
[†]MEAN ± SEM
[a]$p < 0.001$ with respect to plasma

Example 20

Analysis of Erythropoetin (EPO) in Plasma, Urine, Saliva and Nasal Mucus

Table 20 illustrates detection and measurement of EPO in plasma, urine, saliva and nasal mucus. EPO was not found in urine or saliva. The level of EPO in nasal mucus was found to be between 1.1 and 4.5 times higher than in plasma. Presence of EPO in nasal mucus illustrates a non-invasive method of detection of EPO in nasal mucus and its use in diagnosing various EPO related diseases.

TABLE 20

EPO in plasma, urine, saliva and nasal mucus

| BIOLOGICAL FLUIDS | (27) | ERYTHRO-POETIN µIU/ml | PROTEIN mg/dl | ERYTHRO-POETIN PROTEIN |
|---|---|---|---|---|
| PLASMA |  | 13 ± 2[†] | 7.2 ± 0.1 | 2 ± 0.3 |
| URINE |  | 0 | 0 | 0 |
| SALIVA |  | 0 | 0 | 0 |
| NASAL MUCUS |  | 15 ± 5 | 2.9 ± 0.1[a] | 9 ± 2[b] |

( ) Subject number
[†]MEAN ± SEM
[a]$p < 0.001$ with respect to plasma
[b]$p < 0.005$ with respect to plasma Example 21

Analysis of Bone Morphogenic Protein (BMP) in Plasma, Urine, Saliva and Nasal Mucus Table 21 illustrates detection and measurement of BMP I in plasma, urine, saliva and nasal mucus in 20 subjects. BMP I was found in plasma but not in urine, saliva or nasal mucus.

TABLE 21

BMP in plasma, urine, saliva and nasal mucus

| BIOLOGICAL FLUIDS | (20) | BMP µg/ml | PROTEIN mg/dl | BMP PROTEIN |
|---|---|---|---|---|
| PLASMA |  | 30 ± 6[†] | 3.6 ± 0.5 | 0 |
| URINE |  | 0 | 0 | 0 |
| SALIVA |  | 0 | 0 | 0 |
| NASAL MUCUS |  | 0 | 0 | 0 |

( ) Subject number
[†]MEAN ± SEM

Example 22

Analysis of Brain Derived Neurotrophic Factor (BDNF) in Human Plasma, Urine, Saliva and Nasal Mucus Table 22 illustrates detection and measurement of BDNF in plasma, urine, saliva and nasal mucus in 20 subjects. BDNF was found in plasma and nasal mucus but not in urine or saliva. Levels of BDNF in plasma were higher than in nasal mucus. The results indicate that nasal mucus may be a repository of the family of nerve growth factors and the concentration of BDNF as shown in Table 22, may help understand both the physiology and pathology of neurotrophic factors related to growth and homeostasis of cells in the nasal cavity as well as reporting on the presence of these factors in the systemic circulation.

TABLE 22

BDNF in human plasma, urine, saliva and nasal mucus

| BIOLOGICAL FLUIDS | (20) | BDNF µg/ml | PROTEIN mg/dl | BDNF PROTEIN |
|---|---|---|---|---|
| PLASMA |  | 3391 ± 530 | 7.1 ± 0.01 | 447 ± 74 |
| URINE |  | 0 | — |  |
| SALIVA |  | 0 | 2.7 ± 0.2 |  |
| NASAL MUCUS |  | 11 ± 7 | 3.2 ± 0.3 | 8 ± 6 |

( ) Subject number
[†]MEAN ± SEM

Example 23

Analysis of Ciliary Neurotrophic Factor (CNTF) in Human Plasma, Urine, Saliva and Nasal Mucus Table 23 illustrates detection and measurement of CNTF in plasma, urine, saliva and nasal mucus in 19 subjects. Levels of CNTF in plasma and nasal mucus were found to be similar but lower in saliva. These results indicate that measurement of CNTF in nasal mucus may be used as an index for the levels of CNTF in plasma. The results provide a non-invasive method for the detection of CNTF in nasal mucus. The detection of CNTF in nasal mucus provides a non invasive method of diagnosing various CNTF related diseases.

TABLE 23

CNTF in human plasma, urine, saliva and nasal mucus

| BIOLOGICAL FLUIDS | (19) | CNTF µg/ml | PROTEIN mg/dl | CNTF PROTEIN |
|---|---|---|---|---|
| PLASMA |  | 0.004 ± 0.001 | 3.1 ± 0.1 | 0 |
| URINE |  | 0 |  |  |
| SALIVA |  | 0.001 ± 0.001 | 3.0 ± 0.1 | 0 |
| NASAL MUCUS |  | 0.003 ± 0.001 | 2.2 ± 0.1 | 0 |

( ) Subject number

Example 24

Analysis of Granulocyte Macrophage Growth Factor (GM-CSF) in Human Plasma, Urine, Saliva and Nasal Mucus Table 24 illustrates detection and measurement of GM-CSF in plasma, urine, saliva and nasal mucus in 16 subjects. Levels in nasal mucus were found to be over 6 times that found in plasma. The results provide a non-invasive method for the detection of GM-CSF in nasal mucus. The results also indicate nasal mucus to be a source of GM-CSF. The detection GM-CSF present in nasal mucus provides a non invasive method of diagnosing various GM-CSF related diseases.

TABLE 24

GM-CSF in human plasma, urine, saliva and nasal mucus

| BIOLOGICAL FLUIDS | (16) | GM-CSF µg/dl | PROTEIN mg/dl | GM-CSF PROTEIN |
|---|---|---|---|---|
| PLASMA |  | 0.42 ± 0.31[†] | 7.2 ± 0.1 | 0.036 ± 0.034 |
| URINE |  | 0 |  | 0 |
| SALIVA |  | 0 |  | 0 |
| NASAL MUCUS |  | 2.55 ± 0.8 | 2.9 ± 0.1 | 0.58 ± 0.25[a] |

( ) Subject number
[†]MEAN ± SEM
[a]$p < 0.001$ with respect to plasma

Example 25

Analysis of Hepatocyte Growth Factor (HGF) in Human Plasma, Urine, Saliva, and Nasal Mucus Table 25 illustrates detection and measurement of HGF in plasma, urine, saliva and nasal mucus in 17 subjects. Concentrations of HGF in nasal mucus were found to be higher than that found in either plasma or urine. These results suggest that HGF may be synthesized in the serous glands of the nose for a specific mechanism involved with nasal homeostasis as well as a mechanism involved with systemic cell migration. The results provide a non-invasive method for the detection of HGF in nasal mucus.

TABLE 25

HGF in human plasma, urine, saliva and nasal mucus

| BIOLOGICAL FLUIDS | (17) | HGF µg/ml | PROTEIN mg/dl | HGF PROTEIN |
|---|---|---|---|---|
| PLASMA | | 709 ± 91[†] | 3.1 ± 0.1 | 100 ± 13 |
| URINE | | 623 ± 126 | — | — |
| SALIVA | | 0 | | 0 |
| NASAL MUCUS | | 2015 ± 431[a] | 2.2 ± 0.1 | 924 ± 227[a] |

( ) Subject number
[†]MEAN ± SEM
With respect to plasma and urine
[a]$p < 0.001$

Example 26

Analysis of Platelet Derived Growth Factor (PDGF) in Human Plasma, Urine, Saliva and Nasal Mucus Table 26 illustrates detection and measurement of PDGF in human plasma, urine, saliva and nasal mucus in 18 subjects. Concentrations of PDGF expressed per mg protein were found to be higher in saliva and nasal mucus than in plasma. These results suggest that PDGF may be synthesized in the serous glands of the nose for a specific mechanism involved with nasal homeostasis. The results provide a non-invasive method for the detection of PDGF in nasal mucus.

TABLE 26

PDGF in human plasma, urine, saliva and nasal mucus

| BIOLOGICAL FLUIDS | (18) | PDGF µg/dl | PROTEIN mg/dl | PDGF PROTEIN |
|---|---|---|---|---|
| PLASMA | | 510 ± 153[†] | 6.9 ± 0.1 | 71 ± 21 |
| URINE | | 5 ± 2 | — | — |
| SALIVA | | 600 ± 176 | 2.6 ± 0.2 | 215 ± 18[a] |
| NASAL MUCUS | | 482 ± 87 | 3.0 ± 0.2 | 175 ± 32[b] |

( ) Subject number
[†]MEAN ± SEM
[a]$p < 0.001$ with respect to plasma
[b]$p < 0.02$ with respect to plasma

Example 27

Analysis of Carbonic Anhydrase VI (CA VI) Concentration

Table 27 illustrates decrease in CA VI in patients with smell and taste loss. These results provide a method for the detection and measurement of CA VI in nasal mucus as an index of smell and taste loss and its continual measurement during treatment of these disorders in order to monitor efficacy of therapy.

TABLE 27

CA VI concentrations in nasal mucus in normal subjects and in patients with smell loss

| SUBJECTS | | PROTEIN mg/dl | ZINC µg/L | COPPER µg/L | CA VI mg/ml |
|---|---|---|---|---|---|
| NORMALS | (8) | 3.41 ± 0.02[†] | 97 ± 8 | 102 ± 8 | 0.287 ± 0.056 |
| MEN | (5) | 2.96 ± 0.30 | 100 ± 11 | 78 ± 26 | 0.238 ± 0.03 |
| WOMEN | (3) | 3.54 ± 2.04 | 90 ± 8 | 103 ± 15 | 0.369 ± 0.26 |
| PATIENTS | (70) | 2.27 ± 0.04 | | | 0.157 ± 0.13 |
| MEN | (39) | 2.21 ± 0.14[a] | 182 ± 17 | 118 ± 14 | 0.158 ± 0.020 |
| WOMEN | (31) | 2.34 ± 0.18[a] | 171 ± 21 | 126 ± 12 | 0.155 ± 0.014 |

( ) Subject number
[†]Mean ± SEM
Compared to normals
[a]$p < 0.001$

Example 28

Analysis of Loss of Smell Function by Disease Etiology

Table 28 illustrates loss of smell function by disease etiology with respect to measurements of CA VI concentration in nasal mucus. Results indicate that patients with post influenza hyposmia hypogeusia (PIHH), allergic rhinitis and post anesthesia have significantly decreased CA VI concentrations in nasal mucus. These results provide a method for the detection and measurement of CA VI in nasal mucus as an index of smell and taste loss and its continual measurement during treatment of these disorders in order to monitor efficacy of therapy. The detection of CA VI in nasal mucus provides a non invasive method of diagnosing various diseases related to human physiology and pathology.

TABLE 28

Carbonic Anhydrase VI concentrations in nasal mucus in normal subjects and in patients with smell loss

| CONDITION | | PROTEIN mg/dl | ZINC µg/L | COPPER µg/L | CA VI µg/ml |
|---|---|---|---|---|---|
| NORMALS | (11) | 3.17 ± 0.48[†] | 97 ± 7 | 102 ± 7 | 0.287 ± 0.044 |
| PIHH | (26) | 2.39 ± 0.19 | 139 ± 18[a] | 105 ± 11[a] | 0.186 ± 0.02[c] |

TABLE 28-continued

Carbonic Anhydrase VI concentrations in nasal mucus in normal subjects and in patients with smell loss

| CONDITION | | PROTEIN mg/dl | ZINC µg/L | COPPER µg/L | CA VI µg/ml |
|---|---|---|---|---|---|
| ALLERGIC RHINITIS | (25) | 2.34 ± 0.19 | 234 ± 24[a] | 139 ± 20 | 0.141 ± 0.018[b] |
| POST ANESTHESIA | (6) | 1.65 ± 0.30[b] | 189 ± 60 | 139 ± 40 | 0.156 ± 0.047[a] |
| PHANTAGEUSIA | (5) | 2.30 ± 0.59 | 170 ± 49 | 158 ± 31 | 0.180 ± 0.054 |

( ) Subject number
[†]Mean ± SEM
Compared to normals
[a]$p < 0.001$
[b]$p < 0.025$
[c]$p < 0.05$ Example 29

Analysis of cAMP and cGMP in Human Nasal Mucus and in Parotid Saliva

Table 29 illustrates detection and measurement of cAMP and cGMP in saliva and in nasal mucus in normal subjects. Results show that patients with smell loss had decreased levels of cAMP in their nasal mucus. These results indicate that cAMP in nasal mucus can be an index of smell loss and that its secretion may be inhibited in smell loss. Thus, monitoring of cAMP in the nasal mucus can be a diagnostic tool for the treatment of diseases related to cAMP. Results also indicate that there was less significant difference between cGMP in human nasal mucus and in parotid saliva. The results provide a non-invasive method for the detection of cAMP and cGMP in nasal mucus.

TABLE 29

Comparison of cAMP and cGMP in human nasal mucus and in parotid saliva

| | NASAL MUCUS | PAROTID SALIVA[††] |
|---|---|---|
| TOTAL | | |
| cAMP* | 0.22 ± 0.07[†$] | 2.00 ± 0.31 |
| cGMP | 0.25 ± 0.08 | 0.21 ± 0.04 |
| MEN | | |
| cAMP | 0.21 ± 0.13[$] | 1.58 ± 0.43 |
| cGMP | 0.28 ± 0.16 | 0.23 ± 0.06 |
| WOMEN | | |
| cAMP | 0.23 ± 0.06[$] | 3.38 ± 0.35 |
| cGMP | 0.24 ± 0.13 | 0.20 ± 0.07 |
| PROTEIN** | | |
| TOTAL | 3.24 ± 0.22 | 3.11 ± 0.18 |

TABLE 29-continued

Comparison of cAMP and cGMP in human nasal mucus and in parotid saliva

| | NASAL MUCUS | PAROTID SALIVA[††] |
|---|---|---|
| MEN | 3.32 ± 0.02 | 3.39 ± 0.34 |
| WOMAN | 3.51 ± 0.75 | 2.93 ± 0.02 |

*in pmol/ml
**mg/ml
[†]MEAN ± SEM
[††]Collected in 171 subjects
[$]$p < 0.001$ compared to parotid saliva Example 30

Analysis of cAMP and cGMP in Human Nasal Mucus in Normal Subjects and in Patients Table 30 illustrates comparison of the measurement of cAMP and cGMP in normal subjects with the patients with taste and smell loss. Results show that patients with smell loss had decreased levels of cAMP in their nasal mucus. These results indicate that cAMP in nasal mucus can be an index of smell loss and that its secretion may be inhibited in smell loss. Thus, monitoring of cAMP in the nasal mucus can be a diagnostic tool for the treatment of diseases related to cAMP. Results also indicate that there was less significant difference between cGMP in nasal mucus in normal subjects or in patients with hyposmia.

TABLE 30

Comparison of cAMP and cGMP in human nasal mucus in normal subjects and in patients with smell loss (Hyposmia)

| | | cAMP | | cGMP | | PROTEIN |
| --- | --- | --- | --- | --- | --- | --- |
| | | pmol/ml | pmol/mg protein | pmol/ml | pmol/mg protein | mg/min |
| CONDITION NORMAL | (41) | $0.22 \pm 0.02^\dagger$ | $0.08 \pm 0.01$ | $0.25 \pm 0.04$ | $0.06 \pm 0.01$ | $3.37 \pm 0.19$ |
| MEN | (34) | $0.21 \pm 0.01$ | $0.05 \pm 0.01$ | $0.28 \pm 0.02$ | $0.04 \pm 0.004$ | $3.32 \pm 0.13$ |
| WOMEN | (7) | $0.23 \pm 0.06$ | $0.10 \pm 0.04$ | $0.24 \pm 0.13$ | $0.10 \pm 0.04$ | $3.59 \pm 1.02$ |
| PATIENTS | (146) | $0.14 \pm 0.02^d$ | $0.07 \pm 0.01$ | $0.20 \pm 0.02$ | $0.12 \pm 0.01$ | $2.48 \pm 0.08^b$ |
| MEN | (63) | $0.14 \pm 0.02^c$ | $0.07 \pm 0.02$ | $0.25 \pm 0.03$ | $0.12 \pm 0.02$ | $2.50 \pm 0.13^b$ |
| WOMEN | (83) | $0.15 \pm 0.02$ | $0.07 \pm 0.01$ | $0.17 \pm 0.02$ | $0.11 \pm 0.01$ | $2.46 \pm 0.11^c$ |

( )Subject number $^\dagger$Mean ± SEM $^b$p < 0.005 compared to normals $^c$p < 0.01 compared to normals $^d$p < 0.05 compared to normals

Example 31

Analysis of cAMP and cGMP Concentrations in Nasal Mucus of Patients

Table 31 illustrates detection and measurement of cAMP and cGMP secretion in nasal mucus in patients with graded severity of smell loss (anosmia<Type I hyposmia<Type II hyposmia from most severe to least severe). Data indicates that as degree of smell loss increased, levels of cAMP in nasal mucus decreased. These data confirm the relationship between cAMP secretion in nasal mucus and degree of smell loss. Results also indicate that there was less significant difference between cGMP in nasal mucus in normal subjects or in patients with hyposmia.

Example 32

Analysis of Nitric Oxide (NO) in Saliva and in Nasal Mucus

Table 32 illustrates detection and measurement of NO in human saliva and nasal mucus. NO was found to be present in both saliva and nasal mucus and its mean concentration in saliva were 21% lower in patients than in normal subjects whereas in nasal mucus mean levels were 25% lower in patients. Treatment which increases cAMP in nasal mucus and improves smell function may be mirrored by increases in nasal mucus NO. The detection of NO in nasal mucus provides a non invasive method of diagnosing various diseases related to human physiology and pathology.

TABLE 31 cAMP and cGMP concentrations in nasal mucus in patients with various degrees of smell loss

| PATIENTS | | TOTAL PROTEIN mg/ml | cAMP pmol/ml | cAMP PROTEIN pmol/mg | cGMP pmol/ml | cGMP PROTEIN pmol/mg |
| --- | --- | --- | --- | --- | --- | --- |
| ANOSMIA | (2) | 1.41 | 0.004 | 0.003 | 0.179 | 0.127 |
| HYPOSMIA | | | | | | |
| TYPE I | (17) | $2.61 \pm 0.29$ | $0.116 \pm 0.04^*$ | $0.034 \pm 0.01$ | $0.225 \pm 0.05$ | $0.101 \pm 0.02$ |
| TYPE II | (64) | $2.56 \pm 0.13$ | $0.193 \pm 0.03$ | $0.102 \pm 0.02^a$ | $0.189 \pm 0.03$ | $0.079 \pm 0.01$ |
| TYPE III | | | | | | |
| NORMAL SUBJECTS | (10) | $3.70 \pm 0.67$ | $0.225 \pm 0.67$ | $0.088 \pm 0.04$ | $0.356 \pm 0.13$ | $0.094 \pm 0.03$ |

( )Patient number

*Mean ± SEM $^a$p < 0.001 with respect to Type I hyposmia

TABLE 32

NO in saliva and nasal mucus in normal subjects and in patients with smell loss

| SUBJECTS | | SALIVA | | | NASAL MUCUS | | |
|---|---|---|---|---|---|---|---|
| | | NO µg/ml | PROTEIN mg/dl | NO/ PROTEIN | NO µg/ml | PROTEIN mg/dl | NO/ PROTEIN |
| NORMALS | (15) | $0.57 \pm 0.03$† | $2.6 \pm 0.1$ | $0.23 \pm 0.02$ | $0.48 \pm 0.08$ | $2.3 \pm 0.15$ | $0.22 \pm 0.05$ |
| PATIENTS | (34) | $0.45 \pm 0.06$ | $2.8 \pm 0.1$ | $0.18 \pm 0.03$ | $0.36 \pm 0.03$ | $2.0 \pm 0.08$ | $0.21 \pm 0.03$ |

( )Subject number
†MEAN ± SEM

Example 33

Analysis of Nitric Oxide (NO) in Nasal Mucus in Patients Before and after Theophylline Treatment Table 33 illustrates NO levels in nasal mucus in patients treated with Theophylline in various doses before and after drug treatment. NO levels in nasal mucus changed following the treatment of patients with smell loss. Results show treatment of patients with graded increasing doses of theophylline and measurement of both smell function and NO in nasal mucus in patients with hyposmia. Results indicated that prior to the treatment levels of NO in nasal mucus were lower than in normal subjects. After treatment with theophylline in graded doses there were increases in nasal mucus NO associated with graded increases in smell function. These data demonstrate that treatment with drugs that increase smell function to or toward normal, returns smell function to normal. These results also demonstrate the measurements of various substances in nasal mucus as an index of both human physiology and pathology of various diseases. Its continual measurement during treatment of these disorders helps in monitoring efficacy of therapy. The detection of NO in nasal mucus provides a non invasive method of diagnosing various diseases related to human physiology and pathology.

TABLE 33

NO in nasal mucus in patients with Theophylline in various doses before and after drug treatment

| SUBJECTS | | PRETREATMENT | | 200 mg | | 400 mg | | 600 mg | |
|---|---|---|---|---|---|---|---|---|---|
| | | NO µg/ml | Protein mg/dl | NO µg/ml | Protein mg/dl | NO µg/ml | Protein mg/dl | NO µg/ml | Protein mg/dl |
| Patients | (12) | $0.35 \pm 0.07$ | $1.6 \pm 0.3$ | $0.25 \pm 0.01$ | $1.7 \pm 0.3$ | $0.40 \pm 0.06$ | $2.1 \pm 0.10$ | $0.59 \pm 0.16$ | $1.9 \pm 0.15$ |
| Normal | | $0.61 \pm 0.20$ | | | | | | | |

( )Subject number

Example 34

Analysis of Insulin Like Growth Factor (IGF 1) in Human Saliva and Nasal Mucus

Table 34 illustrates detection and measurement of IGF 1 in human saliva and nasal mucus in 26 subjects. Results show that IGF 1 concentration in nasal mucus was significantly greater than in saliva. Results indicate that the measurement of nasal mucus IGF 1 can be used as an index of human physiology and pathology. The detection of IGF 1 in nasal mucus provides a non invasive method of diagnosing various diseases related to human physiology and pathology.

TABLE 34

IGF 1 in human saliva and nasal mucus

|  |  | SALIVA | | | NASAL MUCUS | | |
|---|---|---|---|---|---|---|---|
|  |  | IGF 1 µg/ml | PROTEIN mg/dl | IGF 1/ PROTEIN | IGF 1 µg/ml | PROTEIN mg/dl | IGF 1/ PROTEIN |
| SUBJECTS | (26) | $11.4 \pm 0.5^\dagger$ | $3.1 \pm 0.2$ | $4.6 \pm 0.4$ | $13.7 \pm 0.4^b$ | $2.2 \pm 0.2$ | $8.9 \pm 1.0^a$ |

( )Subject number
$^\dagger$MEAN ± SEM
With respect to saliva
$^b p < 0.005$
$^a p < 0.001$

Example 35

Analysis of TNFα, TNFR$_1$, and TNFR$_2$, in Nasal Mucus of Patients

Table 35 illustrates detection and measurement of TNFα, and soluble TNF receptors 1 and 2, moieties in the nasal mucus. TNFα, and soluble TNF receptors 1 and 2 increase in systems undergoing excessive apoptosis. Treatment with 600 mg theophylline restored smell function to or toward normal in these patients. There was a significant dose-response decrease in each moiety related to a stepwise increase in theophylline treatment associated and a stepwise improvement in olfactory acuity. These results suggest that pathological apoptosis of olfactory epithelial anatomy causes smell loss in patients with hyposmia; this process is reversed with theophylline therapy which restores smell function in these patients. These results illustrate biochemical parameters associated with return of smell function in patients treated with theophylline.

TABLE 35

TNFα, TNFR$_1$, TNFR$_2$, in nasal mucus in patients with hyposmia treated with Theophylline

| | Theophylline treatment (mg/l) | | | |
|---|---|---|---|---|
| PATIENTS | PRE | 200 | 400 | 600 |
| TNFα* (24) | $18.3 \pm 6.1^\dagger$ | $20.0 \pm 2.8$ | $12.1 \pm 2.1^d$ | $7.4 \pm 1.8^a$ |
| TNFR$_1$ (19) | $2,353 \pm 718$ | $3,148 \pm 663$ | $1,146 \pm 220^b$ | $1,220 \pm 286^{ab}$ |
| TNFR$_2$ (18) | $1,747 \pm 535$ | $1,952 \pm 339$ | $949 \pm 180^c$ | $916 \pm 344$ |

*in pg/ml
( ) Subject Number
$^\dagger$Mean ± SEM
$^a p < 0.001$ with respect to 200 mg.
$^b p < 0.001$ with respect to 200 mg.
$^c p < 0.025$ with respect to 200 mg.
$^d p < 0.05$ with respect to 200 mg.

Example 36

Analysis of TNFα in Nasal Mucus in Patients Before and after Treatment with Theophylline These studies were extended to reveal levels of TNFα in nasal mucus of patients with graded loss of smell following treatment with theophylline (Table 36). Smell loss was graded such that loss was greatest in Type I hyposmia, less in Type II and still less in Type III (I>II>III). Pretreatment levels of TNFα were significantly higher in patients with Type I hyposmia than in Type II hyposmia consistent with their greater degree of smell loss. Following treatment which was effective in restoring smell function toward normal, levels of TNFα decreased in each patient group consistent with each increased dose of theophylline which generated a dose dependent increase in smell function—as theophylline dose increased, smell function increased and TNFα levels decreased. In Type I hyposmia TNFα decreased 40% after treatment with 400 mg theophylline and 57% after treatment 600 mg. In Type II hyposmia TNFα decreased 11% after treatment with 600 mg theophylline.

TABLE 36

TNFα in nasal mucus in patients with various types of hyposmia treated with theophylline

| | Theophylline treatment* | | | |
|---|---|---|---|---|
| HYPOSMIA TYPE | PRE | 200 | 400 | 600 |
| I (8) | $26.0 \pm 6.5^{tb}$ | — | 15.6 | $11.2 \pm 4.4$ |
| II (13) | $5.3 \pm 1.0$ | $14.9 \pm 2.5$ | $11.5 \pm 3.2$ | $4.3 \pm 0.8^a$ |
| III (3) | | — | | $1.2 \pm 0.7^{bc}$ |

*in mg orally daily
( ) Subject Number
$^t$Mean ± SEM
$^a p < 0.001$ with respect to 200 mg
$^b p < 0.001$ with respect to Type I (600 mg)
$^c p < 0.01$ with respect to Type II (600 mg)
$^d p < 0.001$ with respect to Type II, pre treatment

Example 37

Analysis of TNFR 1 in Nasal Mucus in Patients Before and after Treatment with Theophylline TNF Receptor 1 (TNFR1) exhibited similar results in nasal mucus in patients with smell loss after treatment with theophylline (Table 37). With increased smell loss pre treatment TNFR 1 levels were increased in nasal mucus in patients with Type I hyposmia (whose smell loss was increased over that of patients with Type II hyposmia). After theophylline treatment, as a dose of drug increased, TNFR 1 levels decreased in Type I associated with increases in smell function. Levels of TNFR 1 at 600 mg theophylline were systematically decreased in relation to degree of smell loss. The greater was the smell loss, the higher was the level of TNFR 1.

TABLE 37

TNFR 1 in nasal mucus in patients with various types of hyposmia treated with theophylline

| HYPOSMIA | Theophylline treatment* | | | |
|---|---|---|---|---|
| TYPE | PRE | 200 | 400 | 600 |
| I (7) | $4,626 \pm 1,647^{tb}$ | $6,521 \pm 1,304^c$ | 1,498 | $1,832 \pm 704^a$ |
| II (10) | $837 \pm 60$ | $1,462 \pm 371$ | $1,087 \pm 335$ | $862 \pm 335$ |
| III (2) | — | — | — | $585 \pm 335$ |

*in mg orally daily
( ) Subject Number
$^t$Mean ± SEM
$^a$ $p < 0.005$ with respect to 200 mg
$^b$ $p < 0.02$ with respect to Type II pre treatment
$^c$ $p < 0.01$ with respect to Type II or 200 mg

TABLE 38

TNFR 2 in nasal mucus in patients with various types of hyposmia treated with theophylline

| HYPOSMIA | Theophylline treatment* | | | |
|---|---|---|---|---|
| TYPE | PRE | 200 | 400 | 600 |
| I (7) | $2,718 \pm 1,125^t$ | $3,100 \pm 1,184$ | | $1,491 \pm 1,102$ |
| II (10) | $1,145 \pm 625$ | $1,378 \pm 480$ | $1,014 \pm 272$ | $553 \pm 158$ |
| III (2) | — | — | — | $436 \pm 443$ |

*in mg orally daily
( ) Subject Number
$^t$Mean ± SEM
$^a$ $p < 0.001$ with respect to 200 mg
$^b$ $p < 0.001$ with respect to Type I (600 mg)
$^c$ $p < 0.01$ with respect to Type II (600 mg)

Example 39

Analysis of Endoglin in Human Plasma, Urine, Saliva and Nasal Mucus

Table 39 illustrates detection and measurement of Endoglin in the nasal mucus. Results indicate that the measurement of nasal mucus Endoglin can be used as an index of human physiology and pathology. The detection of Endoglin in nasal mucus provides a non invasive method of diagnosing various diseases related to human physiology and pathology.

TABLE 39

Endoglin in human plasma, urine, saliva and nasal mucus

| | PLASMA | | | URINE | SALIVA | NASAL MUCUS | | |
|---|---|---|---|---|---|---|---|---|
| SUBJECTS | ENDOGLIN mg/ml | PROTEIN mg/dl | ENDOGLIN PROTEIN | ENDOGLIN mg/ml | ENDOGLIN mg/ml | ENDOGLIN mg/ml | PROTEIN mg/dl | ENDOGLIN PROTEIN |
| (33) | $2.7 \pm 0.1^{ta}$ | $7.1 \pm 0.1$ | $0.38 \pm 0.1$ | 0 | 0 | $0.2 \pm 0.1$ | $2.8 \pm 0.1$ | $0.07 \pm 0.01$ |

( )Subject number
$^t$MEAN ± SEM
$^a$ $p < 0.001$ with respect to nasal mucus

Example 38

Analysis of TNFR2 in Nasal Mucus in Patients Before and after Treatment with Theophylline TNR Receptor 2 (TNFR 2) in nasal mucus exhibited similar results (Table 38). Pretreatment with theophylline in patients with the most severe smell loss (Type I hyposmia) exhibited higher TNFR 2 levels in nasal mucus than did patients with less severe smell loss (Type I hyposmia). With a dose dependent increase of theophylline treatment levels of TNFR 2 in nasal mucus decreased consistent with a dose dependent increase in smell function. Levels of TNFR 2 in patients with Type I and Type II hyposmia decreased almost 50% on 600 mg theophylline consistent with their greatest return of smell function. At this highest level of theophylline levels of TNFR 2 were decreased in relationship to the decrease in smell function—TNFR 2, Type I>Type II>Type III; smell loss, Type I>Type II>Type III.

Example 40

Increased Carbonic Anhydrase (CA) I, II and VI, Zinc and Copper after rTCMS

Ninety three patients, aged 18-85 y (52±2 y, Mean±SEM), 49 men, aged 29-74 y (51±3 y) and 44 women, aged 20-85 y (53±3 y) with hyposmia, hypogeusia, and subsequent phantageusia (distortion of taste independent of any oral stimulus) and/or phantosmia (distortion of smell independent of any environmental odor) were studied before and after rTCMS in a single blind placebo controlled fixed sequence clinical trial.

Patient symptoms persisted for 0.4-30 y (6.9±1.5 y) prior to rTCMS. Physical examination of head and neck including examination of oral and nasal cavities (the nose examined by anterior rhinoscopy with use of vasoconstrictor agents) was within normal limits. Neither neurological nor psychiatric abnormalities other than taste and/or smell dysfunction was present in any patient. Anatomical magnetic resonance imaging (MRI) of brain and electroencephalographic (EEG) studies in all patients were within normal limits.

rTCMS was performed with a Cadwell magnetic pulse stimulator (Kennewick, Wash.) monitored with a TECA TD20 (Pleasantville, N.Y.) wave form generator, as described in Cicinelli, P., et al., *Eletroenceph. Clin. Neurophys,* 1997, 105:438-450; Henkin, Robert, et al., *FASEB J.,* 2002, 16:A878; Henkin, R. I., *Encyclopedia of Neuroscience* (3rd Ed), Adelman, G. Smith, B H eds, Birkhauser, Boston, 2003, and; Moharram, R., et al., *FASEB J.,* 2004, 18:A201, all incorporated by reference in their entirety herein.

Stimulation was applied in a fixed manner to four skull locations (left and right temporoparietal, occipital, frontal of patients). Stimulus frequency was 1 pulse given per 1-3 sec for 30-90 sec with 20 pulses given at each location. Repeat stimulation was performed in all patients in whom increased sensory acuity and/or decreased sensory distortions occurred; repetition continued (two-six applications) until no further increase in sensory acuity and/or decrease in sensory distortions occurred.

One hour before and one to two hr after completion of rTCMS, venous blood and parotid saliva were collected. Whole venous blood was placed into zinc free tubes containing 100 µl of zinc free heparin, on ice, centrifuged at 3000 rpm at 4° C., plasma removed and stored at −20° C. until assayed. Erythrocytes were washed and treated as described in Agarwal, R. P., et al., *Bio. Tr. Elem. Res.,* 1985, 7:199-208, incorporated by reference in its entirety herein. Parotid saliva was collected in four plastic tubes on ice using a modified Lashley cup applied to Stensen's duct with maximal stimulation using reconstituted lemon juice applied to the lingual surface as described in, Henkin, R. I., et al., *Proc. Nat. Acad. Sci. USA,* 1975, 72:488-492 and Henkin, R. I., et al., *Amer. J. Med. Sci.,* 1976, 272:285-299, both incorporated by reference in their entirety herein. The first three tubes were collected at two min intervals, the fourth tube until approximately eight ml was collected. For convenience only results of saliva from the fourth tube will be presented. Five hundred µl of saliva from the fourth tube was placed in dry ice immediately after collection and stored at −60° C. until measurements by SELDI-TOF mass analysis was performed.

Zinc and copper were measured in each tissue by atomic absorption spectrophotometry (AAS) by using a double beam ThermoJarrell Ash video 22 (Franklin, Mass.) AAS modified by the Maxwell Instrument Company (Salisbury, N.C.), the methods previously described in, Henkin, R. I., et al., *Amer. J. Med. Sci,* 1999, 318, 380-391; Agarwal, R. P., et al., *Bio. Tr. Elem. Res.,* 1985, 7:199-208; Henkin, R. I., et al., *Amer. J. Med. Sci.,* 1976, 272:285-299, and; Meret, S., et al., *Clin. Chem.,* 1971, 17:369-373, all incorporated by reference in their entirety herein. Saliva protein was determined by measurement of total peptide content by use of absorbance at A215-A225 (called 4215) and the extinction coefficient. CA activity was measured by a modification of the method of Richli, E. E., et al., *J. Biol. Chem.,* 1964, 239:1065-1078, incorporated herein by reference in its entirety. Saliva samples stored at −60° C. were thawed and 1 µl directly spotted on an H4 Protein Chip array (pre washed with 0.1% TFA in 50% aqueous acetonitrile) and their protein profile examined on a Ciphergen (Fremont, Calif.) PBS IIc mass analyzer.

Samples were first incubated in a humid chamber for 5-10 minutes at room temperature, then washed with 5% aqueous acetonitrile, dried and 1 µl matrix added (sinapinic acid in 0.1% TFA, 50% aqueous acetonitrile). Samples were allowed to dry again and subjected to SELDI-TOF analysis on the PBS IIc. Protein peaks were characterized by their apparent molecular weight based on their mass/charge ratio (m/z).

Following initial observation of biochemical changes after rTCMS subsequent measurements in all biological fluids were performed in a blinded manner; all samples were coded and results uncoded only after all analyses were completed. Mean±SEM for each parameter was determined for each condition pre and post rTCMS. Differences between each condition were calculated for each parameter and significance of differences determined by parametric (differences between undifferentiated means, paired t tests, $X^2$) and non parametric (sign test) statistics.

Results:

After rTCMS mean CA VI activity and salivary zinc and copper concentrations increased significantly as did mean CA I, II activity and plasma copper concentrations (Table 40). Significant increases in both CA I, II and CA VI activity were also measured using paired comparisons (p<0.01 Student t test) and the sign test (p<0.05, Student t test) (data not shown). These latter data are reflected in results shown in Table 41 in which changes pre and post rTCMS are shown. Increased CA VI was measured in 87% of patients with changes varying from −5% to +153% (mean change, +17%) (Table 41); compared to chance changes of this magnitude would occur <5 times in 1000 ($X^2$). Increased CA I, II was measured in 93% of patients with changes varying from −2% to +56% (mean change, +11%) (Table 41); compared to chance changes of this magnitude would also occur <1 time in 1000 ($X^2$). Increased plasma and erythrocyte zinc and copper concentrations were measured in 91-93% of patients (Table 41); compared to chance changes of this magnitude would also occur <1 time in 1000 ($X^2$).

TABLE 40

Changes in plasma, erythrocyte and saliva CA I, II and VI, zinc and copper before (pre) and after (post) rTCMS in 93 patients rTCMS

| CONDITION | PRE | POST |
| --- | --- | --- |
| PLASMA | | |
| Zn (µg/dl) | 85 ± 2* | 88 ± 2 |
| Cu (µg/dl) | 101 ± 2 | 109 ± 3[a] |
| ERYTHROCYTES | | |
| Zn (µg/gHb) | 38.0 ± 0.5 | 39.7 ± 0.5[b] |
| Cu (µg/gHb) | 2.1 ± 0.04 | 2.2 ± 0.05 |
| CA I, II (µg/g protein) | 3.12 ± 0.06 | 3.45 ± 0.06[d] |
| SALIVA | | |
| Zn (µg/L) | 103 ± 5 | 121 ± 5[b] |
| Cu (µg/L) | 13 ± 1 | 22 ± 3[c] |
| CA VI (µg/g protein) | 0.153 ± 0.009 | 0.197 ± 0.008[d] |

*Mean ± SEM
CA, carbonic anhydrase
Compared to pre rTCMS
[a] p < 0.05
[b] p < 0.025
[c] p < 0.01
[d] p < 0.001

TABLE 41

Changes in plasma, erythrocyte and saliva carbonic anhydrase I, II and VI, zinc and copper before (pre) and after repetitive transcranial magnetic stimulations (rtcms) in patients with decreased sensory acuity and presence of sensory distortions
rTCMS
PRE vs. POST

| CONDITION | NUMBER | | | INCREASED % |
|---|---|---|---|---|
| | INCREASED | DECREASED | UNCHANGED | |
| PLASMA | | | | |
| Zn (µg/dl) | 61 | 6 | 0 | 91 |
| Cu (µg/dl) | 62 | 5 | 0 | 93 |
| ERYTHROCYTES | | | | |
| Zn (µg/gHb) | 66 | 1 | 0 | 99 |
| Cu (µg/gHb) | 62 | 4 | 1 | 93 |
| CA I, II (µg/g protein) | 62 | 4 | 1 | 93 |
| SALIVA | | | | |
| Zn (µg/L) | 49 | 18 | 0 | 73 |
| Cu ((µg/L) | 51 | 16 | 0 | 76 |
| CA VI (µg/g protein) | 60 | 5 | 2 | 90 |

Figure 10:
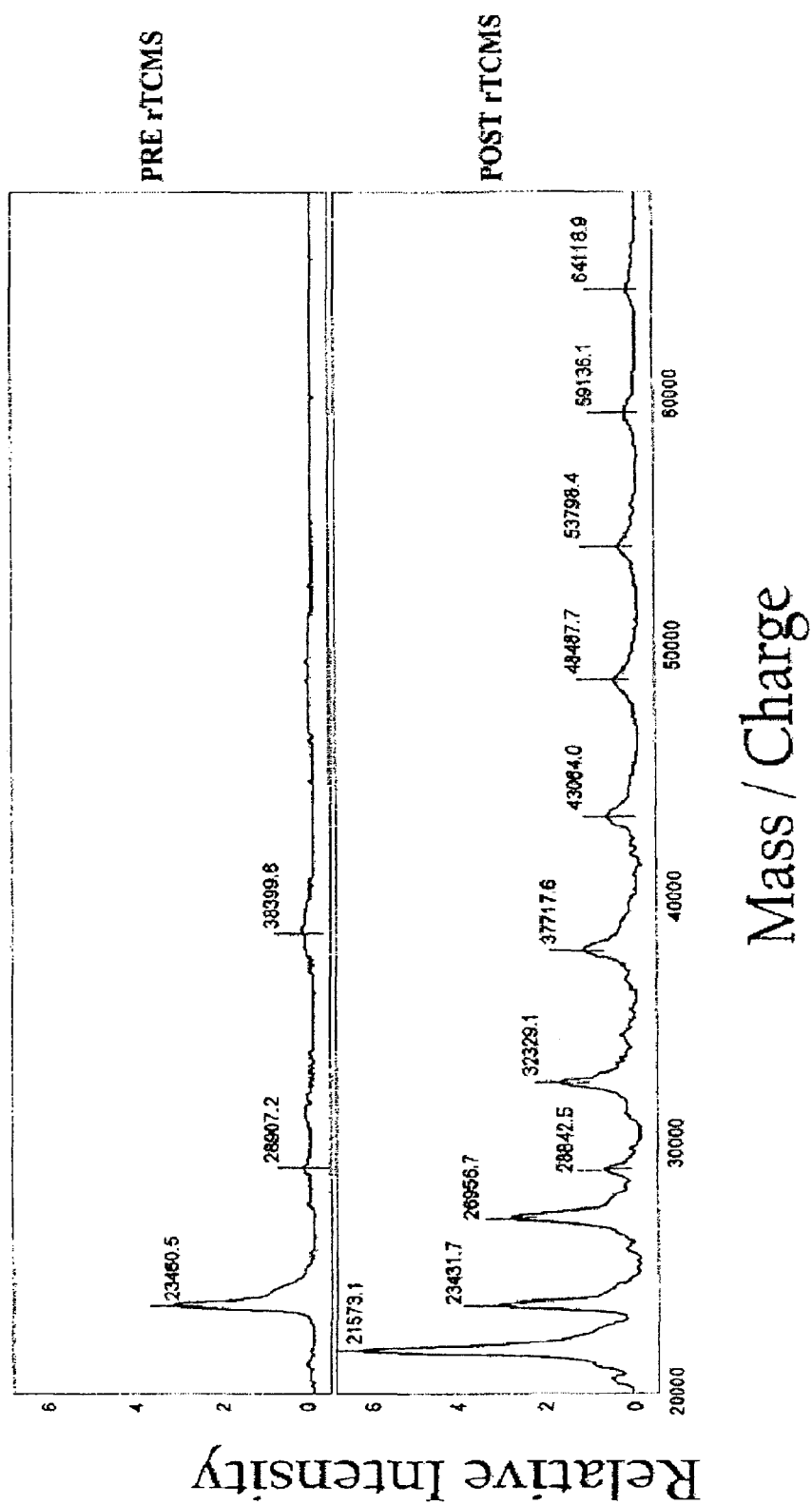
FIG. 10 depicts mass spectroscopic analysis of parotid saliva of patients before and after treatment with rTCMS.

SELDI-TOF mass spectrometry revealed a peak at m/z 21.5K in the post rTCMS spectra which was absent in the pre rTCMS spectra (FIG. 10). Also present in the post rTCMS spectra was a repetitive protein pattern separated by intervals of approximately 5K m/z (FIG. 10). Similar patterns were observed in about ⅓ of patients studied.

Thus, the present study illustrates that several salivary proteins can be induced after rTCMS (FIG. 10). Increased enzyme activities and zinc and copper concentrations usually persisted two-four wk after rTCMS; however, over time there was a slow, gradual decrease in enzyme activities and in plasma, erythrocyte and saliva zinc and copper concentrations as well as a loss of sensory acuity and subsequent return of sensory distortions.

This study demonstrates that biochemical changes may occur after rTCMS. Since changes in taste and smell function occur in several neurological disorders these results may also relate to other conditions such as epilepsy, Parkinsonism, Alzheimer disease, head injury, and motor neuron disease in which rTCMS can be an effective therapeutic agent.

Example 41

Recovery of Taste and Smell Function Following rTCMS

Seventeen right handed Caucasian patients, five men, aged 40-74 y (58±7 y, X±SEM), 12 women, aged 30-76 y (51±5 y) were studied. Each had mild to severe persistent hyposmia and hypogeusia as well as mild to severe persistent birhinal phantosmia and/or global oral phantageusia; the sensory distortions were profound enough to interfere with normal life pursuits. Acuity loss persisted for 6 mo to 30 y (4.1±2 y) and sensory distortions persisted for 3 mo to 30 y (3.7±2 y) prior to clinic visit. Etiologies which initiated their symptoms were head injury (4 patients), post influenza-like infection (PIHH, 7 patients), idiopathic causes (4 patients) and drug reactions (2 patients). Each of the 17 patients who presented with these symptoms was treated with rTCMS.

None had any neurological symptom other than loss of sensory acuity and presence of sensory distortions. None had any psychiatric symptom other than some depression associated with persistence of these cognitive impairments. Symptoms were unrelieved by any prior treatment with multiple agents including antiepileptics, anxiolytics, antidepressants, trace metals, vitamins and a variety of alternative treatment modalities including herbal remedies, acupuncture, chiropractic techniques and hypnosis. Physical examination of each patient, including examination of the head and neck and general neurological examination, was within normal limits. Both anatomical brain MRI and electroencephalograms were within normal limits in each patient.

Measurement Techniques:

A battery of tests measuring taste and smell acuity and character and degree of sensory distortions were administered to each patient. Taste and smell acuity were determined by standard three stimuli forced choice staircase techniques (Henkin R. I., Amer. J. Med. Sci. 1976, 272:285-299, incorporated herein by reference in its entirety) by which detection (DT) and recognition (RT) thresholds and magnitude estimation (ME) for four tastants [NaCl (salt), sucrose (sweet), HCl (sour) and urea (bitter)] and four odorants [pyridine (dead fish), nitrobenzene (bitter almond), thiophene (old motor oil) and amyl acetate (banana oil)] were determined, and reference values established for a large number of normal subjects. Results for DT and RT, in mmol/L and M/L for tastants and odorants, respectively, were converted into bottle units (BU) and compared to previously established standards. Magnitude estimation (ME) was determined, calculated in % for each stimulus and compared to previously described standards in Henkin et al. *Otolaryngology,* 1993, vol. 2, p1-86 and Henkin et al. *Drug safety,* 11:310-377, 1994, incorporated herein by reference in its entirety.

Sensory distortions were graded daily in intensity, duration and frequency using a written record on a 0-100 scale for 3 d-4-wk prior to rTCMS; 0 reflected total absence of sensory distortions, 100 reflected the digitized composite of the most intense distortion experienced over the entire day. Records were reviewed prior to the study to insure adequate understanding of symptom grading. The entire battery of cognitive measurements was obtained at the initial patient visit and repeated immediately prior to and after each rTCMS treatment. This battery was also repeated at variable intervals (1 day, 2-4-wk, 6-46 mo) after each rTCMS treatment. Each test battery was performed independent of knowledge of any prior test result.

Treatment Protocol:

rTCMS was performed with a Cadwell magnetic pulse stimulator (Kennewick, Wash.) monitored by a TECA TD20 (Pleasantville, N.Y.) wave form generator. Stimulation was applied by a single open quadrangular 12×12 cm coil. Three sequential stimulation protocols were used. The first two were considered placebo or sham trials.

For the initial sham trial, 20 stimuli at intervals of 1-3 sec were applied sequentially at the lateral acromial process of the clavicle (near Erb's point) (a) to the anterior right shoulder, then (b) anterior left shoulder at 20-30% maximal output [20-30% of 1.5 T or ~0.2-0.4 T (since stimulus delivery was non-linear)] and then (c) to the back of the mid neck region (at the level of $C_{5-8}$ at 30-40% maximal output or ~0.4-0.8 T); mild muscle group flexion of arm and hand muscles (shoulder stimulation) and neck, strap and facial muscles (neck) followed each stimulation and was visually monitored.

For the second sham trial, 20 stimuli at intervals of 1-3 sec were applied sequentially to four skull regions (left temporoparietal, occipital, right temporoparietal, frontal) at 20% maximal output; this was considered subthreshold stimulation since no peripheral muscle responses occurred.

For the treatment trial, 20 stimuli at intervals of 1-3 sec were applied at 40-55% maximal output (~0.8-LIT) to each skull location as in the second sham trial noted above. Muscle responses to this latter stimulation were present and monitored by visual observation (e.g., right/left thenar and/or phalangeal flexion with left/right temporoparietal stimulation, respectively).

After each 20 stimuli of sham or treatment stimulation at each anatomical location, olfactory response to presentation of a single odor (one concentration of an odorant whose DT, RT and ME were previously determined) and/or changes in intensity and character of phantageusia and/or phantosmia (previously determined) was recorded. If any change in olfactory acuity or in sensory distortion occurred after any stimulation, stimulation at that location at that same intensity was repeated two-six times until no further change occurred.

Outcome Measures:

Mean±SEM of changes in taste and smell acuity (DT, RT, ME) and in intensity of sensory distortions before and after each rTCMS treatment were calculated and significance of differences determined by Student's t tests. Differences were also calculated using paired t tests with significance of differences pre and post rTCMS determined by Student's t test.

Results: Pre rTCMS I

Taste:

Mean DTs and RTs for all tastants were above normal (i.e. acuity was decreased). Mean MEs for all tastants were below normal (i.e. acuity was decreased) (Table 42). Mean DT and RT for all tastants except DT for HCl were significantly above normal and mean MEs for all tastants were significantly below normal.

Smell:

Mean DTs and RTs for all odorants were above normal (i.e. acuity was decreased) and mean MEs for all odorants were below normal (i.e. acuity was decreased) (Table 42). Mean DT and RT for all odorants (except DTs for pyridine, thiophene and amyl acetate) and mean MEs of all odorants were significantly above normal (Table 42).

Sensory Distortions:

Phantageusia intensity was 82±7%. Phantosmia intensity was 72±14% (Table 43). There were no gender differences in either phantageusia or phantosmia intensity (Table 43).

Results: Post rTCMS I

Placebo or Sham Stimulation (0.2-0.4 T):

No subjective or objective changes in either taste and/or smell acuity or in character or intensity of sensory distortions occurred in any patient following stimulation of shoulders or neck or in any skull location.

Treatment Stimulation (0.8-1.1 T):

Taste:

Mean DTs and RTs for all tastants decreased (i.e., acuity increased) and mean MEs for all tastants increased (i.e. acuity increased) (Table 42). Mean DT and RT returned to normal levels for NaCl, sucrose and HCl as did DT for urea and ME for all tastants (Table 42). Only mean RT for urea did not return to normal although it was significantly lower than before treatment (Table 42).

Smell:

Mean DTs and RTs for all odorants decreased (i.e., acuity increased) and mean MEs for all odorants increased (i.e., acuity increased) (Table 42). Mean DT and RT for pyridine, nitrobenzene and thiophene and mean DT for amyl acetate returned to or below normal levels after treatment (Table 42). Only mean RT for amyl acetate did not return to normal although it was significantly below values obtained before this treatment. Mean ME for all odorants also returned to normal levels.

Sensory Distortions:

Mean phantageusia and phantosmia intensity decreased significantly (Table 43). In each man phantosmia disappeared.

Response Summary:

No changes in taste or smell acuity or in sensory distortion intensity occurred in two patients immediately after treatment stimulation [(one with head injury, one with PIHH, both women, data included in Tables 42 and 43)]. These two patients were labeled non-responders. Reports of no change in sensory distortion intensity and no change in repeat acuity testing occurred in these two patients 2-7 d after treatment. No changes were reported 4 wk after rTCMS I and no further data about these patients were obtained.

Taste and smell acuity returned to normal levels for all tastants and odorants and all sensory distortions completely disappeared in two patients within one hr after rTCMS I [(one with head injury (one woman) one with PIHH (one man), data included in Tables 42 and 43)]. These two patients were labeled responders. Repeat testing 2-7 d after rTCMS I demonstrated normal sensory acuity and no sensory distortions were reported (data not shown). Reports of normal sensory acuity and absence of any sensory distortions were received for as long as these patients were followed (46 mo).

In the remaining 13 patients sensory acuity improved (Table 42) and sensory distortions diminished (Table 43) one hour after stimulation (Table 43). These 13 patients were also labeled responders. Symptom improvement occurred (vs) in all responders when the field was applied at only one skull location. Seven patients reported improvement after left temporoparietal stimulation, four (27%) after right temporoparietal stimulation, three (20%) after frontal stimulation and one (7%) after occipital stimulation. There was no improvement in the non-responders no matter where the field was applied.

Later Post rTCMS I

Four wk-2 mo after rTCMS I, repeat testing of taste and smell acuity and measurement of sensory distortion intensity indicated that cognitive impairments had returned in 13 of the 15 responders (vs). A second trial of rTCMS (rTCMS II) was instituted in these patients.

Pre rTCMS II

Immediately prior to rTCMS II, the entire battery of sensory tests and measurement of sensory distortion intensity previously measured were repeated (Table 44).

Taste:

Compared to immediately post rTCMS I, mean DTs and RTs for all tastants (except DT for HCl which did not change) increased (i.e., acuity decreased) and mean MEs for all tastants decreased (i.e., acuity decreased) (cf Tables 44, 42).

Smell:

Compared to immediately post rTCMS I, mean DTs and RTs for all odorants (except RT for thiophene which was lower than post rTCMS I) increased (i.e., acuity decreased) and mean MEs for all odorants decreased (i.e., acuity decreased), (except for thiophene which was higher (cf Tables 44, 42). However, mean MEs were all higher than pre rTCMS I indicating that some improvement after rTCMS I was retained.

Sensory Distortions:

Compared to immediately after rTCMS I, mean estimates of phantageusia intensity increased but were significantly less than intensities measured prior to rTCMS I (cf Tables 45, 43, pre rTCMS I, 82±7, later post rTCMS I, 39±20, p<0.05 t test, p<0.02 paired t test). Similarly mean estimates of phantageusia intensity also increased but were less than pre rTCMS I (cf Tables 45, 43, pre rTCMS I, 72±14, later post rTCMS I, 47±8, p>0.05 t test, p<0.05 paired t test). Similar changes also occurred in phantosmia (cf Tables 45, 43).

Response Summary:

These results suggest that the improvement in cognitive impairments which occurred immediately after rTCMS I persisted to some extent but these patients "escaped" from this improvement with a return of cognitive impairments. A second course of rTCMS was instituted.

rTCMS II

Placebo or Sham Stimulation (0.2-0.4 T):

No subjective or objective changes in either taste and/or smell acuity or in character or intensity of sensory distortions occurred in any patient following stimulation of shoulders, neck or in any skull location.

Treatment Stimulation (0.8-1.1 T):

Taste:

Mean DTs and RTs for all tastants decreased (i.e., acuity increased) and mean MEs for all tastants increased (i.e., acuity increased) (Table 44) as after rTCMS I (Table 42). There were significant decreases in DTs for NaCl and urea and RTs for HCl and urea. Mean MEs for all tastants were not significantly different from normal (Table 44). DT for NaCl was significantly lower, (i.e., relative increased acuity) than normal as was DT for urea.

Smell:

Mean DTs and RTs for all odorants decreased (i.e., acuity increased) and mean MEs for all odorants increased (i.e., acuity increased) (Table 44) as after rTCMS I (Table 42). There were no significant differences in mean DTs, RTs or MEs for any odorant with respect to normal. DTs for nitrobenzene and thiophene and RTs for pyridine and nitrobenzene were lower than normal (i.e., relative increased acuity) and MEs for pyridine, nitrobenzene and thiophene were higher than normal (i.e., relative increased acuity).

Sensory Distortions:

Significant decreases occurred in phantageusia and phantosmia (Table 45) as after rTCMS I (Table 43). Phantosmia completely disappeared after treatment in all patients including all men and women, not just in men as after rTCMS I (Table 43). Phantageusia disappeared in 10 patients, improved by 50% in one and only slightly, if at all, in two. After rTCMS II both mean phantageusia and phantosmia intensity decreased to levels below those measured later post rTCMS I (cf, Tables 43, 45).

In these 13 patients rTCMS II was effective in initiating improvement again only at the same locus at which initial improvement occurred after rTCMS I.

Response Summary:

After rTCMS II improvement lasted longer than after rTCMS I, lasting wk-mo. In seven of these 13 (54%) (one with head injury, four with PIHH, two idiopathic) return of sensory acuity to normal and total cessation of sensory distortions persisted for as long as measurements were made (30 mo). In the remaining six patients (one with head injury, one with PIHH, the two with idiopathic causes, the two with drug reactions) symptoms of cognitive impairment returned after one-five mo but acuity was less impaired and sensory distortions were less intense than prior to rTCMS II (as in pre rTCMS I and II).

These six patients who "escaped" from rTCMS II were again treated with rTCMS (rTCMS III) as in rTCMS I and II. This therapy was again effective in improving cognitive impairments but again only at the same locus that initiated improvement after prior stimulation (data not shown). All sensory acuity returned to normal levels and all sensory distortions disappeared in these six patients for as long as they were followed (6-36 mos).

The results indicate that rTCMS was efficacious in improving taste and/or smell acuity and in inhibiting phantosmia and phantageusia in most patients who exhibited these symptoms. Improvement occurred after rTCMS at one brain region. However, 13 of the 15 who initially responded exhibited a recurrence of their symptomatology. With recurrent symptomatology repeat rTCMS was effective again in improving symptoms but only after application at the same site at which initial improvement occurred, mainly the left temporoparietal region, a locus contralateral to patient handedness. This result indicates enhanced cognitive processing following rTCMS in one brain locus, mainly left prefrontal cortex. Repeated stimulation in patients at this effective locus prolonged improvement in cognitive function. TCMS can be applied in many different paradigms including use of single or repeated pulses, short or prolonged applications, varied wave forms, application intensity and a multiplicity of other parameters. The results of this experiment indicate that rTCMS improved sensory acuity and decreased sensory distortions in patients with these cognitive impairments.

TABLE 42

Changes in taste and smell acuity in 17 patients with hypogeusia, hyposmia, phantosmia and/or phantageusia pre and post rTCMS I compared to normal responses

| TASTANT | | | | | | | | | | | | |
|---|---|---|---|---|---|---|---|---|---|---|---|
| NaCl | | | SUCROSE | | | HCl | | | UREA | | |
| DT | RT | ME | DT | RT | ME | DT | RT | ME | DT | RT | ME |
| PRE | | | | | | | | | | | |
| $5.7 \pm 0.7^{\dagger a}$ | $6.3 \pm 0.9^b$ | $26 \pm 18^{d\ddagger}$ | $4.9 \pm 0.6^c$ | $5.2 \pm 0.6^a$ | $29 \pm 12^c$ | $5.3 \pm 0.9$ | $6.8 \pm 0.8^a$ | $27 \pm 6^a$ | $6.8 \pm 1.4^e$ | $9.0 \pm 1.0^a$ | $30 \pm 9^b$ |
| POST | | | | | | | | | | | |
| $3.2 \pm 0.0^g$ | $3.6 \pm 0.3^{b*}$ | $35 \pm 22$ | $3.6 \pm 0.4$ | $3.9 \pm 0.3$ | $46 \pm 12$ | $4.1 \pm 0.7$ | $4.3 \pm 0.6^j$ | $57 \pm 7^k$ | $5.0 \pm 1.0$ | $5.7 \pm 0.6^h$ | $53 \pm 8$ |
| NORMALS | | | | | | | | | | | |
| $3.3 \pm 0.3$ | $3.4 \pm 0.2$ | $68 \pm 4$ | $3.3 \pm 0.2$ | $3.4 \pm 0.2$ | $60 \pm 4$ | $3.4 \pm 0.4$ | $3.5 \pm 0.4$ | $66 \pm 4$ | $3.6 \pm 0.4$ | $3.7 \pm 0.4$ | $68 \pm 4$ |
| ODORANT | | | | | | | | | | | |
| PYRIDINE | | | NITROBENZENE | | | THIOPHENE | | | AMYL ACETATE | | |
| DT | RT | ME | DT | RT | ME | DT | RT | ME | DT | RT | ME |
| PRE | | | | | | | | | | | |
| $4.0 \pm 0.9^\dagger$ | $8.5 \pm 0.7^c$ | $35 \pm 13^{e\ddagger}$ | $6.4 \pm 0.7^b$ | $9.4 \pm 0.4^a$ | $21 \pm 7^b$ | $3.8 \pm 0.8$ | $7.4 \pm 1.0^a$ | $30 \pm 7^b$ | $4.3 \pm 1.1$ | $8.9 \pm 1.8^a$ | $24 \pm 7^a$ |
| POST | | | | | | | | | | | |
| $1.9 \pm 0.5^{ah}$ | $4.4 \pm 0.9^f$ | $67 \pm 11$ | $3.2 \pm 0.8^g$ | $6.2 \pm 1.0^g$ | $42 \pm 8$ | $1.9 \pm 0.3^i$ | $5.1 \pm 0.9$ | $45 \pm 7^h$ | $1.4 \pm 0.0^{ch}$ | $5.2 \pm 0.9^g$ | $44 \pm 6^f$ |
| NORMALS | | | | | | | | | | | |
| $3.7 \pm 0.3$ | $6.0 \pm 0.7$ | $66 \pm 5$ | $3.6 \pm 0.4$ | $6.0 \pm 0.6$ | $52 \pm 6$ | $3.2 \pm 0.6$ | $3.3 \pm 0.5$ | $69 \pm 6$ | $3.1 \pm 0.5$ | $3.3 \pm 0.6$ | $53 \pm 5$ |

DT, detection threshold (in BU), RT, recognition threshold (in BU), ME, magnitude estimation (in %)
†MEAN ± SEM (in BU)
‡MEAN ± SEM (in %)
*All significance determined by Student's t test
Normals are 150 normal volunteer
Compared to normals
[a] p < 0.001
[b] p < 0.005
[b*] p < 0.01
[c] p < 0.02
[d] p < 0.025
[e] p < 0.05
Compared to pre rTCMS I
[f] p < 0.001
[g] p < 0.005
[h] p < 0.01
[i] p < 0.025
[j] p < 0.02
[k] p < 0.05

TABLE 43

Changes in phantageusia and phantosmia in 17 patients with hyposmia, hypogeusia, phantosmia and/or phantageusia pre and post rTCMS I

| | PHANTAGEUSIA | | PHANTOSMIA | |
|---|---|---|---|---|
| PATIENTS | PRE | POST | PRE | POST |
| TOTAL (17) | $82 \pm 7^\dagger$ | $21 \pm 7^a$ | $72 \pm 14$ | $22 \pm 12^c$ |
| MEN (5) | $71 \pm 15$ | $20 \pm 15^d$ | $70 \pm 20$ | $0^b$ |
| WOMEN (12) | $85 \pm 6$ | $22 \pm 9^a$ | $74 \pm 18$ | $33 \pm 17$ |

( ) Patient Number
†MEAN ± SEM [in %, of most intense distortions experienced throughout waking state]
$ Significance determined by Student's t test
* All results compared to pre rTCMS I
[a] p < 0.001 *
[c] p < 0.02 *
[d] p < 0.025 *
[e] p < 0.05 *
[b] p < 0.01

TABLE 44

Changes in taste and smell acuity in 13 patients with hyposmia, hypogeusia, phantosmia, and/or phantageusia pre and post second rTCMS treatment

| TASTANT | | | | | | | | | | | |
|---|---|---|---|---|---|---|---|---|---|---|---|
| NaCl(4) | | | SUCROSE(5) | | | HCl(8) | | | UREA (12) | | |
| DT | RT | ME | DT | RT | ME | DT | RT | ME | DT | RT | ME |
| PRE | | | | | | | | | | | |
| $5.3 \pm 1.5^{\dagger*}$ | $9.5 \pm 2.1^a$ | $50 \pm 10^{\ddagger}$ | $4.8 \pm 0.7^d$ | $7.3 \pm 1.6^{c*}$ | $46 \pm 8$ | $4.9 \pm 0.5^{c*}$ | $8.8 \pm 0.8^a$ | $46 \pm 8^c$ | $6.4 \pm 0.3^a$ | $7.9 \pm 0.3^a$ | $42 \pm 10^{c*}$ |
| POST | | | | | | | | | | | |
| $1.0 \pm 0^{ae}$ | $6.2 \pm 2.8$ | $68 \pm 9$ | $3.2 \pm 0.7$ | $4.7 \pm 1.0$ | $62 \pm 8$ | $4.1 \pm 0.7$ | $5.9 \pm 0.9^{ch}$ | $72 \pm 6^g$ | $3.4 \pm 0.5^e$ | $4.2 \pm 0.9^{hm}$ | $63 \pm 11$ |
| NORMALS | | | | | | | | | | | |
| $3.3 \pm 0.3$ | $3.4 \pm 0.2$ | $68 \pm 4$ | $3.3 \pm 0.2$ | $3.4 \pm 0.2$ | $60 \pm 4$ | $3.4 \pm 0.4$ | $3.5 \pm 0.4$ | $66 \pm 4$ | $3.6 \pm 0.4$ | $3.7 \pm 0.4$ | $68 \pm 4$ |

| ODORANT | | | | | | | | | | | |
|---|---|---|---|---|---|---|---|---|---|---|---|
| PYRIDINE(9) | | | NITROBENZENE(10) | | | THIOPHENE(10) | | | AMYL ACETATE(12) | | |
| DT | RT | ME | DT | RT | ME | DT | RT | ME | DT | RT | ME |
| PRE | | | | | | | | | | | |
| $6.2 \pm 1.2^{i\dagger}$ | $10.0 \pm 1.1^b$ | $48 \pm 10^{\ddagger}$ | $8.0 \pm 1.9^c$ | $10.3 \pm 0.6^e$ | $39 \pm 8$ | $9.0 \pm 1.8^a$ | $10.0 \pm 0.4^a$ | $57 \pm 9$ | $8.7 \pm 0.4^a$ | $10.7 \pm 0.4^a$ | $36 \pm 10$ |
| POST | | | | | | | | | | | |
| $4.8 \pm 1.1$ | $5.5 \pm 1.6^i$ | $76 \pm 5^g$ | $4.2 \pm 1.6$ | $4.0 \pm 1.4^b$ | $62 \pm 8$ | $3.0 \pm 0.9^e$ | $5.0 \pm 1.4^{bm}$ | $70 \pm 6$ | $4.0 \pm 2.0^f$ | $4.6 \pm 1.5^e$ | $51 \pm 10$ |
| NORMALS | | | | | | | | | | | |
| $3.7 \pm 0.3$ | $6.0 \pm 0.7$ | $66 \pm 5$ | $3.6 \pm 0.4$ | $6.0 \pm 0.6$ | $52 \pm 6$ | $3.2 \pm 0.6$ | $3.3 \pm 0.5$ | $69 \pm 6$ | $3.1 \pm 0.5$ | $3.3 \pm 0.6$ | $53 \pm 5$ |

†MEAN ± SEM (in BU)
‡MEAN ± SEM (in %)
*All significance determined by Student's t test
Compared to normals
$^a$p < 0.001
$^b$p < 0.005
$^c$p < 0.025
$^i$p < 0.02 = c*
$^d$p < 0.05
$^e$p < 0.001
Compared to pre rTCMS II
$^y$p < 0.01 ¢ = m*
$^f$p < 0.05
$^g$p < 0.02
$^h$p < 0.025
$^i$p < 0.05
m: <0.005 m

TABLE 45

Changes in phantageusia and phantosmia in 13 patients with hyposmia, hypogeusia, phantosmia and/or phantageusia pre and post rTCMS II

| | PHANTAGEUSIA | | PHANTOSMIA | |
|---|---|---|---|---|
| PATIENTS | PRE | POST | PRE | POST |
| TOTAL (13) | $39 \pm 10^{\dagger l}$ | $9 \pm 5^g$ | $47 \pm 8$ | $0^a$ |
| MEN (4) | $52 \pm 15$ | $6 \pm 5^h$ | $49 \pm 10$ | $0^f$ |
| WOMEN (9) | $34 \pm 6^k$ | $12 \pm 6^g$ | $44 \pm 5$ | $0^f$ |

†MEAN ± SEM [in %, of most intense distortions experienced throughout waking state]
$ Significance determined by Student's t test
* All results compared to pre rTCMS II and pre and post rTCMS I
$^a$p < 0.001 with respect to pre rTCMS II and post rTCMS I
$^f$p < 0.001 compared to pre rTCMS II and post rTCMS I
$^k$p < 0.001 compared to pre rTCMS I
$^l$p < 0.005 compared to pre rTCMS I
$^g$p < 0.02 compared to pre rTCMS II
$^h$p < 0.025 compared to pre rTCMS II

TABLE 46

| SUBSTANCE | NASAL MUCUS (pg/ml) | PLASMA (pg/ml) | SALIVA (pg/ml) | URINE (pg/ml) |
|---|---|---|---|---|
| Agout Related Protein | 4.0 ± 0.9 (pg/ml) | 38 ± 3 (pg/ml) | 6.4 ± 1.1 (pg/ml) | 147 ± 20 (pg/ml) |
| Alpha Fetoprotein (AFP) | 0 (ng/ml) | 2.7 ± 0.5 (ng/ml) | 0 (ng/ml) | 0 (ng/ml) |
| Brain Derived Neurotrophic Factor (BDNF) | 8 ± 8 (ng/ml) | 3676 ± 529 (ng/ml) | 0 (ng/ml) | 0 (ng/ml) |
| Bone Morphogenic Protein (BMP) | 0 (pg/ml) | 4.2 (pg/ml) | 0 (pg/ml) | 0 (pg/ml) |
| Ciliary Neurotrophic Factor (CNF) | 0 (pg/ml) | 0 (pg/ml) | 0 (pg/ml) | 0 (pg/ml) |
| E Selectin | 0.58 ± 0.49 (ng/ml) | 20.0 ± 4.5 (ng/ml) | 0 (ng/ml) | 0 (ng/ml) |
| Endoglin | 0.02 ± 0.06 (ng/ml) | 27 ± 0.1 (ng/ml) | 0 (ng/ml) | 0 (ng/ml) |
| Endostatin | 6.0 ± 1.3 (ng/ml) | 102 ± 9 (ng/ml) | 1.3 ± 0.3 (ng/ml) | 0.4 ± 0.02 (ng/ml) |
| Endothelial Nitric Oxide (ENO) | 0 (ng/ml) | 0 (ng/ml) | 0 (ng/ml) | 0 (ng/ml) |
| Epidermal Growth Factor (EGF) | 7730 ± 103 (pg/ml) | 52 ± 7 (pg/ml) | 1332 ± 258 (pg/ml) | 81157 ± 11254 (pg/ml) |
| Erythroporetin | 7.0 ± 3.7 (pg/ml) | 13.2 ± 2.0 (pg/ml) | 0 (pg/ml) | 0 (pg/ml) |
| FAS Ligand | 4.05 ± 1.9 (pg/ml) | 63.7 ± 8.1 (pg/ml) | 0 (pg/ml) | 0.73 ± 1.6 (pg/ml) |
| Fibroblastic Growth Factor, basic (FGF basic) | 2.81 ± 1.3 (pg/ml) | 0 (pg/ml) | 0 (pg/ml) | 0 (pg/ml) |
| inducible Nitric Oxide Synthase (iNOS) | 19.9 ± 8.0 (U/ml) | 9.5 ± 3.1 (U/ml) | 11.9 ± 3.6 (U/ml) | 15.8 ± 7.6 (U/ml) |
| Insulin-like Growth Factor (IGF-1) | 4.2 ± 0.6 (pg/ml) | — | 1.3 ± 0.3 (pg/ml) | — |
| Intercellular Adhesion Molecule 1 (ICAM-1) | 34 ± 4 (ng/ml) | 126 ± 8 (ng/ml) | 19 ± 1 (ng/ml) | 20 ± 2 (ng/ml) |
| Interferon α (IFN-α) | 4.0 ± 1.7 (pg/ml) | 2.2 ± 1.4 (pg/ml) | 12.7 ± 7.6 (pg/ml) | 70.5 ± 16.9 (pg/ml) |
| Interferon β (IFN β) | 421 ± 184 (pg/ml) | 866 ± 312 (pg/ml) | 28 ± 14 (pg/ml) | 0 (pg/ml) |
| Interferon α (IFN γ) | 85 ± 18 (pg/ml) | 0.3 ± 0.3 (pg/ml) | 0 (pg/ml) | 0 (pg/ml) |
| Interferon ω (IFN ω) | 44 ± 11 (pg/ml) | 38 ± 9 (pg/ml) | 0 (pg/ml) | 33 ± 15 (pg/ml) |
| Interleukin 1 (IL-1) | 194 ± 24 (pg/ml) | 0.1 ± 0.1 (pg/ml) | 2.8 ± 1.1 (pg/ml) | 0.3 ± 0.2 (pg/ml) |
| Interleukin 1 Receptor (IL-1R) | 1675 ± 517 (pg/ml) | 18357 ± 1922 (pg/ml) | 19.7 ± 4.3 (pg/ml) | 436 ± 68 (pg/ml) |
| Interleukin 2 (IL-2) | 6.9 ± 5.4 (pg/ml) | 0 (pg/ml) | 0 (pg/ml) | 0 (pg/ml) |
| Interleukin 2 Receptor (IL-2 receptor) | 68.8 ± 24.2 (pg/ml) | 994.7 ± 101.3 (pg/ml) | 11.8 ± 4.6 (pg/ml) | 1177.7 ± 104.1 (pg/ml) |
| Interleukin 3 (IL-3) | 70.8 ± 23.4 (pg/ml) | — | 105 ± 25 (pg/ml) | — |
| Interleukin 6 (IL-6) | 21.60 ± 12.80 (pg/ml) | 1.25 ± 0.18 (pg/ml) | 0.79 ± 0.11 (pg/ml) | 1.52 ± 0.43 (pg/ml) |
| Interleukin 15 (IL-15) | 21.6 ± 8.9 (pg/ml) | 0.67 ± 0.12 (pg/ml) | 0.56 ± 0.21 (pg/ml) | 0.59 ± 0.36 (pg/ml) |
| Interleukin 17 (IL-17) | 2.06 ± 1.18 (pg/ml) | 0 (pg/ml) | 1.80 ± 0.7 (pg/ml) | 3.49 ± 1.44 (pg/ml) |
| Interleukin 18 (IL-18) | 270 ± 85 (pg/ml) | 334 ± 52 (pg/ml) | 106 ± 22 (pg/ml) | 0 (pg/ml) |
| Keratinocyte Growth Factor (KGF) | 15.2 ± 2.9 (pg/ml) | 2.8 ± 2.8 (pg/ml) | 0 (pg/ml) | 0 (pg/ml) |
| L Selectin | 25.35 ± 3.15 (ng/ml) | 20.1 ± 1.4 (ng/ml) | 0 (ng/ml) | 0 (ng/ml) |
| Leptin | 272 ± 70 (pg/ml) | 8788 ± 903 (pg/ml) | 7.1 ± 1.0 (pg/ml) | 0 (pg/ml) |
| Leukemia Inhibitory Factor (LIF) | 5.2 ± 3.8 (pg/ml) | 0 (pg/ml) | 0 (pg/ml) | 0 (pg/ml) |
| Macrophage Inhibitory Factor (MIF) | 135 ± 27 (pg/ml) | 2.8 ± 0.2 (pg/ml) | 0 (pg/ml) | 0 (pg/ml) |
| Matrix Metalliproteinase 1 (MMP-1) | 0.3 ± 0.1 (ng/ml) | 0.8 ± 0.2 (ng/ml) | 0 (ng/ml) | 0 (ng/ml) |
| P Selectin | 1.64 ± 0.34 (pg/ml) | 30.4 ± 1.7 (pg/ml) | 0 (pg/ml) | 0 (pg/ml) |
| Placental Growth Factor (PGF) | 170 ± 50 (pg/ml) | 11 ± 4 (pg/ml) | 9 ± 3 (pg/ml) | 12 ± 4 (pg/ml) |
| Platelet Derived Growth Factor (PDGF) | 420 ± 63 (pg/ml) | 560 ± 166 (pg/ml) | 673 ± 188 (pg/ml) | 0 (pg/ml) |
| Platelet Derived Growth Factor-AA (PDGF) | 420 ± 65 (pg/ml) | 560 ± 166 (pg/ml) | 673 ± 188 (pg/ml) | 0 (pg/ml) |
| Receptor for Advanced Glycotion End Product (RAGE) | 0 (pg/ml) | 935 ± 89 (pg/ml) | 0 (pg/ml) | 0 (pg/ml) |
| Stem Cell Factor (SCF) | 33.3 ± 4.6 (pg/ml) | 846 ± 45 (pg/ml) | — | 46.4 ± 6.2 (pg/ml) |
| Substance P | 270 ± 74 (pg/ml) | 250 ± 31 (pg/ml) | 137 ± 47 (pg/ml) | 205 ± 27 (pg/ml) |
| Thymus and Activation Regulated Chemokine (TARC) | 1303 ± 830 (pg/ml) | 875 ± 240 (pg/ml) | 0 (pg/ml) | 0 (pg/ml) |
| Tissue Inhibitor of Metalloproteinase 1 (TIMP-1) | 4326 ± 553 (ng/ml) | 437 ± 114 (ng/ml) | 215 ± 62 (ng/ml) | 0 (ng/ml) |
| TRAIL | 4681 ± 464 (pg/ml) | 69 ± 17 (pg/ml) | 685 ± 15 (pg/ml) | 69 ± 12 (pg/ml) |
| Triggering Receptor Expressed on Myeloid Cells (TREM-1) | 899.9 ± 203.0 (ng/ml) | 83.42 ± 12.2 (ng/ml) | 0.0 ± 0 (ng/ml) | 0.0 ± 0 (ng/ml) |
| Tumor Growth Factor alpha (TFG-alpha) | 46 ± 8 (pg/ml) | 0 (pg/ml) | 0 (pg/ml) | 0 (pg/ml) |

TABLE 46-continued

Comparison of Biological Substances in Various Bodily Fluids

| SUBSTANCE | NASAL MUCUS (pg/ml) | PLASMA (pg/ml) | SALIVA (pg/ml) | URINE (pg/ml) |
|---|---|---|---|---|
| Tumor Growth Factor β (TGF β) | 783 ± 155 (pg/ml) | 339 ± 7 (pg/ml)0 | 363 ± 56 (pg/ml) | 0 (pg/ml) |
| Tumor Necrosis Factor alpha (TNF-alpha) | 2.2 ± 0.1 (pg/ml) | 3.4 ± 0.3 (pg/ml) | 0.39 ± 2.03 (pg/ml) | 2.0 ± 0.1 (pg/ml) |
| Tumor Necrosis Factor alpha Receptor (TNF-alpha R) | 2.2 ± 0.1 (pg/ml) | 3.4 ± 0.3 (pg/ml) | 0.4 ± 0.03 (pg/ml) | 2.0 ± 0.14 (pg/ml) |
| Tumor Necrosis Factor β (TNF β) | 0 (pg/ml) | 0 (pg/ml) | 0 (pg/ml) | 0 (pg/ml) |
| Tumor Necrosis Factor - Receptor 1 (TNF R1) | 938 ± 88 (pg/ml) | 1583 ± 73 (pg/ml) | 121 ± 6 (pg/ml) | 1445 ± 127 (pg/ml) |
| Tumor Necrosis Factor - Receptor 2 (TNF R2) | 794 ± 78 (pg/ml) | 1585 ± 73 (pg/ml) | 85 ± 7 (pg/ml) | 1445 ± 127 (pg/ml) |
| Vascular Cell Adhesion Molecule 1 (VCAM-1) | 81 ± 34 (ng/ml) | 746 ± 91 (ng/ml) | 76 ± 15 (ng/ml) | 0 (ng/ml) |
| Vascular Endothelial Growth Factor (VEGF) | 5267 ± 714 (pg/ml) | 67 ± 17 (pg/ml) | 3589 ± 630 (pg/ml) | 69 ± 12 (pg/ml) |
| Vascular Endothelial Growth Factor C (VEGF-C) | 3449 ± 536 (pg/ml) | 336.8 ± 52.1 (pg/ml) | 379.8 ± 57.7 (pg/ml) | — |
| Vascular Endothelial Growth Factor D (VEGF-D) | 29.2 ± 8.2 (pg/ml) | 469.0 ± 57.4 (pg/ml) | 6.5 ± 5.5 (pg/ml) | 11.7 ± 7.9 (pg/ml) |
| Vascular Endothelial Growth Factor - Receptor 1 (VEGF-R1) | 1532 ± 445 (pg/ml) | 378 ± 37 (pg/ml) | 492 ± 63 (pg/ml) | 317 ± 39 (pg/ml) |
| Vascular Endothelial Growth Factor - Receptor 2 (VEGF-R2) | 350 ± 149 (pg/ml) | 5074 ± 258 (pg/ml) | 99 ± 25 (pg/ml) | 223 ± 73 (pg/ml) |

TABLE 47

Examples Where Nasal Mucus Monitoring Can Replace Other Assay Methods for Predicting Future Development of Disease

| Disease | Biomarker and Change | Current Diagnostic Method | Prevalence of Disease | Time Before Symptoms Appear |
|---|---|---|---|---|
| Wilson's Disease | Tissue Copper Increases | Ceruroplasmin level Copper level in Blood, Urine or Liver Biopsy | 95-100 | 1-10 Years |
| Chronic Obstructive Pulmonary Disease (COPD) | C Reactive Protein Increases | Blood | 20 | 1-8 Years |
| Preeclampsia | Endoglin Increases | Blood | 3-5 | 2-10 Weeks |
| Coronary Heart Disease (Mortality) | N-Terminal-Por-B-Type Natriuretic Peptide Increases | Blood | 5-10 | Weeks-Years |
| Repeat Thromboembolism | D-Dimer Present After Anticoagulation Therapy Terminated | Blood | 15 | Weeks |

TABLE 48

Blood Endoglin Levels in Patients that Develop Preeclampsia Compared to Controls

| PREGNANCY PERIOD | PREECLAMPSIA | CONTROLS |
|---|---|---|
| ONSET | 46.4 (ng/ml) | 9.8 (ng/ml) |
| 17-20 WEEKS | 10.2 (ng/ml) | 5.8 (ng/ml) |
| 25-28 WEEKS | 8.6 (ng/ml) | 5.9 (ng/ml) |
| TERM | 31.0 (ng/ml) | 13.3 (ng/ml) |

TABLE 49

Blood & Nasal Mucus Levels of Endoglin and Placental Like Growth Factor

| SUBSTANCE | BLOOD CONCENTRATION | NASAL MUCUS CONCENTRATION |
|---|---|---|
| ENDOGLIN (ng/ml) | 12.7 ± 0.2 (1.1-6.0) | 0.8 ± 0.5 (0.02-3.0) |
| PLACENTAL LIKE GROWTH FACTOR (PlGF) (pg/ml) | 21 ± 4 (0-79) | 372 ± 17 (32-1402) |

TABLE 50

Comparison of Copper Levels in Patients with
Taste and Smell Deficits and Controls

| | Nasal Mucus (mg/l) | Saliva (mg/l) | Plasma (mg/dl) | Urine (mg/24 hrs) |
|---|---|---|---|---|
| Control | 99 ± 8 | 22 ± 1 | 102 ± 10 | 110 ± 25 |
| Wilson's Disease | 2 ± 1 | 3 ± 1 | 12 ± 2 | 5 ± 1 |
| Non-Wilson's Disease Patients | 134 ± 8 | 28 ± 8 | 105 ± 20 | 120 ± 30 |

TABLE 51

Comparison of Zince Levels in Patients with Taste and
Smell Deficits and Controls

| | Nasal Mucus (mg/l) | Saliva (mg/l) | Plasma (mg/dl) | Urine (mg/24 hrs) |
|---|---|---|---|---|
| Controls | 96 ± 10 | 89 ± 10 | 84 ± 12 | 425 ± 25 |
| Non-Wilson's Disease Patients | 236 ± 37 | 70 ± 20 | 64 ± 8 | 395 ± 35 |

What is claimed is:

1. A method for treating hyposmia or hypogeusia in a subject in need thereof comprising:
   a. treating the hyposmia or the hypogeusia by performing transcranial magnetic stimulation (TCMS) or repetitive transcranial magnetic stimulation (rTCMS) on the subject in need thereof.

2. The method of claim 1, wherein the subject in need thereof has a greater decrease in a detection threshold (DT) and/or a recognition threshold (RT) for at least one tastant or odorant after the TCMS or rTCMS than a subject given a sham treatment.

3. The method of claim 2, comprising treating the hypogeusia, wherein the subject in need thereof has the greater decrease in the DT or RT for the tastant that is NaCl, sucrose, HCl, or urea.

4. The method of claim 2, comprising treating the hyposmia wherein the subject in need thereof has the greater decrease in the DT or RT for the odorant that is pyridine, nitrobenzene, thiophene, or amyl acetate.

5. The method of claim 1, wherein the subject in need thereof has a greater increase in a magnitude estimation (ME) for at least one tastant or odorant after the TCMS or rTCMS than a subject given a sham treatment.

6. The method of claim 5, comprising treating the hypogeusia, wherein the subject in need thereof has the greater increase in the ME for the tastant that is NaCl, sucrose, HCl, or urea.

7. The method of claim 5, comprising treating the hyposmia, wherein the subject in need thereof has the greater increase in the ME for the odorant that is pyridine, nitrobenzene, thiophene, or amyl acetate.

8. The method of claim 1, wherein the subject in need thereof has an increase in a plasma, erythrocyte, and/or saliva level of zinc, copper, carbonic anhydrase I (CA I), carbonic anhydrase II (CA II), carbonic anhydrase VI (CA VI), or a combination thereof after the TCMS or rTCMS.

9. The method of claim 1, wherein the TCMS or rTCMS is applied to one or more skull locations of the subject in need thereof, the skull locations comprising a left temporoparietal, a right temporoparietal, an occipital, and/or a frontal location.

10. The method of claim 1, comprising performing rTCMS comprising 1 pulse every 1 to 3 seconds.

11. The method of claim 1, comprising performing rTCMS comprising 1 pulse every 1 to 3 seconds for 30 to 90 seconds.

12. The method of claim 1, comprising performing rTCMS comprising 1 pulse every 1 to 3 seconds for 30 to 90 seconds for about 20 total pulses per application.

13. The method of claim 1, comprising performing rTCMS comprising about 20 total pulses per application.

14. The method of claim 9, comprising performing rTCMS comprising 1 pulse every 1 to 3 seconds.

15. The method of claim 9, comprising performing rTCMS comprising 1 pulse every 1 to 3 seconds for 30 to 90 seconds.

16. The method of claim 9, comprising performing rTCMS comprising 1 pulse every 1 to 3 seconds for 30 to 90 seconds for about 20 total pulses per skull location per application.

17. The method of claim 9, comprising performing rTCMS comprising about 20 total pulses per skull location per application.

18. The method of claim 1, wherein the subject in need thereof experiences a reduction in phantageusia and/or phantosmia after the TCMS or rTCMS.

* * * * *